(12) United States Patent
Funk et al.

(10) Patent No.: US 12,728,183 B2
(45) Date of Patent: Sep. 8, 2026

(54) MEDICAL SYSTEM INCLUDING STEERABLE CATHETER AND METHOD OF MANUFACTURING

(71) Applicant: KARDIUM INC., Burnaby (CA)

(72) Inventors: John Andrew Funk, Delta (CA); Ashkan Sardari, North Vancouver (CA)

(73) Assignee: KARDIUM INC., Burnaby (CA)

( * ) Notice: Subject to any disclaimer, the term of this patent is extended or adjusted under 35 U.S.C. 154(b) by 1025 days.

(21) Appl. No.: 17/947,382

(22) Filed: Sep. 19, 2022

(65) Prior Publication Data

US 2023/0008203 A1 Jan. 12, 2023

Related U.S. Application Data

(63) Continuation of application No. PCT/CA2021/050495, filed on Apr. 13, 2021.

(60) Provisional application No. 63/015,925, filed on Apr. 27, 2020.

(51) Int. Cl.
*A61M 25/00* (2006.01)
*A61L 29/14* (2006.01)

(52) U.S. Cl.
CPC ......... *A61L 29/14* (2013.01); *A61M 25/0012* (2013.01); *A61M 25/0045* (2013.01)

(58) Field of Classification Search
CPC .......... A61M 25/0012; A61M 25/0045; A61M 25/0053; A61M 25/0144; A61M 25/005
See application file for complete search history.

(56) References Cited

U.S. PATENT DOCUMENTS 5,019,057 A 5/1991 Truckai
5,715,817 A 2/1998 Stevens-Wright et al.
5,782,811 A 7/1998 Samson et al.
6,450,948 B1 9/2002 Matsuura et al.
6,709,429 B1 * 3/2004 Schaefer .................. D04C 1/06 604/524
6,890,329 B2 5/2005 Carroll et al.
7,914,515 B2 3/2011 Heideman et al.
8,444,637 B2 5/2013 Podmore et al.
(Continued)

FOREIGN PATENT DOCUMENTS

AU 2016253129 A1 10/2017
EP 2018204 B1 6/2012
(Continued)

OTHER PUBLICATIONS

Extended European Search Report issued in European Appln. No. 21796280.2, mailed Apr. 26, 2024.
(Continued)

*Primary Examiner* — Laura A Bouchelle
(74) *Attorney, Agent, or Firm* — ROSSI, KIMMS & McDOWELL LLP

(57) ABSTRACT

A steerable catheter may include an elongate shaft member and a braided reinforcement structure embedded into a wall of the elongate shaft member. The braided reinforcement structure may include a first braided portion including a first pick count, a second braided portion including a second pick count, and a third braided portion including a third pick count. The third pick count may be greater than each of the first pick count and the second pick count.

30 Claims, 11 Drawing Sheets

(56) References Cited

U.S. PATENT DOCUMENTS

| | | | |
|---|---|---|---|
| 8,603,066 | B2 | 12/2013 | Heidman et al. |
| 8,734,699 | B2 | 5/2014 | Heideman et al. |
| 9,114,229 | B2 | 8/2015 | Fuentes |
| 10,099,036 | B2 | 10/2018 | Heideman et al. |
| 10,426,920 | B2 | 10/2019 | Sutermeister et al. |
| 10,912,923 | B2 | 2/2021 | Heideman et al. |
| 10,987,490 | B2 | 4/2021 | Olson et al. |
| 11,484,690 | B2 | 11/2022 | Tegg et al. |
| 2002/0161353 | A1 | 10/2002 | Kortelling |
| 2003/0009184 | A1 | 1/2003 | Pepin |
| 2009/0043299 | A1 | 2/2009 | Racz |
| 2013/0046298 | A1 | 2/2013 | Kaufman |
| 2016/0228136 | A1 | 8/2016 | Schaeffer |
| 2019/0231466 | A1 | 8/2019 | Weitzner et al. |
| 2020/0275983 | A1 | 9/2020 | Dewaele et al. |

FOREIGN PATENT DOCUMENTS

| | | | |
|---|---|---|---|
| EP | 2167179 | B9 | 2/2014 |
| EP | 3579908 | B1 | 12/2020 |
| WO | 0013733 | A2 | 3/2000 |
| WO | 12013016722 | A2 | 1/2013 |
| WO | 2016172706 | A1 | 10/2016 |
| WO | 2021217243 | A1 | 11/2021 |

OTHER PUBLICATIONS

Notice of Allowance issued in U.S. Appl. No. 17/947,340 mailed Aug. 6, 2025.

International Search Report issued in International Application No. PCT/CA2021/050495 mailed Jul. 21, 2021.

Written Opinion issued in International Application No. PCT/CA2021/050495 mailed Jul. 21, 2021.

International Search Report issued in International Application No. PCT/CA2021/050496 mailed Jul. 14, 2021.

Written Opinion issued in International Application No. PCT/CA2021/050496 mailed Jul. 14, 2021.

Copending U.S. Appl. No. 17/947,340, filed Sep. 19, 2022 (a copy is not included because the cited application is not yet available to the public and the Examiner has ready access to the cited application).

* cited by examiner 214
213
215
219
D1
200
210
204
212
210
246a
226
240
246b
244
221
242
241a
228
244

213
200
215
214
219
210
204
212
210
226
240
244
221
242
228
244

215
213
219
214
200
D2
210
204
212
210
248b
226
240
248a
244
221
242
241b
228
244

MEDICAL SYSTEM INCLUDING STEERABLE CATHETER AND METHOD OF MANUFACTURING

CROSS-REFERENCE TO RELATED APPLICATION

This application is a bypass continuation of prior Patent Cooperation Treaty International Application No. PCT/CA2021/050495, filed Apr. 13, 2021, which claims the benefit of U.S. Provisional Application No. 63/015,925, filed Apr. 27, 2020, the entire disclosure of each of the applications cited in this section is hereby incorporated herein by reference.

TECHNICAL FIELD

Aspects of this disclosure generally are related to medical systems. In particular, aspects of this disclosure relate to medical systems that include a steerable shaft member that may be deployed through a bodily opening leading to a bodily cavity.

BACKGROUND

Cardiac surgery was initially undertaken using highly invasive open procedures. A sternotomy, which is a type of incision in the center of the chest that separates the sternum, was typically employed to allow access to the heart. In the past several decades, however, more and more cardiac operations are performed using intravascular or percutaneous techniques, where access to inner organs or other tissue is gained via a catheter.

Intravascular or percutaneous surgeries benefit patients by reducing surgery risk, complications, and recovery time. However, the use of intravascular or percutaneous technologies also raises some particular challenges. Medical devices used in intravascular or percutaneous surgery need to be deployed via catheter systems which significantly increase the complexity of the device structure. As well, doctors do not have direct visual contact with the medical devices once the devices are positioned within the body.

The positioning of a medical device is crucial to such procedures. For accurate positioning, a catheter needs to be bent or steered as it is deployed through a bodily opening (e.g., an artery) and into a bodily cavity (e.g., an atrium in a heart). By way of the steering, an end of a catheter can be deflected or bent in one or another direction. The steering function can be controlled via the use of one or more axial members (e.g., steering members including various wires, lines, or cables) positioned within the catheter (e.g., within a wall of the catheter). The degree and order of pulling, tensioning, or taking up and playing out the steering members control the degree of deflection of the catheter.

Conventional steerable catheters, however, have certain shortcomings. For example, it is often desired to bend or deflect a steerable portion of the catheter in a pre-determined plane, when one or more axial steering members of the catheter are retracted or advanced. High forces applied by the axial steering members can cause the steerable portion of the catheter to be deflected laterally from the pre-determined plane in an undesired manner. The high forces applied by the axial steering members may also cause other problems. For example, the present inventors recognized that compressive loading provided by the axial steering members can cause the elongated catheter to shorten, thereby providing a user with a false indication of where the distal end of the catheter may be during the steering or deflecting thereof. The present inventors also recognized that such conventional steerable catheter devices are limited in the amount and manner that they can be deflected or bent. The present inventors recognized that such limitations may make it difficult or impossible to position a medical device as desired within a bodily cavity. The present inventors also recognized that any solutions configured to address these limitations must not unduly increase various dimensions of the catheter in a manner that would hinder, limit, or restrict delivery of the catheter within the body of the patient. Further, the present inventors recognized that any solutions configured to address these limitations must remain safe for the patient and properly protect against failure conditions of the catheter. Accordingly, a need in the art exists for improved intra-bodily cavity medical devices.

SUMMARY

At least the above-discussed need is addressed and technical solutions are achieved by various embodiments of the present invention. According to some embodiments, a steerable catheter may be summarized as including an elongate shaft member including a proximal portion, a distal portion, and a steerable portion located between the proximal portion and the distal portion, the elongate shaft member configured to be deliverable at least partially through a bodily opening leading to a bodily cavity with the distal portion ahead of the steerable portion. According to some embodiments, the steerable catheter may include an actuator set located at least proximate the proximal portion, the actuator set operatively coupled to the steerable portion to transmit force thereto to steer at least the steerable portion. According to some embodiments, the steerable catheter may include a braided reinforcement structure, at least part of the braided reinforcement structure embedded into at least part of a wall of the elongate shaft member. According to some embodiments, the braided reinforcement structure may include a first braided portion including a first pick count, the first braided portion of the braided reinforcement structure extending along at least part of the proximal portion of the elongate shaft member. According to some embodiments, the braided reinforcement structure may include a second braided portion including a second pick count. In some embodiments, the second braided portion of the braided reinforcement structure may extend along at least part of the distal portion of the elongate shaft member. According to some embodiments, the braided reinforcement structure may include a third braided portion including a third pick count that is greater than each of the first pick count and the second pick count. In some embodiments, the third braided portion of the braided reinforcement structure may extend along at least part of the steerable portion of the elongate shaft member. According to some embodiments, the second pick count may be different than the first pick count.

According to some embodiments, the braided reinforcement structure includes a plurality of filaments, the plurality of filaments braided together to form the braided reinforcement structure. In some embodiments, each of the first braided portion of the braided reinforcement structure, the second braided portion of the braided reinforcement structure, and the third braided portion of the braided reinforcement structure may include a respective portion of each filament of the plurality of filaments. According to some embodiments, a first ring is incorporated in the proximal portion of the elongate shaft member, and a second ring is incorporated in the distal portion of the elongate shaft member. In some embodiments, at least some filaments of the plurality of filaments of the braided reinforcement structure may be directly fixedly connected to the first ring, and at least some filaments of the plurality of filaments of the braided reinforcement structure may be directly fixedly connected to the second ring. According to some embodiments, each filament of the plurality of filaments is a metallic filament, and each of the first ring and the second ring is a metallic ring. In some embodiments, each filament of the at least some filaments directly fixedly connected to the first ring may be directly fixedly connected to the first ring via a welded connection, and each filament of the at least some filaments directly fixedly connected to the second ring may be directly fixedly connected to the second ring via a welded connection. According to some embodiments, each of the at least some filaments may include (a) a plurality of first portions that underlie other filament portions in the braided reinforcement structure, and (b) a plurality of second portions that overlie other filament portions in the braided reinforcement structure. In some embodiments, each filament of the at least some filaments directly fixedly connected to the first ring may be directly fixedly connected to the first ring via a welded connection connecting one or more first portions of the at least some filaments to the first ring, and each filament of the at least some filaments directly fixedly connected to the second ring may be directly fixedly connected to the second ring via a welded connection connecting one or more first portions of the at least some filaments to the second ring.

According to some embodiments, the wall of the elongate shaft member may be provided at least in part by a tubular member of the elongate shaft member. According to some embodiments, at least the part of the braided reinforcement structure may be distanced from (a) an exterior surface of the tubular member, and (b) an interior surface of the tubular member. According to some embodiments, at least the part of the braided reinforcement structure may not interrupt any exterior surface of the tubular member and may not interrupt any interior surface of the tubular member. According to some embodiments, the braided reinforcement structure may be circumferentially arranged about a central longitudinal axis of the elongate shaft member, the central longitudinal axis extending between the proximal portion of the elongate shaft member and the distal portion of the elongate shaft member.

According to some embodiments, the first braided portion of the braided reinforcement structure may be embedded in at least a first polymer portion of the wall of the elongate shaft member, the first polymer portion including a first hardness; the second braided portion of the braided reinforcement structure may be embedded in at least a second polymer portion of the wall of the elongate shaft member, the second polymer portion including a second hardness; and the third braided portion of the braided reinforcement structure may be embedded in at least a third polymer portion of the wall of the elongate shaft member, the third polymer portion including a third hardness. In some embodiments, each of the first hardness and the second hardness may be harder than the third hardness. In some embodiments, the first hardness may be harder than the second hardness.

According to some embodiments, the steerable catheter may include at least a first steering member, at least part of the first steering member incorporated into at least a first portion of the wall of the elongate shaft member. In some embodiments, the actuator is configured to manipulate the at least the first steering member to cause deflection of the at least the steerable portion in a first particular plane. In some embodiments, the at least the first steering member extends between the proximal portion of the elongate shaft member and the distal portion of the elongate shaft member. According to some embodiments, at least part of the third braided portion of the braided reinforcement structure may surround at least a first portion of the first steering member. According to some embodiments, at least part of the first braided portion of the braided reinforcement structure may surround at least a second portion of the first steering member. According to some embodiments, at least part of the second braided portion of the braided reinforcement structure may surround at least a second portion of the first steering member.

According to some embodiments, a steering ring may be incorporated in the distal portion of the elongate shaft member, and the at least the first steering member is directly fixedly connected to the steering ring. In some embodiments, at least the second braided portion of the braided reinforcement structure may be radially exterior (e.g., further outside), with respect to a central longitudinal axis of the elongate shaft member, of at least a region of the steering ring to which the at least the first steering member is directly fixedly connected. In some embodiments, the steering ring is a metallic steering ring, and each of the at least the first steering member is a respective metallic steering member, the respective metallic steering member welded to the metallic ring. In some embodiments, the respective metallic steering member may be welded to the metallic ring through an opening defined by braids of the second braided portion of the braided reinforcement structure.

According to some embodiments, the steerable catheter may include at least a first axial strengthening member, at least part of the first axial member embedded into at least a second portion of the wall of the elongate shaft member. In some embodiments, the at least the first axial strengthening member extends between the proximal portion of the elongate shaft member and the distal portion of the elongate shaft member. In some embodiments, the at least the first axial strengthening member is configured to (a) reduce lateral deflection of the at least the steerable portion of the elongate shaft member away from the first particular plane during the deflection of the at least the steerable portion of the elongate shaft member in the first particular plane, (b) provide increased resistance to compressive loading failure of at least part of the elongate shaft member during the deflection of the at least the steerable portion of the elongate shaft member in the first particular plane, or both (a) and (b). In some embodiments, the at least the first axial strengthening member may not be directly fixedly connected to the steering ring. In some embodiments, at least the second braided portion of the braided reinforcement structure may be radially exterior, with respect to a central longitudinal axis of the elongate shaft member, of at least a region of the steering ring to which the at least the first steering member is directly fixedly connected. In some embodiments, at least part of the second braided portion of the braided reinforcement structure may be radially exterior, with respect to the central longitudinal axis of the elongate shaft member, of at least a first part of the at least the first axial strengthening member. In some embodiments, the at least the first axial strengthening member may be woven among braids of the at least the second braided portion of the braided reinforcement structure. In some embodiments, the at least the first axial strengthening member may be woven among braids of at least the first braided portion of the braided reinforcement structure. In some embodiments, the at least the first axial strengthening member may be woven among braids of at least the third braided portion of the braided reinforcement structure.

According to some embodiments, the proximal portion of the elongate shaft member may extend to a handle portion of the steerable catheter. According to some embodiments, the first pick count of the first braided portion of the braided reinforcement structure may be in a range of 15 picks per inch of length ("PPI") to 30 PPI. According to some embodiments, the second pick count of the second braided portion of the braided reinforcement structure may be in a range of 15 PPI to 30 PPI. According to some embodiments, the third pick count of the third braided portion of the braided reinforcement structure may be in a range of 24 PPI to 36 PPI.

Various steerable catheters in other embodiments may include combinations or sub-combinations of features described above.

According to some embodiments, a catheter may be summarized as including an elongate shaft member including a proximal portion, a distal portion, and a wall, the elongate shaft member configured to be deliverable at least partially through a bodily opening leading to a bodily cavity with the distal portion ahead of the proximal portion, and the wall of the elongate shaft member including one or more polymer layers. According to some embodiments, the catheter may include an elongate thermoplastic member, at least part of the elongate thermoplastic member embedded into at least a particular polymer layer of the one or more polymer layers of the wall of the elongate shaft member, the embedded at least the part of the elongate thermoplastic member extending along or with a longitudinal axis of the elongate shaft member between the proximal portion of the elongate shaft member and the distal portion of the elongate shaft member. According to some embodiments, the catheter may include a reinforcement structure surrounding the embedded at least the part of the elongate thermoplastic member, at least part of the reinforcement structure embedded into the wall of the elongate shaft member, at least a portion of the embedded at least the part of the reinforcement structure including a plurality of filaments, each of at least one filament of the plurality of filaments having a particular dimension in a radial direction with respect to the longitudinal axis of the elongate shaft member. According to some embodiments, at least a first portion of the embedded at least the part of the elongate thermoplastic member may include indentations in a surface of the first portion of the embedded at least the part of the elongate thermoplastic member into which the portion of the embedded at least the part of the reinforcement structure is embedded. According to some embodiments, a depth of each of at least some of the indentations from the surface of the first portion of the embedded at least the part of the elongate thermoplastic member may be at least 40% of the particular dimension of the respective filament.

According to some embodiments, the first portion of the embedded at least the part of the elongate thermoplastic member may have a semi-crystalline state. According to some embodiments, at least the first portion of the embedded at least the part of the elongate thermoplastic member may exhibit a characteristic of having undergone cold crystallization. According to various embodiments, the particular polymer layer of the one or more polymer layers of the wall of the elongate shaft member has a particular melt temperature, and the embedded at least the part of the elongate thermoplastic member has a particular glass transition temperature. In some embodiments, the particular glass transition temperature of the embedded at least the part of the elongate thermoplastic member may be within 20% of the particular melt temperature at least in Celsius of the particular polymer layer of the one or more polymer layers of the wall of the elongate shaft member. In some embodiments, the embedded at least the part of the elongate thermoplastic member may have a particular melt temperature that is greater than the particular melt temperature of the particular polymer layer of the one or more polymer layers of the wall of the elongate shaft member.

According to some embodiments, at least the part of the reinforcement structure may be embedded in at least the particular polymer layer of the one or more polymer layers of the wall of the elongate shaft member. In some embodiments, the particular polymer layer of the one or more polymer layers of the wall of the elongate shaft member may be a tubular layer. In some embodiments, the tubular layer includes an outer surface and an inner surface radially inward from the outer surface with respect to the longitudinal axis of the elongate shaft member, and the embedded at least the part of the elongate thermoplastic member may be located between the outer surface and the inner surface.

According to some embodiments, the reinforcement structure may include a helical structure. According to some embodiments, a first set of the plurality of filaments are wound in a first direction and a second set of the plurality of filaments may be wound in a second direction opposite the first direction. According to some embodiments, the reinforcement structure may include a braided structure. According to some embodiments, the embedded at least the part of the elongate thermoplastic member may be woven among braids of the braided structure. According to some embodiments, the embedded at least the part of the elongate thermoplastic member may be woven among at least some of the plurality of filaments. According to some embodiments, a portion of each filament of at least some of the plurality of filaments may be embedded in a respective indentation of the indentations in the surface of the first portion of the embedded at least the part of the elongate thermoplastic member.

In some embodiments, the surface of the first portion of the embedded at least the part of the elongate thermoplastic member includes a first surface portion and a second surface portion, the first surface portion located radially closer to the longitudinal axis of the elongate shaft member than the second surface portion. In some embodiments, a first set of the indentations may be provided in the first surface portion and a second set of the indentations may be provided in the second surface portion. According to some embodiments, a depth of at least one indentation of the first set of the indentations from the first surface portion may be different than a depth of at least one indentation of the second set of the indentations from the second surface portion. According to some embodiments, a depth of at least one indentation of the first set of the indentations from the first surface portion may be greater than a depth of at least one indentation of the second set of the indentations from the second surface portion.

According to some embodiments, the elongate thermoplastic member is a first elongate thermoplastic member, the catheter may include a second elongate thermoplastic member, at least part of the second elongate thermoplastic member embedded into the wall of the elongate shaft member. According to some embodiments, at least a portion of the second elongate thermoplastic member may be positioned diametrically opposite across at least one cross-section of the elongate shaft member from at least a portion of the first elongate thermoplastic member.

According to some embodiments, the elongate shaft member may include a steerable portion. In some embodiments, the catheter may include an actuator located at least proximate the proximal portion of the elongate shaft member, the actuator operatively coupled to the steerable portion to transmit force thereto to steer at least the steerable portion. In some embodiments, the steerable portion of the elongate shaft member is located between the proximal portion of the elongate shaft member and the distal portion of the elongate shaft member. In some embodiments, the actuator may be operatively coupled to the steerable portion to cause deflection of the at least the steerable portion in a first particular plane. In some embodiments, the elongate thermoplastic member may be configured at least to resist, at least in part, lateral deflection of the at least the steerable portion away from the first particular plane during the deflection of the at least the steerable portion in the first particular plane. In some embodiments, the elongate thermoplastic member is a first elongate thermoplastic member, and the catheter may include a second elongate thermoplastic member, at least part thereof embedded in the wall of the elongate shaft member and extending between the proximal portion of the elongate shaft member and the distal portion of the elongate shaft member. According to some embodiments, each of the first elongate thermoplastic member and the second elongate thermoplastic member include a respective axis extending between the proximal portion of the elongate shaft member and the distal portion of the elongate shaft member. According to some embodiments, the second elongate thermoplastic member may be configured at least to resist, at least in part, the lateral deflection of the at least the steerable portion away from the first particular plane during the deflection of the at least the steerable portion in the first particular plane. In some embodiments, the respective axis of the first elongate thermoplastic member and the respective axis of the second elongate thermoplastic member may lie in a second particular plane, the second particular plane intersecting the first particular plane. According to some embodiments, the second particular plane may be orthogonal to the first particular plane. According to some embodiments, the catheter may include a first steering member and a second steering member, and the actuator is configured to manipulate the first steering member, the second steering member, or both the first steering member and the second steering member, to cause deflection of the at least the steerable portion in the first particular plane. In some embodiments, at least a first portion of the reinforcement structure may surround at least a respective portion of each of the first steering member and the second steering member. In some embodiments, the reinforcement structure may include a braided structure, and at least the first steering member may be woven among braids of the braided structure.

According to some embodiments, the first portion of the embedded at least the part of the elongate thermoplastic member has been melted about the portion of the embedded at least the part of the reinforcement structure to embed the portion of the embedded at least the part of the reinforcement structure into the surface of the first portion of the embedded at least the part of the elongate thermoplastic member, thereby forming the indentations. In some embodiments, the first portion of the embedded at least the part of the elongate thermoplastic member has a semi-crystalline state.

According to some embodiments, at least the first portion of the embedded at least the part of the elongate thermoplastic member may include a polyaryletherketone (PAEK) polymer. In some embodiments, the polyaryletherketone (PAEK) polymer is polyether ether ketone (PEEK).

Various catheters in other embodiments may include combinations or sub-combinations of features described above.

According to some embodiments, a method of manufacturing at least part of a steerable catheter may be summarized as including axially positioning at least a portion of an elongate thermoplastic member axially adjacent at least a portion of a tubular member of an elongate shaft member, the elongate thermoplastic member including at least a first portion including an amorphous state. In some embodiments, the method may include heating at least part of the axially adjacent elongate thermoplastic member at least to change the amorphous state of the at least the first portion of the elongate thermoplastic member to a semi-crystalline state. In some embodiments, the method may include embedding at least part of the elongate thermoplastic member into at least part of a wall of the elongate shaft member, the embedded at least the part of the elongate thermoplastic member extending along an axis of the elongate shaft member between a proximal portion of the elongate shaft member and a steerable portion of the elongate shaft member, the elongate shaft member configured to be deliverable at least partially through a bodily opening leading to a bodily cavity with the steerable portion ahead of the proximal portion.

According to some embodiments, the method may include surrounding at least the part of the elongate thermoplastic member with at least part of a braided reinforcement structure; and embedding at least the part of the braided reinforcement structure into at least the part of the wall of the elongate shaft member. In some embodiments, the surrounding at least the part of the elongate thermoplastic member with at least the part of the braided reinforcement structure may include weaving the elongate thermoplastic member among braids of the braided reinforcement structure. According to some embodiments, the wall of the elongate shaft member includes a layer including one or more materials provided on top of an outermost surface of the tubular member of the elongate shaft member, and the braided reinforcement structure may not interrupt any exterior surface of the layer and may not interrupt any interior surface of the tubular member.

According to some embodiments, the steerable portion of the elongate shaft member is located between the proximal portion of the elongate shaft member and a distal portion of the elongate shaft member. In some embodiments, the embedded at least the part of the braided reinforcement structure may include a first braided portion including a first pick count. In some embodiments, the first braided portion of the braided reinforcement structure extends along at least part of the proximal portion of the elongate shaft member. In some embodiments, the embedded at least the part of the braided reinforcement structure may include a second braided portion including a second pick count. According to some embodiments, the second braided portion of the braided reinforcement structure may extend along at least part of the distal portion of the elongate shaft member. In some embodiments, the embedded at least the part of the braided reinforcement structure may include a third braided portion including a third pick count that is greater than each of the first pick count and the second pick count. In some embodiments, the third braided portion of the braided reinforcement structure may extend along at least part of the steerable portion of the elongate shaft member. According to some embodiments, the second pick count may be different than the first pick count.

According to some embodiments, the braided reinforcement structure includes a plurality of filaments, the plurality of filaments braided together to form the braided reinforcement structure, and each of the first braided portion of the braided reinforcement structure, the second braided portion of the braided reinforcement structure, and the third braided portion of the braided reinforcement structure may include a respective portion of each filament of the plurality of filaments. In some embodiments, a first ring is incorporated in the proximal portion of the elongate shaft member, and a second ring is incorporated in the distal portion of the elongate shaft member. According to some embodiments, the method includes directly fixedly connecting at least some filaments of the plurality of filaments of the braided reinforcement structure to the first ring, and directly fixedly connecting at least some filaments of the plurality of filaments of the braided reinforcement structure to the second ring. In some embodiments, each filament of the plurality of filaments is a metallic filament, and each of the first ring and the second ring is a metallic ring, and the directly fixedly connecting the at least some filaments to the first ring may include welding each filament of the at least some of the filaments to the first ring, and the directly fixedly connecting at least some of the filaments to the second ring may include welding each filament of the at least some filaments to the second ring.

According to some embodiments, the embedded at least the part of the braided reinforcement structure may be circumferentially arranged about a central longitudinal axis of the elongate shaft member, the central longitudinal axis extending between the proximal portion of the elongate shaft member and the distal portion of the elongate shaft member.

According to some embodiments, the embedding at least the part of the braided reinforcement structure into the at least the part of the wall of the elongate shaft member may include embedding the first portion of the braided reinforcement structure in at least a first polymer portion of the wall of the elongate shaft member, the first polymer portion including a first hardness; embedding the second braided portion of the braided reinforcement structure in at least a second polymer portion of the wall of the elongate shaft member, the second polymer portion including a second hardness; and embedding the third braided portion of the braided reinforcement structure in at least a third polymer portion of the wall of the elongate shaft member, the third polymer portion including a third hardness. In some embodiments, each of the first hardness and the second hardness may be harder than the third hardness. In some embodiments, the first hardness may be harder than the second hardness.

According to some embodiments, the heating at least the part of the elongate thermoplastic member to change the at least the amorphous state of the first portion of the elongate thermoplastic member to the semi-crystalline state may cause at least a portion of the braided reinforcement structure to embed into at least the first portion of the elongate thermoplastic member to restrict at least axial movement of the elongate thermoplastic member, the axial movement in a direction parallel to a central longitudinal axis of the elongate shaft member. According to some embodiments, the heating at least the part of the elongate thermoplastic member to change the at least the amorphous state of the first portion of the elongate thermoplastic member to the semi-crystalline state may cause each of the first braided portion of the braided reinforcement structure and the second braided portion of the braided reinforcement structure to embed deeper into at least the first portion of the elongate thermoplastic member than the third braided portion of the braided reinforcement structure.

According to some embodiments, the part of the braided reinforcement structure is a first part of the braided reinforcement structure, and the method may include providing the steerable catheter with an actuator; incorporating at least a portion of a steering member into at least a portion of the wall of the elongate shaft member, the steering member operatively coupled to the actuator to cause deflection of at least the steerable portion; and surrounding at least part of the steering member with at least a second part of the braided reinforcement structure. In some embodiments, the method may include incorporating a steering ring into at least a second portion of the wall of the elongate shaft member; providing the at least the second part of the braided reinforcement structure radially exterior, with respect to a central longitudinal axis of the elongate shaft member, of at least a region of the steering ring; and directly fixedly connecting the steering member to the steering ring. In some embodiments, the steering member is a metallic steering member, and the steering ring is a metallic steering ring, and the directly fixedly connecting the steering member to the steering ring may include welding the metallic steering member to the metallic steering ring. In some embodiments, the directly fixedly connecting the steering member to the steering ring may be performed through an opening defined by braids of the braided reinforcement structure.

According to some embodiments, the steerable portion of the elongate shaft member is located between the proximal portion of the elongate shaft member and a distal portion of the elongate shaft member. In some embodiments, the embedded at least the part of the braided reinforcement structure may include a first braided portion including a first pick count. In some embodiments, the first braided portion of the braided reinforcement structure extends along at least part of the proximal portion of the elongate shaft member. According to some embodiments, the embedded at least the part of the braided reinforcement structure may include a second braided portion including a second pick count. In some embodiments, the second braided portion of the braided reinforcement structure extends along at least part of the distal portion of the elongate shaft member. According to some embodiments, the embedded at least the part of the braided reinforcement structure may include a third braided portion including a third pick count that is greater than each of the first pick count and the second pick count. In some embodiments, the third braided portion of the braided reinforcement structure extends along at least part of the steerable portion of the elongate shaft member. According to some embodiments, the method may include providing the steerable catheter with an actuator; incorporating at least a portion of a steering member into at least a first portion of the wall of the elongate shaft member, the steering member operatively coupled to the actuator to cause deflection of at least the steerable portion; and surrounding at least part of the steering member with at least part of the second braided portion of the braided reinforcement structure. In some embodiments, at least the part of the second braided portion of the braided reinforcement structure is a first part of the second braided portion of the braided reinforcement structure, and the method may include incorporating a steering ring into at least a second portion of the wall of the elongate shaft member; surrounding the steering ring with at least a second part of the second braided portion of the braided reinforcement structure; and directly fixedly connecting the steering member to the steering ring through an opening defined by braids of at least the second part of the second braided portion of the braided reinforcement structure. In some embodiments, the steering member is a metallic steering member, and the steering ring is a metallic steering ring, and the directly fixedly connecting the steering member to the steering ring through the opening defined by braids of the at least the second part of the second braided portion of the braided reinforcement structure may include welding the metallic steering member to the metallic steering ring through the opening defined by braids of the braided reinforcement structure.

According to some embodiments, the wall of the elongate shaft member includes a layer including one or more materials provided on top of an outermost surface of the tubular member of the elongate shaft member, and the embedded at least the part of the braided reinforcement structure may be distanced from (a) an exterior surface of the layer, and (b) an interior surface of the tubular member. In some embodiments, the wall of the elongate shaft member may include the tubular member of the elongate shaft member.

According to some embodiments, at least the first portion of the elongate thermoplastic member including the amorphous state may include a polyaryletherketone (PAEK) polymer. In some embodiments, the polyaryletherketone (PAEK) polymer may be polyether ether ketone (PEEK).

According to some embodiments, the heating at least the part of the axially adjacent elongate thermoplastic member at least to change the amorphous state of the at least the first portion of the elongate thermoplastic member to the semi-crystalline state may occur during the embedding at least the part of the elongate thermoplastic member into the at least the part of the wall of the elongate shaft member.

According to some embodiments, the embedding at least the part of the elongate thermoplastic member into the at least the part of the wall of the elongate shaft member may include positioning one or more polymer materials in proximity to the elongate thermoplastic member, and the method may include heating the one or more polymer materials to reflow and encapsulate at least part of the elongate thermoplastic member. In some embodiments, the heating the one or more polymer materials to reflow and encapsulate at least the part of the elongate thermoplastic member causing the heating at least the part of the elongate thermoplastic member to change the amorphous state of the at least the first portion of the elongate thermoplastic member to the semi-crystalline state.

According to some embodiments, the embedding at least the part of the elongate thermoplastic member into the at least the part of the wall of the elongate shaft member may include reflowing one or more polymer materials over at least the tubular member. In some embodiments, the heating at least the part of the axially adjacent elongate thermoplastic member at least to change the amorphous state of the at least the first portion of the elongate thermoplastic member to the semi-crystalline state occurs during the reflowing the one or more polymer materials over the at least the tubular member.

According to some embodiments, the semi-crystalline state, to which the amorphous state of the at least the first portion of the elongate thermoplastic member is changed by the heating, is a first semi-crystalline state. In some embodiments, the elongate thermoplastic member may concurrently include with the first portion of the elongate thermoplastic member, a second portion including a second semi-crystalline state in which the second portion of the elongate thermoplastic member includes a greater degree of crystallinity than the first portion of the elongate thermoplastic member including the amorphous state. In some embodiments, the second portion of the elongate thermoplastic member may occupy at least in part, a different axial region of the elongate thermoplastic member than the first portion of the elongate thermoplastic member along a length of the elongate thermoplastic member. In some embodiments, the first portion of the elongate thermoplastic member may be positioned to extend through at least part of the proximal portion of the elongate shaft member when at least the part of the elongate thermoplastic member is embedded in at least the part of the wall of the elongate shaft member, and the second portion of the elongate thermoplastic member may be positioned to extend through at least part of the steerable portion of the elongate shaft member when at least the part of the elongate thermoplastic member is embedded in at least the part of the wall of the elongate shaft member. In some embodiments, the method may include surrounding both the first portion of the elongate thermoplastic member and the second portion of the elongate thermoplastic member with a braided reinforcement structure. In some embodiments, the heating at least the part of the axially adjacent elongate thermoplastic member to change at least the amorphous state of the first portion of the elongate thermoplastic member to the first semi-crystalline state may cause the braided reinforcement structure to embed deeper into the first portion of the elongate thermoplastic member than into the second portion of the elongate thermoplastic member.

Various methods in other embodiments may include combinations and sub-combinations of the methods described above.

Various embodiments of the present invention may include systems, devices, or machines that are or include combinations or subsets of any one or more of the systems, devices, or machines and associated features thereof summarized above or otherwise described herein.

Further, all or part of any one or more of the systems, devices, or machines summarized above or otherwise described herein or combinations or sub-combinations thereof may implement or execute all or part of any one or more of the processes or methods described herein or combinations or sub-combinations thereof.

All or part of any one or more of the systems, devices, or machines summarized above or otherwise described herein or combinations or sub-combinations thereof may be produced at least in part by any one or more of the manufacturing processes or methods described herein or combinations or sub-combinations thereof.

It should be noted that various embodiments of the present invention include variations of the methods or processes summarized above or otherwise described herein (including the figures) and, accordingly, are not limited to the actions described or shown in the figures or their ordering, and not all actions shown or described are required, according to various embodiments. According to various embodiments, such methods may include more or fewer actions and different orderings of actions. Any of the features of all or part of any one or more of the methods or processes summarized above or otherwise described herein (including the figures) may be combined with any of the other features of all or part of any one or more of the methods or processes summarized above or otherwise described herein or shown in the figures.

Further, any of all or part of one or more of the methods or processes and associated features thereof discussed herein may be implemented or executed on or by all or part of a device system, apparatus, or machine, such as all or a part of any of one or more of the systems, apparatuses, or machines described herein or a combination or sub-combination thereof.

BRIEF DESCRIPTION OF THE DRAWINGS

It is to be understood that the attached drawings are for purposes of illustrating aspects of various embodiments and may include elements that are not to scale.

DETAILED DESCRIPTION

Figure 1:
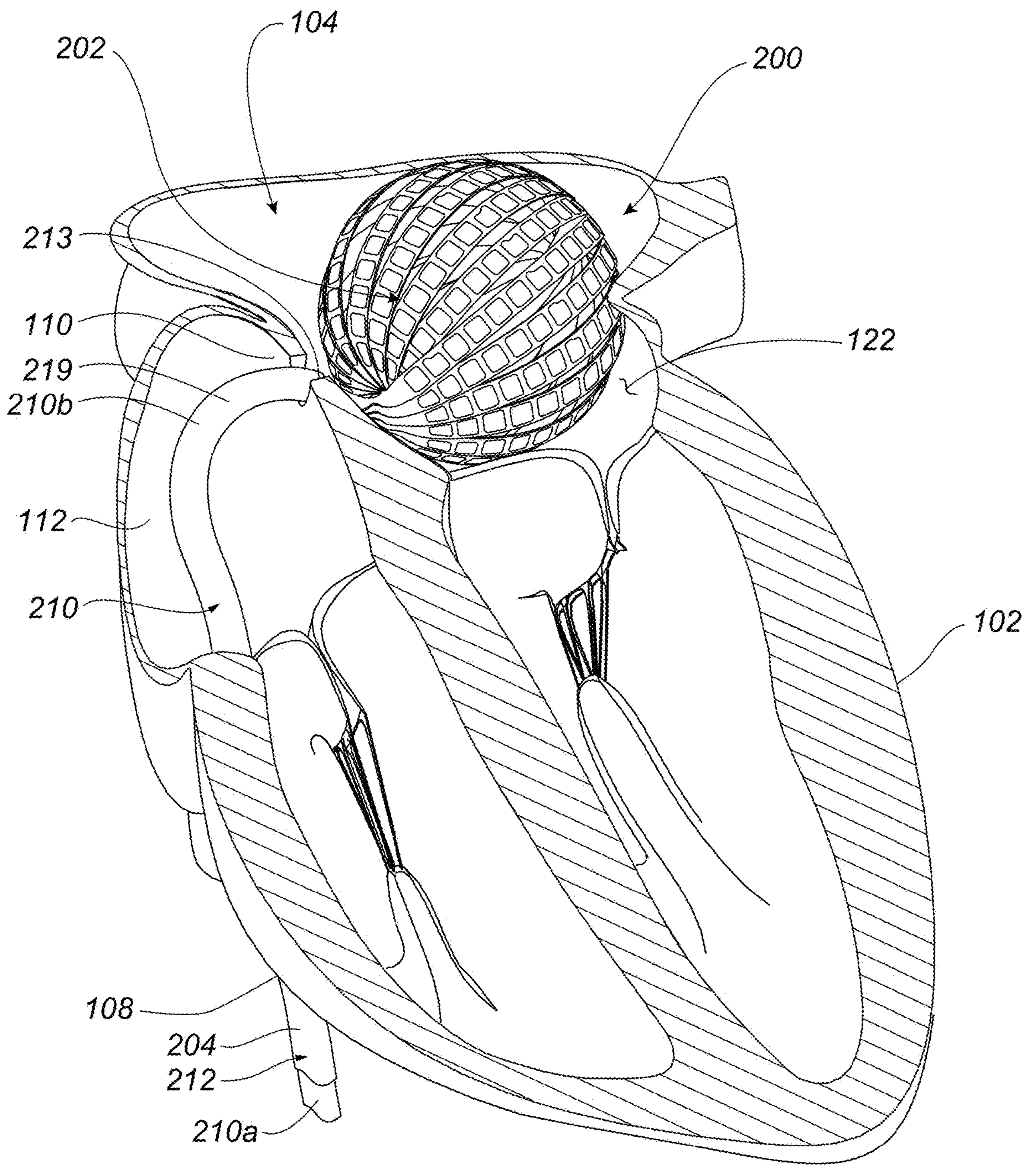
FIG. 1 is a cutaway diagram of a heart showing a medical system including an elongate shaft member coupled to an expandable structure percutaneously placed in a left atrium of the heart, according to various example embodiments.

Various embodiments disclosed herein provide improved medical device systems that include various axial members within an elongate shaft member of a medical device (e.g., a steerable catheter). At least some of these and other embodiments allow, e.g., the steerable catheter to exhibit improved bendability and positioning with respect to particular anatomical features that improves desired placement of an operative structure delivered by the elongate shaft member within a bodily cavity to treat the bodily cavity. At least some of these and other embodiments allow, e.g., the catheter to retain a desired diameter of the elongate shaft member that is suitable at least for percutaneous delivery, while maintaining safety of operation. It should be noted that the invention is not limited to these or any other examples provided herein, which are referred to for purposes of illustration only.

In the following description, certain specific details are set forth in order to provide a thorough understanding of various embodiments of the invention. However, one skilled in the art will understand that the invention may be practiced at a more general level without one or more of these details. In other instances, well-known structures (e.g., structures associated with medical systems and catheters) have not been shown or described in detail to avoid unnecessarily obscuring descriptions of various embodiments of the invention.

Any reference throughout this specification to "one embodiment" or "an embodiment" or "an example embodiment" or "an illustrated embodiment" or "a particular embodiment" and the like means that a particular feature, structure or characteristic described in connection with the embodiment is included in at least one embodiment. Thus, any appearance of the phrase "in one embodiment" or "in an embodiment" or "in an example embodiment" or "in this illustrated embodiment" or "in this particular embodiment" or the like in this specification is not necessarily referring to one embodiment or a same embodiment. Furthermore, the particular features, structures or characteristics of different embodiments may be combined in any suitable manner to form one or more other embodiments.

Unless otherwise explicitly noted or required by context, the word "or" is used in this disclosure in a non-exclusive sense. In addition, unless otherwise explicitly noted or required by context, the word "set" is intended to mean one or more, and the word "subset" is intended to mean a set having the same or fewer elements of those present in the subset's parent or superset.

Further, the phrase "at least" is or may be used herein at times merely to emphasize the possibility that other elements may exist besides those explicitly listed. However, unless otherwise explicitly noted (such as by the use of the term "only") or required by context, non-usage herein of the phrase "at least" nonetheless includes the possibility that other elements may exist besides those explicitly listed. For example, the phrase 'based at least on A' includes A as well as the possibility of one or more other additional elements besides A. In the same manner, the phrase 'based on A' includes A, as well as the possibility of one or more other additional elements besides A. However, the phrase 'based only on A' includes only A. Similarly, the phrase 'configured at least to A' includes a configuration to perform A, as well as the possibility of one or more other additional actions besides A. In the same manner, the phrase 'configured to A' includes a configuration to perform A, as well as the possibility of one or more other additional actions besides A. However, the phrase 'configured only to A' means a configuration to perform only A.

The word "device", the word "machine", and the phrase "device system" all are intended to include one or more physical devices or sub-devices (e.g., pieces of equipment) that interact to perform one or more functions, regardless of whether such devices or sub-devices are located within a same housing or different housings. However, it may be explicitly specified that a device or machine or device system resides entirely within a same housing to exclude embodiments where the respective device, machine, or device system resides across different housings. The word "device" may equivalently be referred to as a "device system".

Further, the phrase "in response to" may be used in this disclosure. For example, this phrase might be used in the following context, where an event A occurs in response to the occurrence of an event B. In this regard, such phrase includes, for example, that at least the occurrence of the event B causes or triggers the event A.

In some embodiments, the term "adjacent", the term "proximate", or the like refers at least to a sufficient closeness between the objects defined as adjacent, proximate, or the like, to allow the objects to interact in a designated way. For example, if object A performs an action on an adjacent or proximate object B, objects A and B would have at least a sufficient closeness to allow object A to perform the action on object B. In this regard, some actions may require contact between the associated objects, such that if object A performs such an action on an adjacent or proximate object B, objects A and B would be in contact, for example, in some instances or embodiments where object A needs to be in contact with object B to successfully perform the action. In some embodiments, the term "adjacent", the term "proximate", or the like additionally or alternatively refers to objects that do not have another substantially similar object between them. For example, object A and object B may be considered adjacent or proximate in some embodiments if they contact each other (and, thus, it may be considered that no other object is between them), or if they do not contact each other but no other object that is substantially similar to object A, object B, or both objects A and B, depending on the embodiment, is between them. In some embodiments, the term "adjacent", the term "proximate", or the like additionally or alternatively refers to at least a sufficient closeness between the objects defined as adjacent, proximate, or the like, the sufficient closeness being within a range that does not place any one or more of the objects into a different or dissimilar region, or does not change an intended function of any one or more of the objects or of an encompassing object that includes a set of the objects. Different embodiments of the present invention adopt different ones or combinations of the above definitions. Of course, however, the term "adjacent", the term "proximate", or the like is not limited to any of the above example definitions, according to some embodiments. In addition, the term "adjacent" and the term "proximate" do not have the same definition, according to some embodiments.

The term "proximal", in the context of a proximal portion, proximal location, and the like of a medical device, includes, for example, the portion, location, and the like, being or being configured to be further away from a patient or portion of or region within a patient (e.g., a bodily cavity) intended to be treated or assessed by the medical device, as compared to a distal portion, location, and the like of the medical device, according to some embodiments. In some embodiments, the term "proximal", in the context of a proximal portion, proximal location, and the like of a medical device, includes, for example, the portion, location, and the like, being or being configured to be delivered (e.g., percutaneously or intravascularly) toward a patient or portion of or region within a patient (e.g., a bodily cavity) intended to be treated or assessed by the medical device, after or behind a distal portion, location, and the like of the medical device. On the other hand, the term "distal", in the context of a distal portion, distal location, and the like of a medical device, includes, for example, the portion, location, and the like, being or being configured to be closer to a patient or portion of or region within a patient (e.g., a bodily cavity) intended to be treated or assessed by the medical device, as compared to a proximal portion, location, and the like of the medical device, according to some embodiments. In some embodiments, the term "distal", in the context of a distal portion, distal location, and the like of a medical device, includes, for example, the portion, location, and the like, being or being configured to be delivered (e.g., percutaneously or intravascularly) toward a patient or portion of or region within a patient (e.g., a bodily cavity) intended to be treated or assessed by the medical device, before or ahead of a proximal portion, location, and the like of the medical device.

The phrase "bodily opening" as used in this disclosure should be understood to include, for example, a naturally occurring bodily opening or channel or lumen; a bodily opening or channel or lumen or perforation formed by an instrument or tool using techniques that can include, but are not limited to, mechanical, thermal, electrical, chemical, and exposure or illumination techniques; a bodily opening or channel or lumen formed by trauma to a body; or various combinations of one or more of the above. Various elements having respective openings, lumens or channels and positioned within the bodily opening (e.g., a catheter sheath or catheter introducer) may be present in various embodiments. These elements may provide a passageway through a bodily opening for various devices employed in various embodiments.

The phrase "bodily cavity" as used in this disclosure should be understood to mean a cavity in a body. The bodily cavity may be a cavity provided in a bodily organ (e.g., an intra-cardiac cavity or chamber of a heart). The bodily cavity may be provided by a bodily vessel.

FIG. 1 is a medical system 200 including an expandable structure 202 percutaneously or intravascularly placed in a left atrium 104 of a heart 102, according to some embodiments. In some embodiments, the medical system 200 may be considered a steerable catheter. Expandable structure 202 can be percutaneously or intravascularly inserted into a portion of the heart 102, such as an intra-cardiac cavity, like left atrium 104. In this example, the expandable structure 202 is physically coupled to an end of an elongate shaft member 210 inserted via the inferior vena cava 108 and penetrating through a bodily opening in transatrial septum 110 from right atrium 112. In other embodiments, other paths may be taken. In some embodiments, the elongate shaft member 210 may be part of a steerable catheter. The elongate shaft member 210 is flexible and appropriately sized to be delivered, at least in part, percutaneously or intravascularly, according to various embodiments. In some embodiments, at least part of the elongate shaft member 210 is delivered though a natural bodily opening. Various portions of elongate shaft member 210 may be steerable, such as in some embodiments in which the medical system 200 is a steerable catheter.

According to some embodiments, the elongate shaft member 210 may be or include either or both of a shaft **210*a* and a sheath 210*b*, where, in some embodiments, the expandable structure 202 is physically coupled to at least part of a distal end portion of the shaft 210*a* for percutaneous delivery by the shaft 210*a* through the sheath 210*b*. In some embodiments, expandable structure 202 assumes an unexpanded configuration for delivery to left atrium 104, e.g., when being percutaneously delivered to the left atrium 104 through the sheath 210*b*. Expandable structure 202 can then be selectively expanded upon delivery to left atrium 104 to position certain portions of the expandable structure 202 proximate the interior surface formed by tissue 122 of left atrium 104 in order to, for example, sense characteristics of, ablate, or otherwise interact with or treat such tissue 122**.

Figures 2A, 2B, 2C:
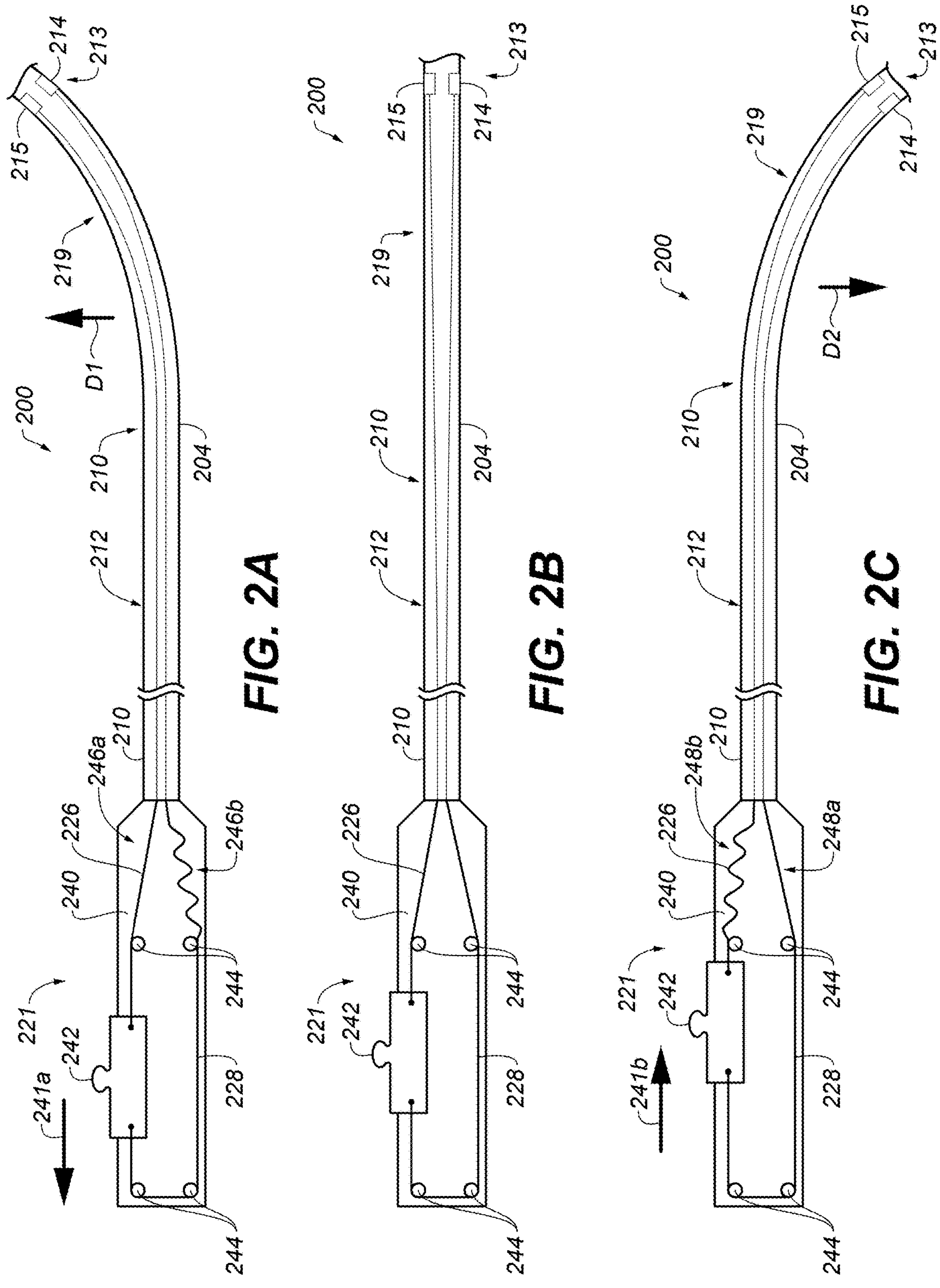
FIGS. 2A, 2B, and 2C show at least part of a medical system including an elongate shaft member in various bending or deflection configurations under control of an actuator device system of the medical system, according to some embodiments.

FIGS. 2A-2C shows portions of elongate shaft member 210 illustrated within a broader medical system 200, according to some example embodiments. In some embodiments, the medical system 200 may be or be considered all or a portion of a steerable catheter. In some embodiments, elongate shaft member 210 is elongate and flexible, and includes a circumferential wall 204 (e.g., an outer, exterior, or external wall, such as an outer, exterior, or external wall of the sheath 210*b* shown more particularly in FIG. 1). Elongate shaft member 210 includes a proximal portion 212 and a distal portion 213. In some embodiments, expandable structure 202 (not shown in FIGS. 2A-2C, but shown at least in FIG. 1) may be physically coupled to at least a portion of the distal portion 213. For example, in some embodiments in which the elongate shaft member 210 includes the shaft 210*a* and the sheath 210*b* (shown at least in FIG. 1), the expandable structure 202 may be physically coupled to a distal end or distal end portion of the shaft 210*a*.

In various embodiments, the elongate shaft member 210 is arranged to be delivered (e.g., percutaneously, intravascularly, or through a natural bodily opening) to a bodily cavity or organ with the distal portion 213 positioned to be delivered ahead of the proximal portion 212. In some embodiments, the elongate shaft member 210 is configured such that at least a part of the proximal portion 212 is located outside of a body when the distal portion 213 is delivered to a desired destination within the body (e.g., in an organ such as the atrium of a heart). In various embodiments, the elongate shaft member 210 includes a steerable portion 219 between the proximal portion 212 and the distal portion 213. In various embodiments, the elongate shaft member 210 is configured to be deliverable (e.g., percutaneously, intravascularly) at least partially through a bodily opening leading to a bodily cavity or organ with the distal portion 213 ahead of the steerable portion 219, and the steerable portion 219 ahead of the proximal portion 212. In some embodiments, the elongate shaft member 210 is configured such that at least a part of the proximal portion 212 is located outside of a body when the steerable portion 219 is delivered to a desired destination within the body (e.g., in an organ such as the atrium of a heart). In various embodiments, elongate shaft member 210 includes at least one lumen therein (e.g., extending between the proximal portion 212 and the distal portion 213). In some embodiments, elongate shaft member 210 is a hollow shaft member or a tubular shaft member, such as in embodiments where the sheath 210*b*, the shaft 210*a*, or both each include at least one lumen.

Figure 3:
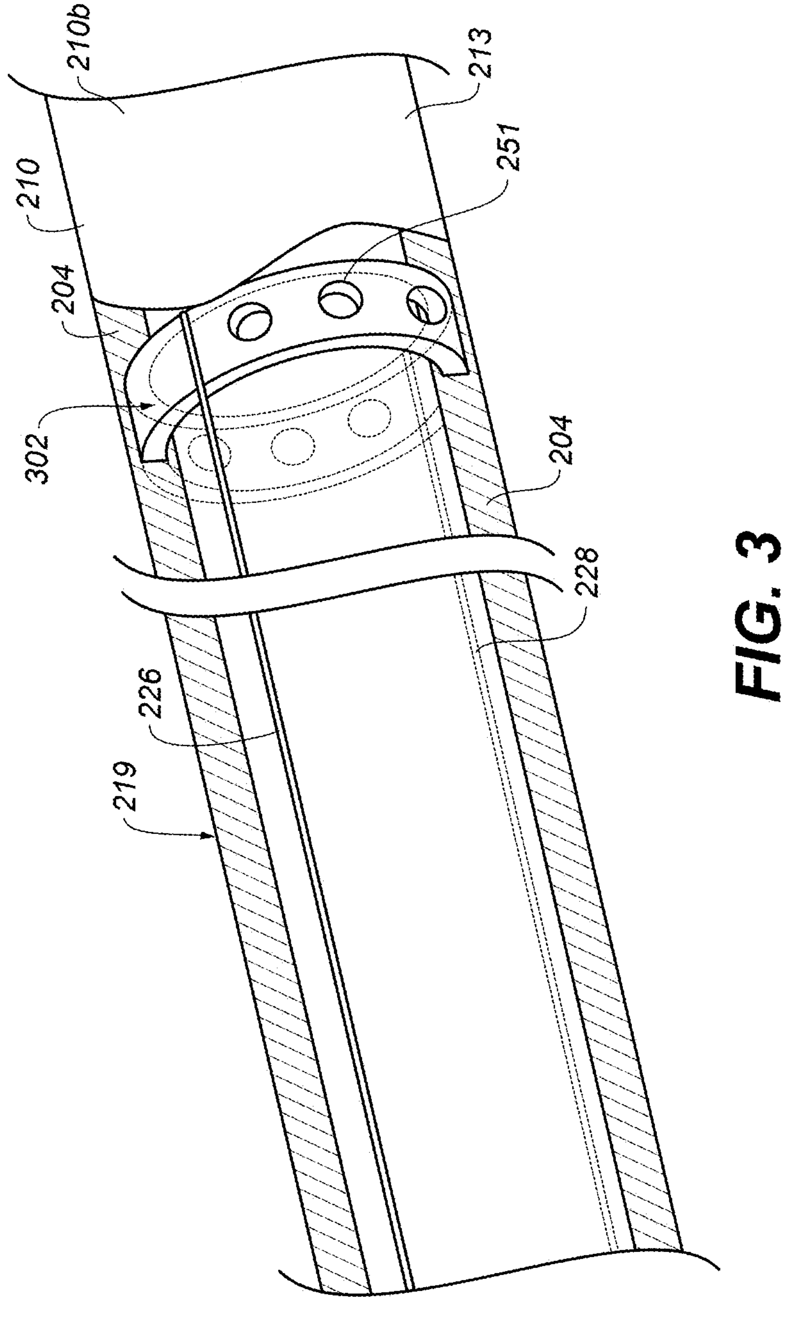
FIG. 3 is partial section view of an elongate shaft member of a medical system, according to some embodiments.

In some embodiments, the proximal portion 212 of the elongate shaft member 210 extends to a handle portion 221 of the steerable catheter. According to various embodiments, the handle portion 221 is configured to be gripped or otherwise directly manipulated by a user (e.g., a health care practitioner) during manipulation of the catheter in a particular operation (e.g., a diagnostic or treatment procedure). FIGS. 2A-2C illustrate some embodiments of at least part or at least some aspects of the handle portion 221. In various embodiments, an actuator or actuator set, such as actuator device system 240, according to some embodiments, is located at least proximate the proximal portion 212 and is operatively coupled to the steerable portion 219 to transmit force thereto to steer or deflect at least the steerable portion 219. In some embodiments, the actuator or actuator set (such as actuator device system 240) is located, at least in part on or in the handle portion 221. In some embodiments, the distal portion 213 is also steered or deflected with the steerable portion 219. According to various embodiments, the actuator or actuator set (e.g., described below with respect to at least actuator device system 240, according to some embodiments) is operatively coupled to at least the steerable portion 219 by one or more axial members configured to transmit force to particular parts of the elongate shaft member 210 to cause deflection of the at least the steerable portion 219 in a first particular plane. In some embodiments, these axial members are also known as steering members. For example, reference is made to the partial sectional view of FIG. 3, which may represent a portion of the sheath 210*b* of elongate shaft member 210, according to some embodiments. As shown in FIG. 3, according to some embodiments, the elongate shaft member 210 may include a steering member set, including steering member 226 and steering member 228, coupled to the actuator or actuator set (e.g., actuator device system 240 in FIGS. 2A, 2B, and 2C, according to some embodiments) to transmit force to particular parts of the elongate shaft member 210 to cause deflection of the at least the steerable portion 219 in a first particular plane. In some embodiments, each of the steering member 226 and the steering member 228 may include a respective steering line or cable disposed within a respective tubular member that is provided within (e.g., within the wall 204, according to some embodiments, of) the elongate shaft member 210. In some embodiments, each tubular member includes a low friction material (e.g., polytetrafluoroethylene (PTFE)) to reduce resistance to movements of the steering member through the tubular member.

Each of the steering members (e.g., steering members 226, 228) may have various material compositions, according to various embodiments. For example, in some embodiments, various ones of the steering members (e.g., steering members 226, 228) may be made from various suitable cable materials including various polymers (e.g., various thermoplastics) or metallic materials (e.g., stainless steel). The various steering members (e.g., steering members 226, 228) may be terminated at, secured, or fastened or attached to respective ones of securing portions 214, 215 (shown, e.g., in at least FIGS. 2A-2C, according to some embodiments) of the elongate shaft member 210 by various techniques including the use of mechanical fasteners, knots, bonding employing various adhesives, welding, and combinations thereof. To minimize the overall size requirements of the elongate shaft member 210, techniques that generally produce a lower-profile or smaller securing joint are generally preferred. In this regard, in various embodiments, various steering members (e.g., steering members 226, 228) may be directly fixedly connected to respective ones of securing portions 214, 215 (shown, e.g., in at least FIGS. 2A-2C, according to some embodiments) of the elongate shaft member 210. In some embodiments, a direct connection is a connection between objects that does not involve connection devices, such as clamps or fasteners, such as screws or pins. In some embodiments, direct connection techniques may include welding, soldering, and adhesive bonding. In some embodiments, a direct connection (such as the above-mentioned direct, fixed connection between a steering member and a securing portion) is a low-profile connection that does not increase, or does not substantially increase, a dimension of the directly connected objects, such as a width dimension or a height dimension along an axis transverse or at least oblique to a longitudinal axis of the directly connected objects. For example, such a height dimension may, in some embodiments, be in a stacked direction, such as in a radial direction radiating from central longitudinal axis 230 (described in more detail below) or from inner-, interior-, or internal-most location 231 (also described in more detail below), and such a width dimension may, in some embodiments, be transverse to the height dimension. In various embodiments, a direct connection such as the above-mentioned direct, fixed connection between two objects such as the steering member and the securing portion described above, may have height dimension along a radial direction of the cross-section of the elongate shaft member that is not greater, or is only marginally greater than a combined height of the two objects along the radial direction of the cross-section of the elongate shaft member.

In various embodiments, a fixed connection is configured to resist axial forces (and in some embodiments, lateral loads) that are, e.g., transmitted by the actuator or actuator set (e.g., actuator device system 240) via the steering member without causing separation from the connected securing portion. In various embodiments, fixed connections are configured to resist moments or couples that are, e.g., caused by forces transmitted by the actuator or actuator set 221 via the steering member to prevent rotation or peeling of the steering member away from the connected securing portion. It is noted that, in many cases, the steering members 226, 228 and securing portions 214, 215 are incorporated into at least part of a wall (e.g., wall 204) of the elongate shaft member 210 by particular techniques which may include melting polymer thereover to form the part of the wall. These particular techniques are not considered to provide a direct fixed connection, much less any connection at all, but rather, are configured to be wall forming techniques distinct from directly fixedly connecting the steering members (e.g., steering members 226, 228) to the securing portion(s) (e.g., respective securing portions 214, 215). In this regard, in some embodiments, it may be important to allow portions of each steering member 226, 228 to translate within the wall 204 of the elongate shaft member 210, further illustrating that mere embedding of the steering members 226, 228 along with securing portions 214, 215 into the wall 204 is not considered directly fixedly connecting the steering members 226, 228 to the respective securing portions 214, 215.

In various embodiments, the overall cross-sectional size of the elongate shaft member 210 is generally desired to be as small as possible when employed as a catheter required to be delivered through restrictive bodily openings (e.g., various vascular passages). In this regard, direct fixed connections typically require minimal space requirements. In some embodiments, a steering ring (e.g., such as ring 302 in some embodiments) is disposed in (e.g., within or, in some embodiments, inward from an outer, exterior, or external surface of) the elongate shaft member 210, for example, as shown in FIG. 3. In some embodiments, the steering ring is disposed in (e.g., within or, in some embodiments, inward from) the wall 204 of the elongate shaft member 210. Advantageously, in some embodiments, the steering ring is disposed within the wall 204 of the elongate shaft member 210 so as to provide additional structural support to the wall 204 and to allow for a reduced size or dimension (e.g., thickness, diameter or circumference) of elongate shaft member 210, as compared to, for example, some embodiments where the steering ring (e.g., such as ring 302 in some embodiments) is disposed radially inward from the wall 204. In some embodiments, the steering ring 302 provides termination portions for one or more of the steering members (e.g., steering members 226, 228). However, in some embodiments, the steering ring 302 need not terminate one or more of the steering members 226, 228, and may merely act as a pass-through for one or more of the steering members 226, 228 on their way to termination portions or locations. According to some embodiments, the steering ring 302 may be a particular embodiment of securing portions 214, 215. In some embodiments, one or more of the steering members 226, 228 continue to extend beyond the securing portions 214, 215. In some embodiments, the steering ring (e.g., steering ring 302) is a metallic (e.g., stainless steel) ring. In some embodiments, the steering ring is arranged or configured to have a closed form (e.g., a closed continuous ring). For example, in some embodiments, the steering ring is a continuous closed ring, with notches or slots formed therein along the longitudinal direction of the elongate shaft member 210 that do not entirely sever the steering ring, in which at least part of the steering members (e.g., steering members 226, 228) are welded or adhered (to form, for example, a direct fixed connection). In some embodiments, the steering ring (e.g., such as ring 302 in some embodiments) includes slots along the longitudinal direction of the elongate shaft member 210 that entirely sever the steering ring, in which at least part of the steering members (e.g., steering members 226, 228) are welded or adhered. In some of these embodiments, the welding or adhering of the steering members (e.g., steering members 226, 228) fills the slots and, therefore, the steering ring may still be considered a continuous closed ring. In some embodiments, the steering ring is arranged or configured to have an open form (e.g., an open ring including one or more complete interruptions that respectively prevent a path that extends around the entirety of the ring). It is noted that an open ring that includes multiple complete interruptions may essentially include a plurality of separate components. These separate components may include one or more spaces therebetween but are considered to still form part of a ring when positioned in a ring-like configuration or constrained by at least part of the elongate shaft member 210 to maintain a ring-like configuration. For example, steering ring (e.g., such as ring 302 in some embodiments) may include two spaced apart portions, the two spaced apart portions maintained by the elongate shaft member 210 in a spatial orientation that defines a ring-like shape from the two portions. In some embodiments where the steering ring acts as a pass-through for one or more of the steering members, the one or more steering members may pass through one or more of the spaces or gaps formed by such spaced-apart portions. Further, although FIG. 3 illustrates only a single steering ring 302, multiple steering rings may be present, some of which may allow one or more steering members to pass through, and some of which may act as a termination portion for one or more of the steering members. FIGS. 4D and 4E, discussed in more detail below, illustrate embodiments of rings 301, 302 where axial members, including steering members 226, 228 merely pass along the top (radially outward) of the rings 301, 302, for example, although such steering members 226, 228 may still be directly fixedly connected to such rings 301, 302, e.g., by welding, in some embodiments.

In some embodiments, the elongate shaft member 210 is produced, at least in part, by welding the steering members (e.g., steering members 226, 228) to the steering ring (e.g., such as ring 302 in some embodiments), as shown, for example, in FIG. 3, and at least part of the wall 204 of the elongate shaft member 210 is formed around the steering members (e.g., steering members 226, 228) and the ring 302 by melting a polymer (e.g., polyurethane, polyethylene, PEBA (e.g., PEBAX 3533, 7233), and Nylon 12 (e.g., VESTAMID) embodiments). PEBAX is a registered Trademark of ARKEMA FRANCE CORPORATION FRANCE 420 Rue d'Estienne d'Orves 92700 Colombes FRANCE. VESTAMID is a registered Trademark of EVONIK DEGUSSA GMBH CORPORATION FED REP GERMANY RELLINGHAUSER STRASSE 1-11 ESSEN FED REP GERMANY 45128. Openings 251 (one called out in FIG. 3) in the steering ring 302 provide regions that may be filled by such polymer during the melting process to facilitate integral formation of the wall 204 and the steering ring 302, according to some embodiments. In some embodiments, the steering ring (e.g., such as ring 302 in some embodiments) is disposed at or proximate the steerable portion 219 of the elongate shaft member 210. In some embodiments, the steering ring is disposed between the steerable portion 219 of the elongate shaft member 210 and the distal portion 213 of the elongate shaft member 210. In some embodiments, the steering ring is disposed at or proximate the distal portion 213 of the elongate shaft member 210.

As described above, the steering members 226, 228 may be operatively coupled to the steering ring (e.g., such as ring 302 in some embodiments) to cause selective bending of steerable portion 219, according to various embodiments. With reference to FIGS. 2A, 2B, and 2C, there is shown the elongate shaft member 210 in various bending or deflection configurations. Operation of one or more of the steering members 226, 228, attached to respective securing portions 214, 215, contributes to elongate shaft member 210 bending or deflecting at least steerable portion 219. Such control via one or more of the steering members 226, 228 provides the ability to efficiently move elongate shaft member 210 and, for example, expandable structure 202, through a bodily opening providing a passageway (e.g., an artery), and accurately position expandable structure 202 within a bodily cavity (e.g., an atrium of a heart). Operation of the steering members 226, 228 may be accomplished via use of an actuator device, such as actuator device system 240, which is provided, for example, and are based at least in part on teachings from FIGS. 15*a*, 15*b*, and 15*c* of U.S. U.S. Pat. No. 5,715,817, issued Feb. 10, 1998, to Stevens-Wright et al.

In some embodiments, the steerable portion 219 is positioned proximal (e.g., toward the proximal portion 212 of elongate shaft member 210) at least securing portions 214, 215 of the elongate shaft member 210, where the steering members 226, 228 are connected. According to various embodiments, securing portions 214, 215 are portions of the steerable catheter to which the distal parts of the steering members 226, 228 are physically connected and which are configured to generate a reactionary mechanical couple or moment in response to axial forces applied via the steering members, the reactionary mechanical couple or moment causing deflection of at least the steerable portion 219. In some embodiments, the steerable portion 219 is positioned proximal (e.g., toward the proximal portion 212 of elongate shaft member 210) steering ring (e.g., such as ring 302 in some embodiments).

In some embodiments, the elongate shaft member 210, by way of the various configurations of the various embodiments of the present invention, permits opposing movement of the steering member 226 and the steering member 228 to bend or deflect at least the steerable portion 219 of the elongate shaft member 210 in a first direction D1 of two opposing directions within a first plane (e.g., the plane of the sheet of FIGS. 2A, 2B, and 2C), and permits opposing movement of the steering member 226 and the steering member 228 to bend or deflect at least the steerable portion 219 of the elongate shaft member 210 in a second opposite direction D2 of the two opposing directions within the first plane (for example, as shown in FIGS. 2A and 2C). In some embodiments, the elongate shaft member 210 permits concurrent opposing movement of steering member 226 and steering member 228 to bend or deflect at least the steerable portion 219 of the elongate shaft member 210 in a first direction D1 of two opposing directions within a first plane, and permits concurrent opposing movement of steering member 226 and steering member 228 to bend or deflect the steerable portion 219 of the elongate shaft member 210 in a second opposite direction D2 of the two opposing directions within the first plane. According to various embodiments, bending or deflecting at least the steerable portion 219 of the elongate shaft member 210 in the first and second directions D1 and D2 may occur in a single plane and may be referred to as bidirectional bending.

Operation of the steering members 226, 228 to bend or deflect at least the steerable portion 219 of the elongate shaft member 210 may involve releasing tension in one of steering members 226, 228 and increasing tension (e.g., in a concurrent manner or a sequential manner) in the other of the steering members 226, 228, according to some embodiments. Additionally or alternatively, operation of the steering members 226, 228 to bend or deflect at least the steerable portion 219 of the elongate shaft member 210 may involve playing out or moving at least part of one of the steering members 226, 228 distally (e.g., in a direction from the proximal portion 212 of the elongate shaft member 210 toward the distal portion 213 of the elongate shaft member 210) and taking up or moving (e.g., in a concurrent manner or a sequential manner) at least part of the other of the steering members 226, 228 proximally (e.g., in a direction from the distal portion 213 of the elongate shaft member 210 toward the proximal portion 212 of the elongate shaft member 210). In this regard, the steering members 226, 228 may act as tendons, with bending or deflecting of at least the steerable portion 219 occurring in the direction toward the particular one of the steering members 226, 228 that at least (a) undergoes increased tension levels or (b) is taken up. It is noted, according to some embodiments, that the other one of the steering members 226, 228 that at least (c) undergoes decreased tension levels or (d) is played out, does so at least in order to not restrain or hinder the steerable portion 219 of the elongate shaft member 210 from bending or deflecting in the direction toward the particular one of steering members 226, 228 that is undergoing increased tension levels or is taken up.

Various one or more actuators may be employed to cause operation of the steering members 226, 228 to bend or deflect at least the steerable portion 219 of the elongate shaft member 210 in each of direction D1 and D2 or in each of two directions or vectors in a first plane. By way of non-limiting example, FIGS. 2A, 2B, and 2C (collectively FIG. 2) are schematic representations of an actuator device system 240 (also called an actuator, actuator set, control device, or control device system) coupled to the elongate shaft member 210 and operable for bending or deflecting at least part (e.g., steerable portion 219) of the elongate shaft member 210 in two directions within a first plane (e.g., a single plane) by manipulation of two steering members (e.g., steering members 226, 228 in FIGS. 2A, 2B, and 2C, according to some embodiments). Since the present invention is not limited to any particular technique for causing push/pull or take-up/play-out movement of steering members, FIG. 2 are provided as an example based in part on FIGS. 15*a*, 15*b*, and 15*c* of U.S. Pat. No. 5,715,817, issued Feb. 10, 1998, to Stevens-Wright et al., known in the art.

In various embodiments associated with FIGS. 2, manipulation of the steering members 226, 228 may occur concurrently. In FIGS. 2, each of the steering members 226, 228 is terminated, secured, connected, or fastened to respective ones of securing portions 214, 215 of the elongate shaft member 210. Additionally, the steering members 226, 228 are each terminated, secured, connected, or otherwise fastened to slider 242 of actuator set 240. Various guides 244 may be provided to guide steering members 226, 228 to their respective termination locations on slider 242, according to various embodiments. Slider 242 is guided by a guide system (such as a track or rail, according to some embodiments) to move in various directions (e.g., first direction 241*a* in FIG. 2A and second direction 241*b* in FIG. 2C). In some embodiments, movement of slider 242 may occur in response to direct manipulation thereof by a user. In some embodiments, movement of slider 242 may occur in response to operation of an electric motor or other actuator including pneumatic and hydraulic actuators. FIG. 2B shows slider 242 in an initial or ready position corresponding to a state before an actuated bending or deflection of steerable portion 219 of elongate shaft member 210. In the state of FIG. 2B, substantially equal levels of tension may be provided in the steering members 226, 228, such that no force differential or an insufficient force differential is applied by the steering members 226, 228 to securing portions 214, 215 to noticeably bend or deflect at least the steerable portion 219 predominately in one of the two directions D1 and D2. In some embodiments, however, a default tension level differential may be applied in the neutral actuator state to the steering members 226, 228 to cause a default force differential sufficient to bias steerable portion 219 to bend in a particular one of the two directions D1 and D2 by an initial or default amount when the slider 242 is positioned in the ready position. In FIG. 2A, slider 242 has been moved along first direction 241*a* and has increased tension (e.g., represented by a relatively straight member form 246*a*) in steering member 226 while concurrently reducing tension (e.g., represented by the exaggerated wiggly member form 246*b*) in steering member 228 to bend steerable portion 219 in the direction D1. In FIG. 2C, slider 242 has been moved along second direction 241*b* and has increased tension (e.g., represented by a relatively straight line form 248*a*) in steering member 228 while concurrently reducing tension (e.g., represented by the exaggerated wiggly line form 248*b*) in steering member 226 to bend steerable portion 219 in the direction D2. Other embodiments may employ other actuation systems to selectively bend or deflect at least the steerable portion 219 of the elongate shaft member 210 in either of directions D1 and D2.

Figure 4A:
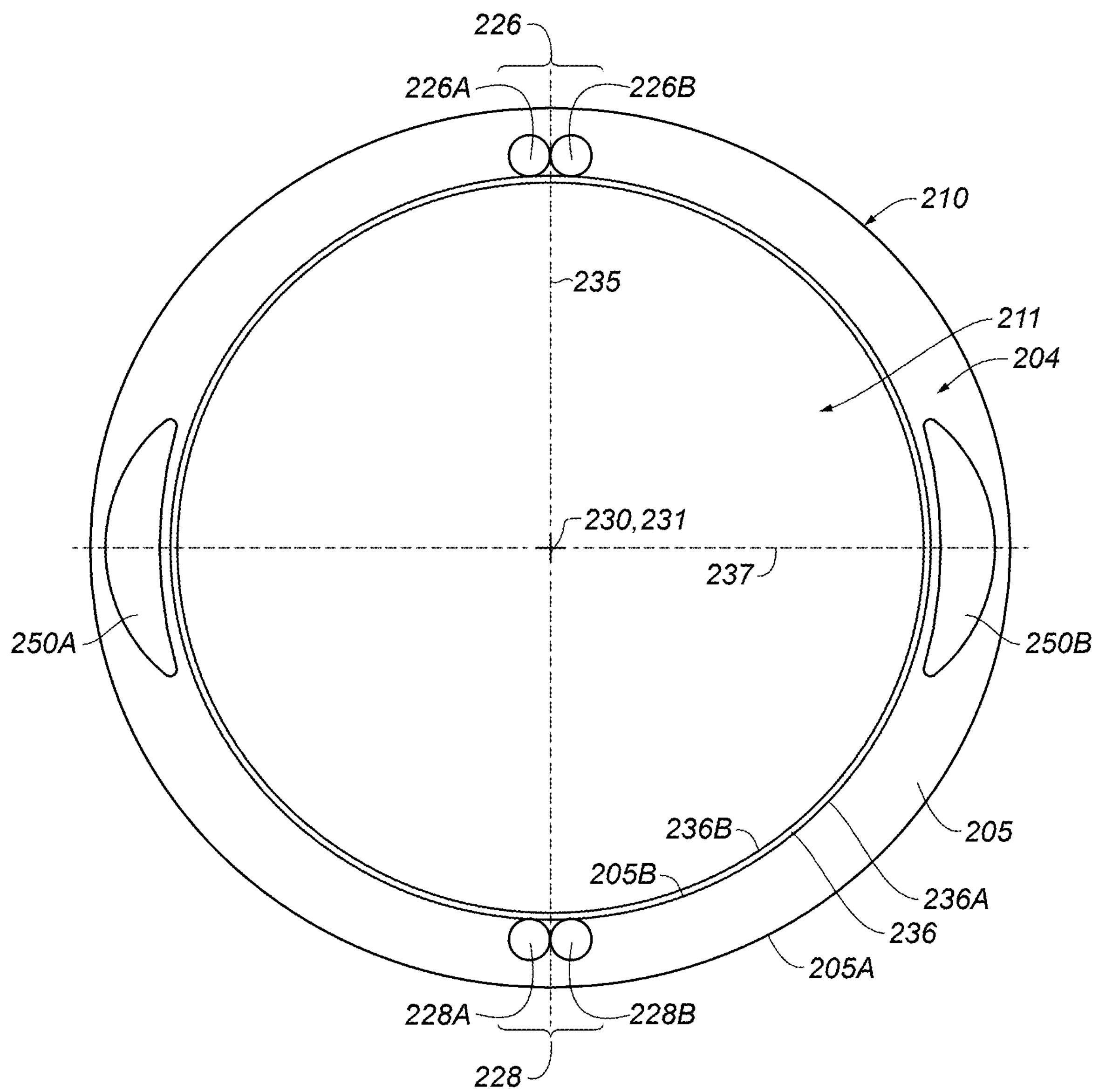
FIG. 4A is a cross-sectional view of an elongate shaft member of a medical system at a steerable portion of the elongate shaft member, according to some embodiments.

FIG. 4A is a cross-sectional view of the elongate shaft member 210 at steerable portion 219 of the elongate shaft member 210, according to some embodiments. It is noted that a same or similar cross-sectional view as that shown in FIG. 4A may occur at other points along the length of elongate shaft member 210. According to some embodiments, steering member 226 is provided by a set of steering members 226A, 226B, and steering member 228 is provided by a set of steering members 228A, 228B. Having steering member 226, steering member 228, or each of steering members 226, 228 take the form of a set of multiple steering members may be motivated by various reasons, including by way of non-limiting example, the use of smaller sized wires that, in number provide sufficient strength, but with a lower profile. Regardless, it is noted that, in some embodiments in which the set of multiple steering members 226A, 226B function as a single steering member 226 (for example, as described above), such set of multiple steering members may, therefore, be considered to be a single steering member, according to some embodiments. The same applies, for example, with the set of multiple steering members 228A, 228B, according to some embodiments. By way of non-limiting example, other cross-sectional shapes including rectangular, square, oval, and elliptical may be employed by various ones of the steering members 226, 228 or individual steering members 226A, 226B, 228A, 228B thereof.

According to some embodiments, the steering members 226, 228 are disposed at opposite sides of the cross-section of the elongate shaft member 210, about an inner-, interior-, or internal-most location 231 within the elongate shaft member 210. According to some embodiments, the elongate shaft member 210 may include a central longitudinal axis (e.g., central longitudinal axis 230), and the inner-, interior-, or internal-most location 231 within the elongate shaft member 210 may be a location in the cross-sectional view of the elongate shaft member 210 intersected by the central longitudinal axis 230, according to some embodiments. Accordingly, in some embodiments, the location of the inner-, interior-, or internal-most location 231 may also correspond to the location of the longitudinal axis 230 with the understanding that the longitudinal axis 230 extends into and out of the plane of the sheet of FIG. 4A. Central longitudinal axis 230 may extend between the proximal portion 212 and the distal portion 213 of the elongate shaft member 210 and through a geometric center or centroid of each of one or more or all cross-sections of the elongate shaft member 210, according to some embodiments. As used herein, according to some embodiments, the phrase, longitudinal axis of the elongate shaft member 210, has the meaning of an axis along the lengthwise direction or vector of the elongate shaft member 210. As described above, portions of the elongate shaft member 210 may be bent during use. In such cases, as used herein according to some embodiments, the longitudinal axis 230 would bend in a manner corresponding to any bending of the elongate shaft member 210. In some embodiments, the inner-, interior-, or internal-most location 231 within the elongate shaft member 210 in the plane of a cross-section of an axial member (e.g., an axial member being or including steering members 226, 228, or axial members 250A, 250B described in more detail below) within the elongate shaft member 210 is a centroid of a cross-section of the elongate shaft member 210 in the plane of the cross-section of the axial member. In some embodiments, the inner-, interior-, or internal-most location 231 within the elongate shaft member 210 in the plane of a cross-section of such an axial member is a centroid of a cross-section of a tubular member or tubular layer (e.g., all or a layer portion of the wall 204) of the elongate shaft member 210 in the plane of the cross-section of the axial member.

In FIG. 4A, the steering members 226, 228, and the individual steering members thereof 226A, 226B, 228A, 228B, according to some embodiments, are angularly spaced about and radially spaced from inner-, interior-, or internal-most location 231. It is noted, according to various embodiments, that the individual steering members 226A, 226B, 228A, 228B may each be contained in a respective lumen. In some embodiments, various ones of these respective lumens may be sized and dimensioned to allow movement or translation of the steering member within the lumen to, for example, impart a bending force in the elongate shaft member 210 at least as described above. Each of the lumens may be provided in various manners. In some embodiments, small tubular members made from a low friction material (e.g., polytetrafluoroethylene (PTFE), according to some embodiments) are molded within at least part of the elongate shaft member 210 to provide various ones the respective lumens that enclose, surround, or provide passageways for various ones of the steering members, such as individual steering members 226A, 226B, 228A, 228B.

In some embodiments, elongate shaft member 210 is or includes a tubular member. In some embodiments, the wall 204 of the elongate shaft member 210 is arranged in a tubular configuration and may be considered a tubular member of the elongate shaft member 210. According to some embodiments, the wall 204 of the elongate shaft member 210 is provided at least in part by a tubular member of the elongate shaft member. In some embodiments, elongate shaft member 210 includes one or more lumens extending between the proximal portion 212 and distal portion 213 of the elongate shaft member 210. In the example cross-sectional view of elongate shaft member 210 in FIG. 4A, the elongate shaft member 210 includes a lumen 211, according to various embodiments. In some embodiments, the elongate shaft member 210 is an elongate sheath that includes a lumen 211 sized and dimensioned to selectively allow passage of a medical instrument therethrough during percutaneous or intravascular delivery of the medical instrument along a path through the lumen 211. In some embodiments, the medical instrument includes an expandable structure (e.g., expandable structure 202). In some embodiments, the elongate shaft member 210 including lumen 211 is physically coupled to an expandable structure (e.g., expandable structure 202). For example, the elongate shaft member 210 including lumen 211 may form at least the shaft 210*a* of a medical instrument (e.g., a diagnostic or treatment catheter).

In various embodiments, elongate shaft member 210 may include various layers. In some embodiments, the various layers are arranged in a concentric arrangement. In FIG. 4A, a low friction material layer 236 (e.g., a polytetrafluoroethylene (PTFE) layer) is employed, according to various embodiments. The use of a material layer such as layer 236 may be motivated for different reasons. For example, a low friction material layer, such as layer 236, may be appropriately located in elongate shaft member 210 to facilitate movement of a particular element (e.g., a medical instrument) through a lumen provided in elongate shaft member 210. According to some embodiments, layer 236 may be considered a tubular layer of the elongate shaft member 210. According to some embodiments, layer 236 may be considered to be a tubular member, or at least a tubular layer of a tubular member, of the elongate shaft member 210. Various layers made from metallic or non-metallic materials may be incorporated into elongate shaft member 210, according to various embodiments. In some of these various embodiments, some of these layers may be reinforcement layers or backing layers for other layers or components provided within elongate shaft member 210.

As described above according to some embodiments, the catheter may include a first steering member 226 (which may include, e.g., steering sub-members 226A, 226B) and a second steering member 228 (which may include, e.g., steering sub-members 228A, 228B). An actuator set 240 may be configured to manipulate the first steering member, the second steering member, or both the first steering member and the second steering member, to cause bending or deflection of at least the steerable portion 219 in a first particular plane. In FIG. 4A, the first particular plane is represented by broken line 235, which extends between first steering member 226 and second steering member 228. It is understood that broken line 235 represents the first particular plane as viewed on edge. According to various embodiments, the force vectors created by the steering members lie on the first particular plane between the two steering members. In some embodiments, each of the first steering member 226 and the second steering member 228 includes a respective axis extending between the actuator set 240 and the steerable portion 219. In some embodiments, the axis of the first steering member 226 and the axis of the second steering member 228 lie in the first particular plane.

Various spatial relationships between the steering members 226, 228 may be employed, according to various embodiments. For example, with reference to FIG. 4A, the steering members 226, 228 may be arranged in certain configurations within (e.g., within wall 204 of) elongate shaft member 210. For example, in some embodiments, the steering members 226, 228 are angularly spaced about and radially spaced from the inner-, interior-, or internal-most location 231 within the elongate shaft member 210, (e.g., as viewed along the longitudinal axis 230) with at least an angular spacing between the first steering member 226 and the second steering member 228 being approximately 180 degrees.

Various problems can occur when actuator set 240 applies force via one or both of steering members 226, 228 to cause bending or deflection of at least the steerable portion 219 of the elongate shaft member 210 in the first particular plane (e.g., represented by broken line 235 at least in FIG. 4A). For example, an undesired lateral bending or deflection of the at least the steerable portion 219 of the elongate shaft member 210 may occur during deflection in the first particular plane. This undesired lateral bending or deflection may occur for different reasons. For example, manufacturing deviations may create cross-sectional variabilities along at least part of the length of the at least the steerable portion 219 of the elongate shaft member 210, which increase a propensity of the steerable portion 219 to laterally deflect under the application of tensile forces via a steering member (e.g., 226 or 228). Undesired lateral deflection may also occur if the steering members 226, 228 are not properly axially aligned within the elongate shaft member 210 as they extend between the actuator set 240 and the steerable portion 219. If a steering member (e.g., 226 or 228) extends along even a minor or shallow helical path between actuator set 240 and steerable portion 219, forces imparted via the steering member may lead to a movement that can result in the undesired lateral deflection.

Other undesired effects can occur when actuator set 240 applies force via one or both of steering members 226, 228 to cause bending or deflection of at least the steerable portion 219 of the elongate shaft member 210 in the first particular plane. For example, a tensile force applied by a steering line (e.g., 226 or 228) during bending or deflection of at least the steerable portion 219 may cause the elongate shaft member 210 to compress or shorten by an undesired amount. When this occurs, a distal end portion of the elongate shaft member 210 may not be at an expected position or location after the bending or deflection of the at least the steerable portion 219 of the elongate shaft member 210. The present inventors have, in some instances, encountered approximately 5 mm to 10 mm of shortening during deflection of catheters having elongate shaft member outer, exterior, or external diameters of approximately 7 mm. In applications in which the catheter is employed to position a medical instrument or an implant at a desired location in the body, such shortening of the catheter during deflection is counter to positional accuracy. It is noted that that this shortening effect is more prominent with catheters having relatively smaller diameters and with catheters having relatively longer lengths.

According to some embodiments of the present invention, the above-discussed undesired out-of-plane bending and undesired catheter shortening may be reduced due at least to axial member 250A, axial member 250B, or both axial members 250A, 250B shown at least in FIG. 4A. In this regard, in some embodiments, the cross-section of the elongate shaft member 210 shown in FIG. 4A includes an axial member set made up of one or more axial members (e.g., a group of axial members, according to some embodiments associated with FIG. 4A). In FIG. 4A, the elongate shaft member 210 includes an axial member 250A, according to some embodiments, and an axial member 250B, according to some embodiments. According to some embodiments, at least part of each axial member 250A, 250B is incorporated into the elongate shaft member 210. According to some embodiments, at least part of each axial member is incorporated into a wall (e.g., wall 204) of the elongate shaft member 210.

According to some embodiments, an axial member such as axial member 250A or 250B may be employed to mitigate, alleviate, or reduce the undesired effects associated with improper deflection and shortening of the at least the steerable portion 219 of the elongate shaft member 210 (for example, the undesired effects described above). In this regard, according to some embodiments, axial members such as axial members 250A, 250B act as strengthening members or stiffening members employed to alleviate or reduce various problems such as, but not limited to, undesired lateral deflection during steering or undesired compressive shortening during steering. Various considerations should be taken into account when axial members (e.g., 250A, 250B) are employed as strengthening members or stiffening members. In some embodiments, these axial members should provide, according to some embodiments, (a) sufficient lateral stiffness, or (b) sufficient compressive stiffness, or both (a) and (b) while minimizing increases to the overall diameter of the elongate shaft member 210 or unduly increasing the forces required to steer at least the steerable portion 219 of the elongate shaft member 210.

In general, the outer, exterior, or external dimension (e.g., outer, exterior, or external diameter) of the elongate shaft member 210 is usually determined by the thickest member incorporated into (e.g., into wall 204 of) the elongate shaft member 210. According to some embodiments, the maximum thickness (e.g., thickness in a radial direction in the cross-section of the elongate shaft member 210 shown in FIG. 4A) of the cross-section of the axial members 250A, 250B is chosen to be similar to, or the same as, the thickness of the steering members 226 or 228. However, it is noted that reducing the thickness of the axial members 250A, 250B can reduce their resistance to compressive loading. According to some embodiments, providing axial member 250A, 250B with a curved cross-sectional form to conform to constraints of wall 204 would also reduce or maintain the outer, exterior, or external dimension of the elongate shaft member 210 within desired limits. One such embodiment is exemplified in FIG. 4A.

The compressive strength of each axial member (e.g., 250A, 250B) is related to the cross-sectional area of the axial member. It is desirable, according to some embodiments, to increase the cross-sectional area of the axial member to allow the elongate shaft member 210 to withstand compressive forces produced by tension in the steering members 226 or 228 without significant compressive shortening. It is noted that compressive strength is not materially affected by the shape of the axial member (e.g., 250A, 250B), but rather is more significantly affected by the cross-sectional area of the axial member. According to various embodiments, addressing compressive strength requirements may not be a major factor when choosing the particular cross-sectional shape of the axial member (e.g., 250A or 250B), provided the particular cross-sectional shape has adequate cross-sectional area.

Figure 4B:
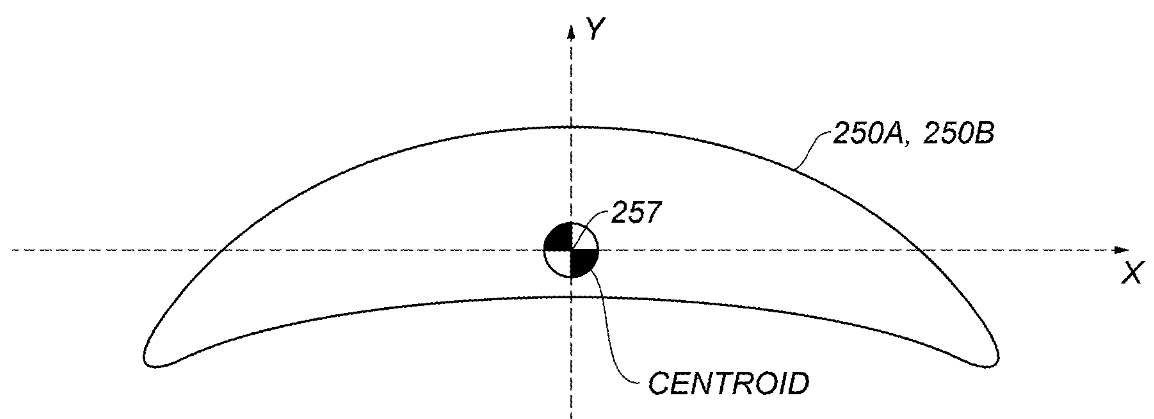
FIG. 4B is a cross-sectional view of an axial member of an elongate shaft member of a medical system, according to some embodiments.

According to some embodiments, the axial member (e.g., 250A, 250B) may require sufficient compressive buckling resistance to prevent buckling failures of the axial member itself under the influence of compressive forces caused by tension in the steering members 226, 228. In some cases, compressive bucking failures may cause the axial member to break, and, in some instances, snap outwardly through the outer, exterior, or external surface of the wall 204 of the elongate shaft member 210. Such instances can pose a safety hazard. Compressive buckling failures may be mitigated in various ways, according to some embodiments. According to some embodiments, various reinforcement structures (e.g., described below at least with respect to FIGS. 4C, 4D, and 4E) may be used to reduce the unsupported length of various parts of the respective axial member (e.g., 250A, 250B) to increase buckling resistance and reduce risk of puncturing of a surface of the wall 204 of the elongate shaft member 210 by an axial member. Compressive bucking resistance is also related to the second moment of area of the cross-section of the axial member (e.g., 250A or 250B). The second moment of area, also known as the moment of inertia, is a geometric property of an area which reflects how its points are distributed with regards to a particular area. For example, FIG. 4B shows an 'X" axis and "Y" axis superimposed on the centroid or geometric center of the cross-sectional shape of the axial member (e.g., axial member 250A or axial member 250B). In this regard, the cross-sectional shape of the axial member would have a second moment of area Ix about the X axis, and a second moment of area Iy about the Y axis. In some embodiments associated with FIG. 4A, the Y axis corresponds to a radial axis in the cross-section of the elongate shaft member 210. Ix is smaller than Iy in various embodiments associated with FIGS. 4A, 4B and, accordingly, there is a propensity for the axial member to buckle in a direction associated with the Y axis radially inward or radially outward in some embodiments. In these particular embodiments, it is noted that increases in Ix can in turn increase the compressive buckling resistance of the axial member. Ix can be increased in various manners. For example, a thickness of the axial member (e.g., in the y direction) can be increased, but this approach may require an undesired increase in an overall dimension (e.g., outside diameter) of the elongate shaft member 210. The curved shape of the cross-sectional shape of the axial member (e.g., 250A or 250B) can also be adjusted to increase the Ix and thus increase compressive buckling resistance. According to some embodiments associated with FIGS. 4A, 4B, the cross-sectional shape of the axial member 250A or 250B is curved radially inward (e.g., toward the inner-, interior-, or internal-most location 231 in the elongate shaft member 210) to increase Ix without unduly increasing the overall dimension (e.g., outer, exterior, or external diameter) of the elongate shaft member 210.

In some embodiments associated with FIG. 4A, a second particular plane (e.g., represented by broken line 237) intersects the cross-section of the elongate shaft member 210, with the central longitudinal axis 230 of the elongate shaft member 210 lying on or in the second particular plane. According to some embodiments, the above-discussed first particular plane in which occurs the deflection of the at least the steerable portion 219 of the elongate shaft member 210 (e.g., such first particular plane represented by broken line 235 in at least FIG. 4A) is non-parallel with the second particular plane (e.g., represented by broken line 237). According to some embodiments, the second particular plane (e.g., represented by broken line 237) intersects the first particular plane (e.g., represented by broken line 235). According to some embodiments, the first particular plane (e.g., represented by broken line 235) and the second particular plane (e.g., represented by broken line 237) are orthogonal planes. According to some embodiments, the first particular plane (e.g., represented by broken line 235) and the second particular plane (e.g., represented by broken line 237) intersect the inner-, interior-, or internal-most location 231 within the elongate shaft member 210 at least in the plane of the cross-section of the elongate member shown in FIG. 4A.

In some embodiments, the second particular plane (e.g., represented by broken line 237) extends between the two axial members 250A and 250B. In some embodiments, the second particular plane (e.g., represented by broken line 237) extends between the respective centroids or geographic centers of the two axial members 250A and 250B. According to various embodiments, a respective axis (e.g., longitudinal axis) of each of a first axial member 250A and the second axial member 250B lie on or in the second particular plane (e.g., represented by broken line 237).

In some embodiments, the catheter (e.g., an example of medical system 200, according to some embodiments) includes a first axial member (e.g., axial member 250A) and second axial member (e.g., axial member 250B), each of the first and second axial members having a respective axis (e.g., a longitudinal axis) extending between the proximal portion 212 of the elongate shaft member 210 and the distal portion 213 of the elongate shaft member 210. In some embodiments, each respective axis (e.g., longitudinal axis) of the first and second axial members intersects the respective centroid or geographic center of the corresponding first axial member (e.g., first axial member 250A) or second axial member (e.g., second axial member 250B). In some embodiments at least in which the steering members 226, 228 are considered axial members, each respective axial-member axis (e.g., longitudinal axis) intersects the respective centroid or geographic center of the assemblage of the sub-members (e.g., 226A, 226B or 228A, 228B) of the corresponding axial member. For example, the respective longitudinal axis of the axial member 226 may pass through the point where the circular cross-sections of the individual sub-members 226A, 226B meet, i.e., the center of the combined cross-sectional areas of the assemblage of the sub-members 226A, 226B.

According to various embodiments, the first axial member (e.g., axial member 250A), the second axial member (e.g., axial member 250B), or each of the first and the second axial members is embedded in (e.g., embedded in wall 204 of) the elongate shaft member 210 to resist axial movement thereof. In some embodiments, an actuator (e.g., of at least part of actuator device system 240) is operatively coupled to the steerable portion 219 to cause deflection of the steerable portion to cause bending or deflection of at least the steerable portion 219 in the first particular plane (e.g., represented by broken line 235 in FIG. 4A) and the first axial member (e.g., axial member 250A), the second axial member (e.g., axial member 250B) or each of the first and the second axial members is configured to resist, at least in part, lateral bending or deflection of the at least the steerable portion 219 away from the first particular plane during the bending or deflection of the at least the steerable portion 219 in the first particular plane.

It is noted that increases in Ix to increase compressive buckling resistance also increase the resistance to at least the steerable portion 219 laterally deflecting away from the first particular plane during the steering thereof. It is noted, however, that, if the axial member (e.g., 250A or 250B) includes an inordinately large Iy (i.e., an inordinately large second moment of area about the y axis), such large Iy may have a significant effect on the bending stiffness of the elongate shaft member 210, and, therefore, may undesirably increase the force required to steer, bend, or deflect at least the steerable portion 219 of the elongate shaft member 210. According to some embodiments, reduction of this adverse impact on the steering force may be accomplished by reducing Iy. According to some embodiments, the cross-sectional shape of the axial member (e.g., 250A or 250B) is bent or curved inwardly (e.g., in a direction toward the inner-, interior-, or internal-most location 231 of the elongate shaft member 210) to reduce Iy (e.g., by reducing an overall dimension of the cross-sectional shape of the axial member along the x axis). It is noted that this bent or curved form also increases Ix (e.g., by increasing an overall dimension of the cross-sectional shape of the axial member along the y axis) and increases the compressive buckling resistance provided by the axial member. Accordingly, adjusting the cross-sectional shape of the axial member (e.g., 250A or 250B) as per the various embodiments and factors described herein can help to improve compressive strength, compressive buckling resistance, and resistance to lateral deflection during steering, while avoiding an increase in the overall outer, exterior, or external dimensions of the elongate shaft member 210. It is noted however, that various embodiments are not limited to the particular shapes of the axial members 250A, 250B shown in FIG. 4A. Various other shapes may be employed by other axial members employed as strengthening members or stiffening members to alleviate or reduce problems, such as the aforementioned lateral deflection and compression shortening. By way of non-limiting example, other cross-sectional shapes including rectangular, square, oval, and elliptical may be employed by various ones of the axial members 250A, 250B, according to various example embodiments.

Figure 4C:
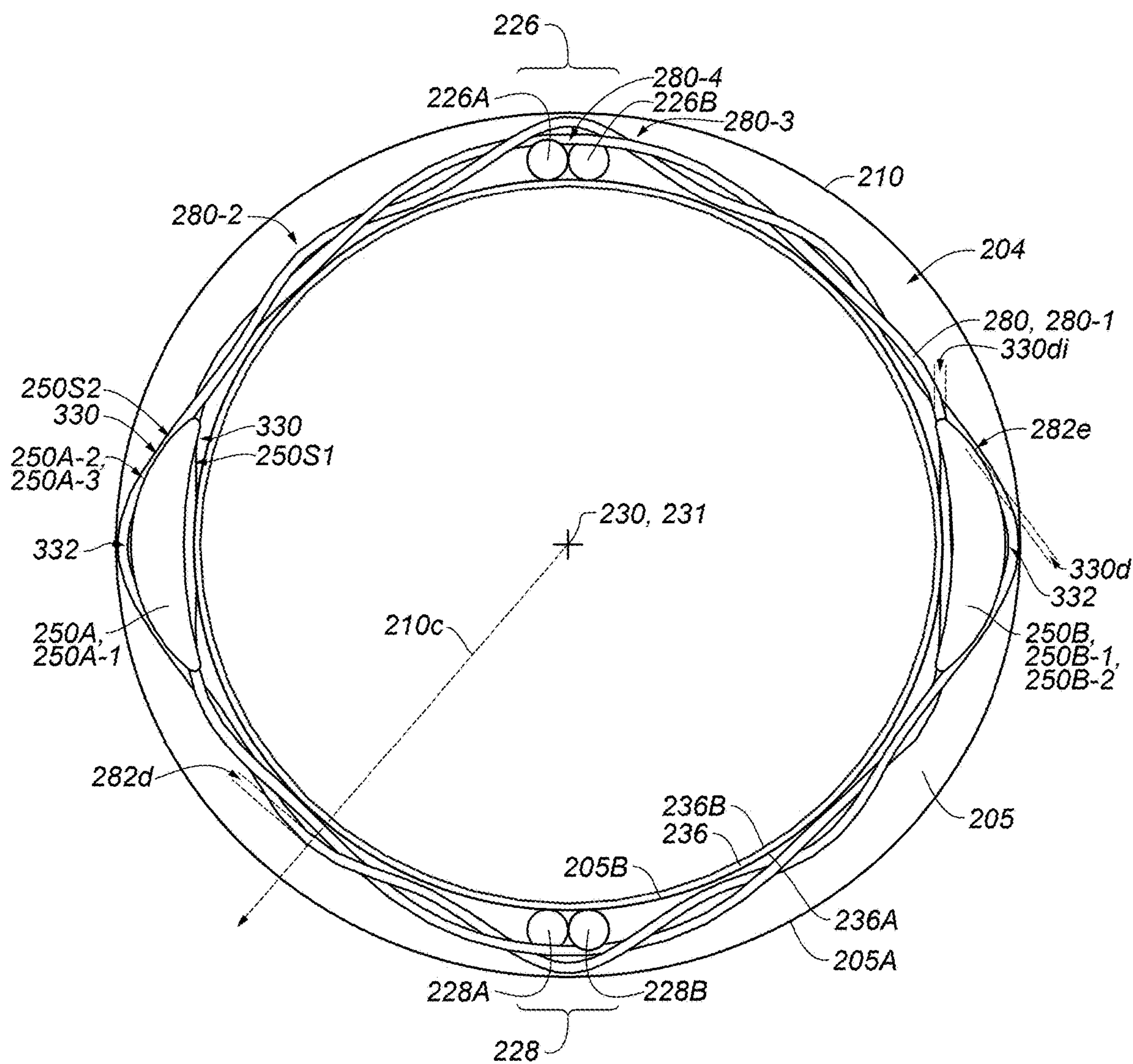
FIG. 4C is a partial cross-sectional view of an elongate shaft member of a medical system, the elongate shaft member including a reinforcement structure, according to some embodiments.
Figure 4D:
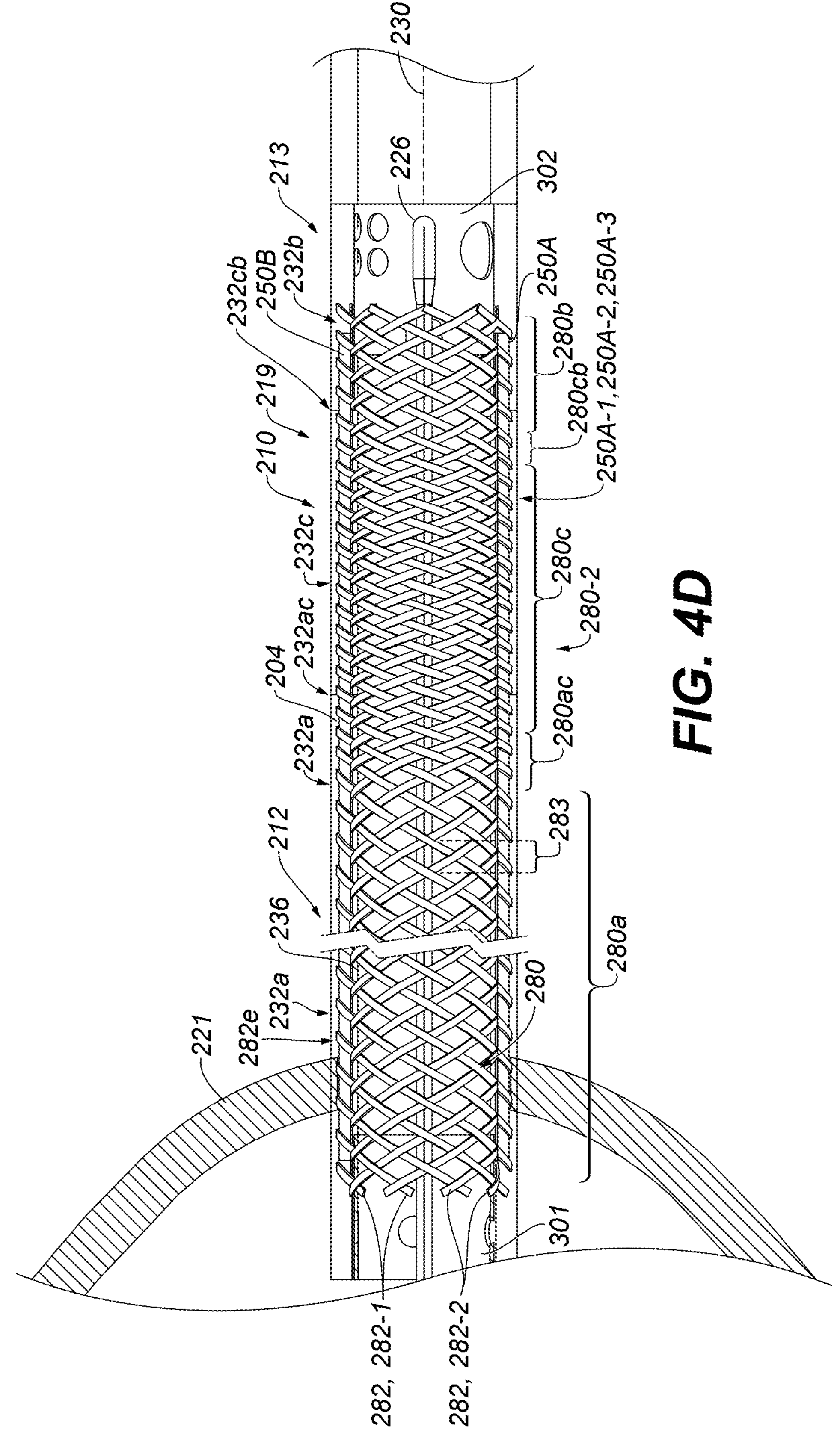
FIG. 4D is a partial cross-sectional view of an elongate shaft member and a handle portion of a medical system, the elongate shaft member including a reinforcement structure, according to some embodiments.
Figure 4E:
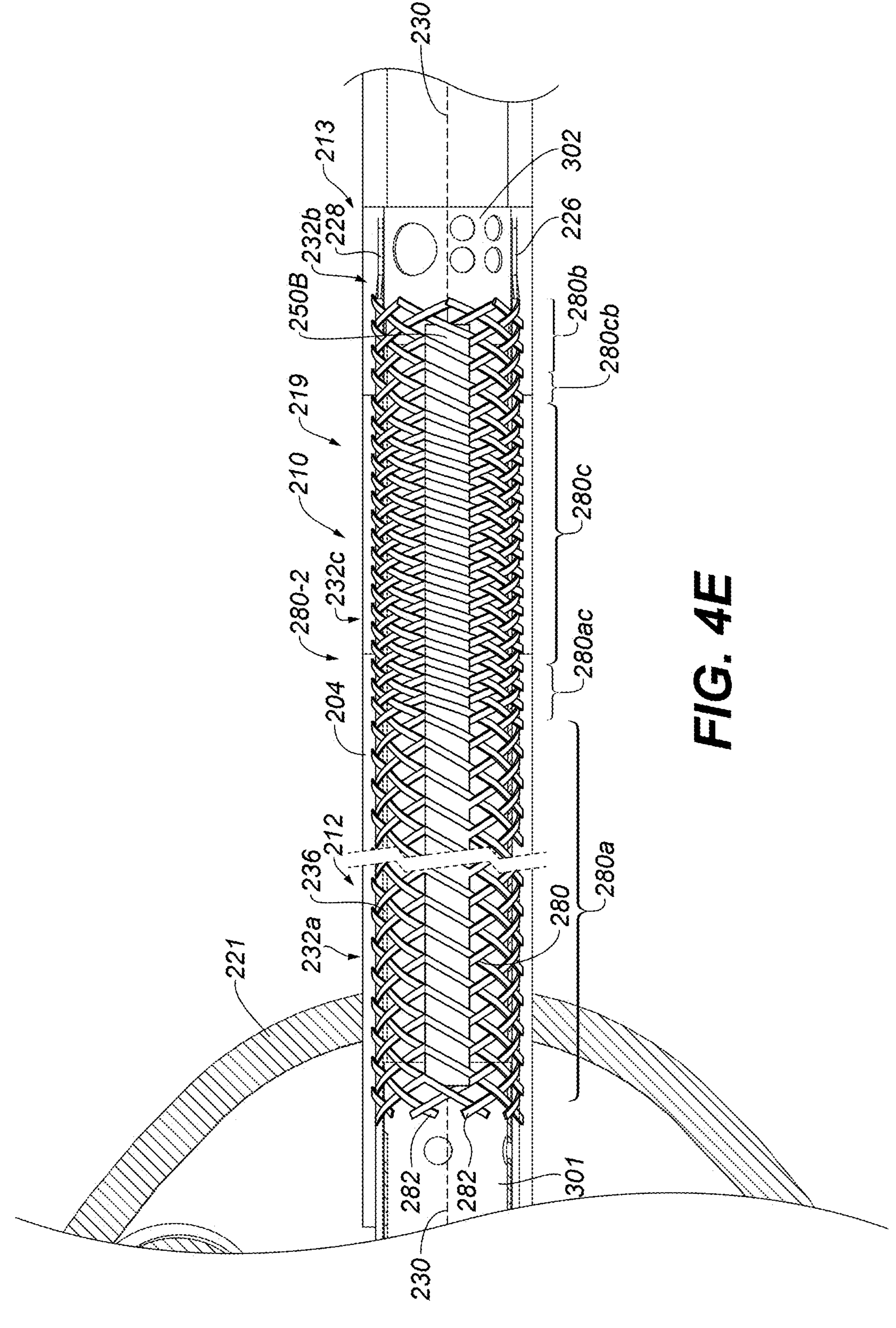
FIG. 4E is a partial cross-sectional view of an elongate shaft member and a handle portion of a medical system, the elongate shaft member including a reinforcement structure, according to some embodiments.

According to some embodiments, the elongate shaft member 210 includes a reinforcement structure, at least a first portion of the reinforcement structure surrounding at least a respective portion of each of the axial members (e.g., first axial member 250A and second axial member 250B). For example, FIG. 4C illustrates a partial cross-sectional view through a longitudinal portion of an embodiment of elongate shaft member 210 including axial members 250A and 250B similar to that shown in FIG. 4A, but with the addition of a reinforcement structure 280. In some embodiments, at least a second portion of the reinforcement structure 280 surrounds at least a respective portion of each of the first steering member 226 and the second steering member 228. In this regard, "surrounds" may, in some embodiments and contexts, include that, for example, one or more portions of the reinforcement structure 280 is radially exterior of (e.g., further outside of, further exterior than, or on top of) the object it surrounds, such as in some embodiments where the reinforcement structure 280 includes braids that merely sit above object. In some embodiments and contexts, "surrounds" may include that, for example, one or more portions of the reinforcement structure 280 is not only radially exterior of, but also radially interior of (e.g., further inside than, further interior than, or under) the object it surrounds, such as in some embodiments where the reinforcement structure 280 includes braids that weave above and below the object, such that the object is interwoven among the braids. Different embodiments utilize different ones of these types of surrounding configurations when discussing an object surrounded by another object.

Reinforcement structure 280, may, according to some embodiments, be provided to reinforce the elongate shaft member 210 to, among other things, maintain elements such as axial members 250 or steering member 226, 228 at desired positions within the elongate shaft member 210 during use thereof. In some embodiments, the reinforcement structure may enhance bending stiffness of at least part of the elongate shaft member 210. In some embodiments, the reinforcement structure may enhance torsional stiffness of at least part of the elongate shaft member 210. According to various embodiments, the reinforcement structure 280 may include one or more filaments or elements (e.g., metal filaments or polymer filaments). In some embodiments, the reinforcement structure 280 includes a helical structure (e.g., one or more filaments helically wound around the longitudinal axis 230 of the elongate shaft member 210). In some embodiments, the reinforcement structure 280 includes a braided structure (e.g., multiple filaments braided around the longitudinal axis 230 of the elongate shaft member 210). For example, FIG. 4C, reinforcement structure 280 is a braided reinforcement structure 280, according to some embodiments.

In some embodiments, at least a first axial member (e.g., 250A) is woven among the braids of the braided structure (for example, as shown in FIG. 4C). In some embodiments, at least the first steering member (e.g., 226) is woven among the braids of the braided structure. According to various embodiments associated with at least FIG. 4C, the braided reinforcement structure 280 is configured such that at least part of the braided reinforcements structure 280 surrounds at least part of the axial member (250A, 250B). For example, in FIG. 4C, each axial member (250A, 250B) is woven among or through braids of the braided reinforcement structure 280 such that at least part of the braided reinforcement structure 280 surrounds at least part of the axial member. According to various embodiments, at least part of the braided reinforcement structure 280 is embedded in at least part of a wall (e.g., wall 204) of the elongate shaft member 210. According to various embodiments, the wall (e.g., wall 204) of the elongate shaft member 210 is provided at least in part by a tubular member of the elongate shaft member 210. According to various embodiments, the tubular member can include one or more tubular layers (e.g., low friction layer 236 and at least a portion of wall 204 exterior of low friction layer 236, according to some embodiments). In some embodiments, at least part of the braided reinforcement structure 280 is distanced from (a) an outer, exterior, or external surface (e.g., an outer, exterior, or external surface of wall 204) of the tubular member, and (b) and an inner, interior, or internal surface (e.g., an inner, interior, or internal surface of low friction layer 236) of the tubular member. In some embodiments, at least part of the braided reinforcement structure 280 does not interrupt any outer, exterior, or external surface of the tubular member (e.g., an outer, exterior, or external surface of wall 204) and does not interrupt any inner, interior, or internal surface (e.g., an inner, interior, or internal surface of low friction layer 236) of the tubular member. According to some embodiments in which the wall 204 of the elongate shaft member 210 includes a layer (e.g., layer 205 FIGS. 4A, 4C) itself including one or more materials provided on top of an outermost surface 236A of the tubular member (e.g., in cases in which the tubular member is considered low friction layer 236) of the elongate shaft member 210, an embedded at least part of the braided reinforcement structure 280 is distanced or spaced from (a) an exterior surface 205A of the layer, and (b) an interior surface of the tubular member. According to some embodiments, the braided reinforcement structure 280 does not interrupt any exterior surface 205A of the layer and does not interrupt any interior surface 236B of the tubular member. In some embodiments at least in which the tubular member is considered low friction layer 236, such tubular member is considered to be included in the wall 204 of the elongate shaft member 210.

Braided reinforcement structure 280 may be produced by different methods. Conventional braiders used in the manufacture of the catheter reinforcement structures are well known in the art, and as such will not be elaborated there upon in this disclosure. The present inventors have employed a braider model HS80/32-2013-IMC-4K produced by Steeger USA Inc. of South Carolina, U.S.A. to produce examples of various braided reinforcement structures 280 described in this disclosure. It is noted that, braiders such as the HS80/32-2013-IMC-4K braider typically axially feed axially aligned members such as axial members 250A, 250B as various filaments are woven over and under the axially aligned members to braid various braided portions of the braided reinforcement structure 280 around the axially aligned members.

Each of FIGS. 4D and 4E is a partial cross-sectional view of elongate shaft member 210 and handle portion 221, according to some embodiments employing an illustrated embodiment of braided reinforcement structure 280 (shown un-sectioned). In particular, the partial cross-sectional view of FIG. 4D is oriented such that steering member 226 is centrally positioned with respect to the viewer between axial members 250A, 250B, and the partial cross-sectional view of FIG. 4E is oriented such that axial member 250A is centrally positioned with respect to the viewer between steering members 226, 228. According to various embodiments, at least part of braided reinforcement structure 280 is embedded, disposed, incorporated, encapsulated, formed, or located in at least a part of the wall 204 of the elongate shaft member 210. According to various embodiments, the braided reinforcement structure 280 is circumferentially arranged about central longitudinal axis 230 of the elongate shaft member 210, the central longitudinal axis extending between the proximal portion 212 of the elongate shaft member 210 and the distal portion 213 of the elongate shaft member 210.

According to some embodiments, the braided reinforcement structure 280 may include a first braided portion 280*a* including a first pick count, the first braided portion 280*a* of the braided reinforcement structure 280 extending along at least part of the proximal portion 212 of the elongate shaft member 210. According to some embodiments, the braided reinforcement structure 280 may include a second braided portion 280*b* including a second pick count, the second braided portion 280*b* of the braided reinforcement structure 280 extending along at least part of the distal portion 213 of the elongate shaft member 210. According to some embodiments, the braided reinforcement structure 280 may include a third braided portion 280*c* including a third pick count that is greater than each of the first pick count and the second pick count, the third braided portion 280*c* of the braided reinforcement structure 280 extending along at least part of the steerable portion 219 of the elongate shaft member 210. It is noted that a pick count is typically expressed in picks per inch of length (PPI or p.p.i.). A pick may be defined as one repeat of a braid along the braid axis, and a pick count (referred to as a "PIC") may be defined as the number of braid repeats or crosses per unit measure, typically over one inch. A single pick is illustrated in FIG. 4D with reference numeral 283. Higher filament coverage in the braided reinforcement structure 280 is accordingly achieved with higher pick counts.

As described above, the use of the braided reinforcement structure 280 may be motivated for various reasons including reinforcement of the catheter to prevent or inhibit parts of axial members such as steering members 226, 228 and axial members 250A, 250B from buckling, or tearing, breaking or puncturing out from the wall 204 during use. The use of different pick counts in various portions of the braided reinforcement structure 280 may also be motivated for various reasons. For example, in some embodiments, the first braided portion 280*a* axially extends along a length of the proximal portion 212 of elongate shaft member 210 that is typically substantially longer than each of the steerable portion 219 and the distal portion 213 (for example, as exemplified in FIG. 2B). In some embodiments, the relatively longer proximal portion 212 of the elongate shaft member 210 may be subject to wind-up problems when the elongate shaft member 210 is rotated (i.e., about its longitudinal axis 230) as it is a delivered (e.g., percutaneously or intravascularly) through a bodily opening. Wind-up can cause a distal end of the elongate shaft member 210 to be rotationally offset from its proper or normal orientation (e.g., with respect to handle portion 221) and is undesired. According to some embodiments, the first braided portion 280*a* has a relatively low pick count as exemplified by the relatively large diamond shaped openings created by the braided filaments 282 in the first braided portion 280*a* and the relatively shallow braid angles (e.g., as compared to the braided filaments 282 in third braided portion 280*c*). According to various embodiments, the use of a braided portion with a relatively low pick count increases the torsional resistance provided by that braided portion. Therefore, the use of a first braided portion 280*a* including a relatively low pick count can be used to impart greater torsional rigidity to the proximal portion 212, which may reduce problems such as wind-up. According to some embodiments, at least for catheters having an outer diameter of approximately 6-8 mm, the inventors have employed a pick count of 20 PPI for the first braided portion 280*a*, although a range of 15-30 PPI may provide a beneficial pick count for the first braided portion 280*a*, according to some embodiments. In this regard, a beneficial pick count may be dependent on the outer diameter of the catheter, according to some embodiments.

According to some embodiments, the third braided portion 280*c* has a relatively high pick count as exemplified by the relatively small diamond shaped openings created by the braided filaments 282 by the third braided portion 280*c* and the relatively steeper braid angles (e.g., as compared to the braided filaments 282 in first braided portion 280*a*). Braided portions having relatively large pick counts (e.g., third braided portion 280*c*) tend to be more flexible (e.g., in bending) than braided portions having relatively lower pick counts (e.g., first braided portion 280*a*). This enhanced bendability makes the third braided portion 280*c* suitable for reinforcing the steerable portion 219 while allowing the steerable portion 219 to undergo deflection or bending during steering of the catheter. Also, with reference to some embodiments associated with at least FIG. 4E, the smaller distance between adjacent filament portions provided by the third braided portion 280*c* that overlie the axial member 250A, reduce the effective buckling length of portions of the axial member 250A between the adjacent filament portions, thereby reducing compression buckling problems, such as those described above. At least for catheters having an outer diameter of approximately 6-8 mm, the present inventors have employed braided reinforcement structures 280 including third braided portion 280*c* with a pick count of 32 PPI, although a range of 24 PPI to 36 PPI may provide a beneficial pick count for the third braided portion 280*c*, according to some embodiments, although it may be preferable to keep the pick count of the third braided portion 280*c* greater than the pick count of each of the first braided portion 280*a* and the second braided portion 280*b* in some embodiments. It is noted, in some cases in which the third braided portion 280*c* includes a relatively high pick count to not unduly compromise the bendability of the steerable portion 219, that the third pick count cannot be increased beyond certain limits as the adjacent filament braids may want to bind together as the steerable portion 219 is bent. Factors such as the cross-sectional size and shape of the filaments 282 as well as the required amount of angular deflection of the bent steerable portion 219 may typically define these limits.

According to various embodiments, the second braided portion 280*b* is chosen to have a relatively low pick count. At least for catheters having an outer diameter of approximately 6-8 mm, the present inventors have employed braided reinforcement structures 280 including second braided portion 280*b* with a pick count of 24 PPI, although a range of 15 PPI to 30 PPI may provide a beneficial pick count for the second braided portion 280*b*, in some embodiments. Accordingly, in some embodiments, the second pick count (e.g., 24 PPI in some embodiments) for the second braided portion 280*b* may be greater than or at least different than the first pick count (e.g., 20 PPI in some embodiments) for the first braided portion 280*a*.

The choice of a second braided portion 280*b* having a relatively low pick count (e.g., as compared to at least the third braided portion 280*c*) may be motivated for different reasons. For example, after the braided reinforcement structure 280 has been formed, the end portions of the braided reinforcement structure 280 may have a tendency to bell-mouth outwards. In some embodiments, a polymer layer is reflowed (e.g., melted) onto the braided reinforcement structure 280 (e.g., to form at least part of the wall 204). If the bell-mouthed ends of the braided reinforcement structure, are not secured inwardly, they may protrude outwardly beyond the polymer layer and pose a hazard. Although elements such as rings or heat shrink tubing may be employed to outwardly surround the bell-mouthed ends of the braided reinforcement structure 280 to bias them inwardly during the reflow of the polymer layer, an undesired increase in the overall diameter of the catheter may be required to accommodate these elements.

According to some embodiments associated with at least FIGS. 4D and 4E, a first ring 301 (shown in cross-section in FIGS. 4D and 4E) is incorporated in the proximal portion 212 of the elongate shaft member 210, and a second ring 302 (also known as a steering ring in some embodiments) (shown in cross-section in FIGS. 4D and 4E) is incorporated in the distal portion 213 of the elongate shaft member 210. According to various embodiments, each of the first ring 301 and the second ring 302 has outer, exterior, or external dimensions that allow them to fit within the braided reinforcement structure 280. According to some embodiments, at least some filaments 282 of the plurality of filaments 282 of the braided reinforcement structure 280 (e.g., filaments 282 in an end portion (e.g., proximal end portion) of the first braided portion 280*a*) are directly fixedly connected to the first ring 301, and at least some filaments 282 of the plurality of filaments 282 of the braided reinforcement structure 280 (e.g., filaments 282 in an end portion (e.g., a distal end portion) of the second braided portion 280*b*) are directly fixedly connected to the second ring 302. For example, in some embodiments, each filament of the plurality of filaments 282 is a metallic filament, and each of the first ring 301 and the second ring 302 is a metallic ring, with each filament 282 of at least some filaments of the plurality of filaments 282 directly fixedly connected to the first ring 301 via a welded connection, and with each filament 282 of at least some filaments of the plurality of filaments 282 directly fixedly connected to the second ring 302 via a welded connection. By directly fixedly attaching (e.g., by welding such as laser welding) the braided reinforcement structure 280 to the underlying first ring 301 and second ring 302, a low-profile connection is created which does not adversely impact the overall diameter requirements of the catheter.

According to various embodiments, each of the at least some filaments 282 includes (a) a plurality of first portions that underlie other filament portions in the braided reinforcement structure 280, and (b) a plurality of second portions that overlie other filament portions in the braided reinforcement structure 280, as is apparent by the weaving nature of the filaments 282 shown, for example, in FIGS. 4D and 4E, according to some embodiments. According to various embodiments, each filament 282 of the at least some filaments 282 is directly fixedly connected to the first ring 301 via a welded connection connecting one or more of the first portions of the at least some filaments 282 to the first ring 301, and each filament 282 of the at least some filaments 282 is directly fixedly connected to the second ring 302 via a welded connection connecting one or more of the first portions of the at least some filaments 282 to the second ring 302. In this regard, these particular underlying portions of each of the filaments 282 are arranged to more easily contact the first ring 301 and the second ring 302 while the overlying portion are not, according to some embodiments. Welding the underlying portions of the filaments 282 may provide for a more secure weld, according to some embodiments. Welding the underlying portions of the filaments 282 as opposed to the overlying portions of the filaments may provide for a more secure weld, according to some embodiments. It is noted that if the second braided portion 280*b* includes a relatively high pick count (e.g., like the third braided portion 280*c*), access to underlying portions of the filaments 282 may be more difficult due to the higher filament coverage associated with higher pick counts, and direct fixed connection of the underlying portions of the filaments 282 to the rings may, consequently, be more difficult to achieve. In a similar manner, in some embodiments, at least part of the braided reinforcement structure 280 may surround at least a portion of a metallic steering member (e.g., steering member 226 or steering member 228) that is to be welded or otherwise directly fixedly connected to an underlying metallic ring 302 through an opening defined by braids of the second braided portion 280*b* of the braided reinforcement structure 280. In this instance, the use of higher pick counts may make the opening defined by the braids smaller, thereby making this operation more difficult to complete. Accordingly, a relatively lower pick count for second braided portion 280*b* may be beneficial, according to some embodiments.

Braiders such as the HS80/32-2013-IMC-4K braider discussed above can produce a braided reinforcement structure portion by rotating various spools of braid-forming filaments while axially feeding a mandrel onto which the filaments are braided. A particular pick count in the braided reinforcement structure portion can be achieved by rotating various spools of braid-forming filaments at a particular rotational speed and adjusting the axial feed rate of the mandrel in accordance with the desired pick count. The present inventors have employed such techniques to produce each of the first braided portion 280*a*, the second braided portion 280*b*, and the third braided portion 280*c*. In some embodiments, a transition portion 280*ac* may be present between the first braided portion 280*a* and the third braided portion 280*c*. In some embodiments, a transition portion 280*cb* may be present between the third braided portion 280*c* and the second braided portion 280*b*. Transition portions 280*ac* and 280*cb* may result from adjustments in braider operating parameters required to transition between adjacent portions of the braided reinforcement structure 280 including different pick counts. Transition portions 280*ac* and 280*cb* are exaggerated for illustration purposes in FIGS. 4D, 4E, and are typically smaller than indicated in these particular figures.

In FIGS. 4D, 4E, the braided reinforcement structure 280 includes a plurality of filaments 282, the plurality of filaments 282 braided together to form the braided reinforcement structure 280. According to various embodiments, each of the filaments 282 can have various cross-sectional shapes including rectangular, ovoid, elliptical and circular, by way of non-limiting example. In FIGS. 4D, 4E, each of the filaments 282 extend along a respective helical path arranged about the longitudinal axis 230 of the elongate shaft member 210, according to some embodiments. According to various embodiments, each of the first braided portion 280*a* of the braided reinforcement structure 280, the second braided portion 280*b* of the braided reinforcement structure 280, and the third braided portion 280*c* of the braided reinforcement structure 280 includes a respective portion of each filament of the plurality of filaments 282. In other words, in some embodiments, each helically oriented filament 282 in the braided reinforcement structure 280 includes a respective portion in each of the first braided portion 280*a* of the braided reinforcement structure 280, the second braided portion 280*b* of the braided reinforcement structure 280, and the third braided portion 280*c* of the braided reinforcement structure 280.

According to various embodiments, the first braided portion 280*a* of the braided reinforcement structure 280 is embedded in at least a first polymer portion 232*a* of the wall 204 of the elongate shaft member 210, the first polymer portion 232*a* including or having a first hardness. According to various embodiments, the second braided portion 280*b* of the braided reinforcement structure 280 is embedded in at least a second polymer portion 232*b* of the wall 204 of the elongate shaft member 210, the second polymer portion 232*b* including or having a second hardness. According to some embodiments, the third braided portion 280*c* of the braided reinforcement structure 280 is embedded in at least a third polymer portion 232*c* of the wall 204 of the elongate shaft member 210, the third polymer portion 232*c* including or having a third hardness.

In some embodiments, a first polymer transition region 232*ac* exists between the first polymer portion 232*a* and the third polymer portion 232*c*, and a second polymer transition region 232*cb* exists between the third polymer portion 232*c* and the second polymer portion 232*b*. In some embodiments, the first braided portion 280*a* and at least part of the transition portion 280*ac* of the braided reinforcement structure 280 are embedded at least in the first polymer portion

232*a*. In some embodiments, although not shown in the example of FIG. 4D, at least part of the transition portion 280*ac* of the braided reinforcement structure 280 is embedded in the third polymer portion 232*c*. In some embodiments, the third braided portion 280*c* of the braided reinforcement structure 280 and at least part of the transition portion 280*cb* of the braided reinforcement structure 280 are embedded in the third polymer portion 232*c*. In some embodiments, although not shown in the example of FIG. 4D, at least part of the transition portion 280*cb* of the braided reinforcement structure 280 is embedded at least in the second polymer portion 232*b*. In some embodiments, although not shown in the example of FIG. 4D, at least part of the first braided portion 280*a* of the braided reinforcement structure 280 is embedded at least in the first polymer transition region 232*ac*. In some embodiments, at least part of the third braided portion 280*c* of the braided reinforcement structure 280 is embedded at least in the first polymer transition region 232*ac*. In some embodiments, although not shown in the example of FIG. 4D, at least part of the third braided portion 280*c* of the braided reinforcement structure 280 is embedded at least in the second polymer transition region 232*cb*. In some embodiments, at least part of the second braided portion 280*b* of the braided reinforcement structure 280 is embedded in the second polymer transition region 232*cb*. Although the polymer transition regions 232*ac*, 232*cb* do not align, in some embodiments (as shown in the example of FIG. 4D), with the transition portions 280*ac*, 280*cb*, respectively, of the braided reinforcement structure 280, other embodiments may have them aligned.

According to various embodiments, each of the first hardness of the first polymer portion 232*a* and the second hardness of the second polymer portion 232*b* may be greater or increased (i.e., harder) as compared to the third hardness of the third polymer portion 232*c*. The present inventors have constructed catheters with first polymer portions 232*a* made from Nylon 12 (VESTAMID (Registered Trademark as noted above)) including a 75 Shore D hardness for the corresponding first hardness, second polymer portions 232*b* made from PEBAX (Registered Trademark as noted above) 7233 including a 69 Shore D hardness for the corresponding second hardness, and the third polymer portions 232*c* made from PEBAX 3533 including a 33 Shore D hardness for the corresponding third hardness. In these particular embodiments, the first hardness of the first polymer portion is greater or increased (i.e., harder) as compared to the second hardness.

In some embodiments, it may be beneficial to have the first hardness of the first polymer portion 232*a* be in a range of 60-78 Shore D hardness. In some embodiments, it may be beneficial to have the second hardness of the second polymer portion 232*b* be in a range of 55-75 Shore D hardness. In some embodiments, it may be beneficial to have the third hardness of the third polymer portion 232*c* be in a range of 25-55 Shore D hardness, with, in some embodiments, smaller diameter catheters tending toward the harder side of such range (e.g., up to 55 Shore D hardness) and larger diameter catheters tending toward the softer side of such range (e.g., 25-40 or 25-45 Shore D hardness).

The difference in hardness between at least the third polymer portion 232*c* and the first and second polymer portions 232*a*, 232*b* may be motivated by different reasons. For example, in various embodiments, the third polymer portion 232*c* may form part of the steerable portion 219 of the elongate shaft member 210, which is configured to bend, and as such benefits from less hardness to do so. On the other hand, the first polymer portion 232*a* may form part of the proximal portion 212 of the elongate shaft member 210, which is configured to have relatively greater bending stiffness and torsional stiffness, and hence may benefit from harder polymers, according to some embodiments. The second polymer portion 232*b* may, in some embodiments, encapsulate end portions of the filaments 282 and, thus, require a greater or increased hardness as compared to the third hardness to restrict the end portions of the filaments from piercing therethrough.

With reference to FIGS. 4D, 4E, and FIGS. 2A-2C, according to some embodiments, the catheter includes at least a first steering member, at least part of which is incorporated into at least a portion (sometimes referred to as a "first" portion in some contexts) of the wall 204 of the elongate shaft member 210. In some embodiments, the at least the first steering member includes at least steering member 226, steering member 228, or both steering member 226 and steering member 228. In some embodiments, an actuator, such as the actuator set 240 (e.g., FIGS. 2A-2C) is configured to manipulate the at least the first steering member to cause deflection of the at least the steerable portion 219 in a first particular plane (e.g., as discussed above with respect to FIGS. 2A-2C), the at least the first steering member extending between the proximal portion 212 of the elongate shaft member 210 and the distal portion 213 of the elongate shaft member 210. According to various embodiments, at least part of the third braided portion 280*c* of the braided reinforcement structure 280 surrounds at least a portion (sometimes referred to as a "first" portion in some contexts) of the at least the first steering member. For example, in FIGS. 4D and 4E, the third braided portion 280*c* surrounds at least part of each of the steering member 226 and steering member 228. According to some embodiments, at least part of the first braided portion 280*a* of the braided reinforcement structure 280 surrounds at least a portion of the at least the first steering member. For example, in FIGS. 4D and 4E, the first braided portion 280*a* surrounds at least part of each of the steering member 226 and steering member 228. According to some embodiments, at least part of the second braided portion 280*b* of the braided reinforcement structure 280 surrounds at least a portion (sometimes referred to as a "second" portion in some contexts) of the at least the first steering member. For example, in FIGS. 4D and 4E, the second braided portion 280*b* surrounds at least part of each of the steering member 226 and steering member 228.

In some embodiments, a steering ring (e.g., 302) is incorporated in the distal portion 213 of the elongate shaft member 210, and at least the first steering member (e.g., steering member 226, steering member 228, or both steering member 226 and steering member 228) is directly fixedly connected to the steering ring (e.g., such as ring 302 in some embodiments). In some embodiments, at least the second braided portion 280*b* of the braided reinforcement structure 280 is radially exterior, with respect to a central longitudinal axis (e.g., axis 230) of the elongate shaft member 210, of at least a region of the steering ring (e.g., such as ring 302 in some embodiments) to which the at least the first steering member is directly fixedly connected. For example, as shown in FIGS. 4D and 4E, the second braided portion 280*b* resides outside or on top of (radially exterior of) the ring 302, with respect to the central longitudinal axis 230. In some embodiments, the steering ring is a metallic steering ring, and each of the at least the first steering member (e.g., 226, 228) is a respective metallic steering member, the respective metallic steering member welded (e.g., laser welded) to the metallic ring.

Returning to a discussion of axial members 250A and 250B, such axial members have various characteristics and configurations, according to various embodiments. In some embodiments, such an axial member may provide at least a first axial strengthening member embedded into the wall 204 of the elongate shaft member 210. The at least the first axial strengthening member may be the axial member 250A, the axial member 250B, or both the axial member 250A and the axial member 250B. The at least the first axial strengthening member may be located at least between the proximal portion 212 of the elongate shaft member 210 and the distal portion 213 of the elongate shaft member 210. In some embodiments, an end of the at least the first axial strengthening member may be located at, or at least proximate to the distal portion 213 of the elongate shaft member 210. The at least the first axial strengthening member may be configured to at least (a) reduce lateral deflection of the at least the steerable portion 219 of the elongate shaft member 210 away from a first particular plane during the deflection of the at least the steerable portion 219 of the elongate shaft member 210 in the first particular plane (e.g., as discussed above with respect to at least FIGS. 2A-2C and 4A), (b) provide increased resistance to compressive loading failure of at least part of the elongate shaft member 210 during the deflection of the at least the steerable portion 219 of the elongate shaft member 210 in the first particular plane, or both (a) and (b). In some embodiments, the at least the first axial strengthening member (e.g., axial member 250A, axial member 250B, or both) is not directly fixedly connected to the first ring 301, the second ring 302, or both the first ring 301 and the second ring 302. For example, referring back to FIGS. 4D and 4E, the axial members 250A, 250B are shown outside or on top of (radially exterior of) the rings 301, 302, and, in some embodiments, such axial members 250A, 250B may not be connected to such rings 301, 302 and may, in some embodiments, instead, merely contact them. According to various embodiments, the at least the first axial strengthening member (e.g., axial member 250A, axial member 250B, or both) is positioned at least proximate the first ring 301 and the second ring 302 without direct fixed connection therebetween. In some embodiments, at least the second braided portion 280*b* of the braided reinforcement structure 280 is radially exterior, with respect to a central longitudinal axis 230 of the elongate shaft member 210, of at least a region of the second ring 302 to which the at least the first steering member 226 is directly fixedly connected. In some embodiments, at least part of the second braided portion 280*b* of the braided reinforcement structure 280 is radially exterior, with respect to the central longitudinal axis 230 of the elongate shaft member 210, of at least a first part of the at least the first axial strengthening member (e.g., as shown with 250B in FIG. 4E). In some embodiments, the at least the first axial strengthening member (e.g., axial member 250A, axial member 250B, or both) is woven among or through braids of at least the first braided portion 280*a*, the second braided portion 280*b*, the third braided portion 280*c*, or a combination of some or all of the first braided portion 280*a*, the second braided portion 280*b*, and the third braided portion 280*c*, according to some embodiments.

According to various embodiments, a catheter, such as a steerable catheter, may include an elongate shaft member 210 that includes a proximal portion 212, a distal portion 213, and a wall 204. According to various embodiments, the elongate shaft member 210 is configured to be deliverable at least partially through a bodily opening leading to a bodily cavity with the distal portion 213 ahead of the proximal portion 212, such as is the case with steerable catheter 200, although other catheter types may be used, according to some embodiments. According to some embodiments, the wall 204 of the elongate shaft member 210 may include one or more polymer layers. According to some embodiments, the catheter may include an elongate thermoplastic member (e.g., which may be an example of the axial member 250A or 250B in some embodiments). At least part (e.g., at least part 250A-1 at least in FIG. 4C in some embodiments) of the elongate thermoplastic member may be embedded into at least a particular polymer layer (e.g., layer 205) of the one or more polymer layers of the wall 204 of the elongate shaft member 210. The embedded at least the part of the elongate thermoplastic member may extend along or with a longitudinal axis (e.g., longitudinal axis 230) of the elongate shaft member 210 between the proximal portion 212 of the elongate shaft member 210 and the distal portion 213 of the elongate shaft member 210. In some embodiments, the particular polymer layer (e.g., layer 205) of the one or more polymer layers of the wall 204 of the elongate shaft member is a tubular layer, e.g., as discussed above in some embodiments. In some embodiments, the tubular layer (e.g., layer 205) includes an exterior or outer surface (e.g., exterior or outer surface 205A) and an interior or inner surface (e.g., interior or inner surface 205B) radially inward from the exterior or outer surface with respect to the longitudinal axis 230 of the elongate shaft member 210. The embedded at least the part (e.g., at least the part 250A-1) of the elongate thermoplastic member (e.g., axial member 250A in one example embodiment) may be located between the outer surface and the inner surface.

In some embodiments, as noted above, the axial member 250A or the axial member 250B may be such an elongate thermoplastic member, but the elongate thermoplastic member is not limited to these particular embodiments. In some embodiments, the elongate thermoplastic member is a first elongate thermoplastic member (e.g., 250A), and the catheter includes a second elongate thermoplastic member (e.g., 250B). At least part (e.g., at least part 250B-1 in FIG. 4C) may be embedded into the wall 204 of the elongate shaft member 210, and at least a portion (e.g., at least portion 250B-2 in FIG. 4C) of the second elongate thermoplastic member may be positioned diametrically opposite across at least one cross-section (e.g., as shown at least in FIG. 4C) of the elongate shaft member from at least a portion of the first elongate thermoplastic member. According to some embodiments, the second elongate thermoplastic member extends between the proximal portion 212 of the elongate shaft member 210 and the distal portion 213 of the elongate shaft member 210. In some embodiments, each of the first elongate thermoplastic member (e.g., 250A) and the second elongate thermoplastic member (e.g., 250B) includes a respective axis (e.g., axis 257 extending into and out of the page in FIG. 4B) that extends between the proximal portion 212 of the elongate shaft member 210 and the distal portion 213 of the elongate shaft member 210.

In some embodiments, the elongate shaft member 210 includes a steerable portion (e.g., steerable portion 219 shown in FIGS. 2A-2C), and the catheter includes an actuator (e.g., actuator set 240) located at least proximate the proximal portion 212 of the elongate shaft member 210 by way of non-limiting example. The actuator may be operatively coupled to the steerable portion 219 to transmit force thereto to steer at least the steerable portion 219. In some embodiments, the steerable portion 219 of the elongate shaft member 210 is located between the proximal portion 212 of the elongate shaft member 210 and the distal portion 213 of the elongate shaft member 210 (e.g., with respect to the longitudinal axis 230).

In some embodiments, the actuator is operatively coupled to the steerable portion 219 to cause deflection of the at least the steerable portion 219 in a first particular plane (e.g., represented by broken line 235 in FIG. 4A, according to some embodiments). In some embodiments, the elongate thermoplastic member is configured at least to resist, at least in part, lateral deflection of the at least the steerable portion 219 away from the first particular plane during the deflection of the at least the steerable portion 219 in the first particular plane. In some embodiments in which the catheter includes a first elongate thermoplastic member (e.g., 250A) and a second elongate thermoplastic member (e.g., 250B), the first elongate thermoplastic member, the second elongate thermoplastic member, or both the first elongate thermoplastic member and the second elongate thermoplastic member is or are configured at least to resist, at least in part, the lateral deflection of the at least the steerable portion 219 away from the first particular plane during the deflection of the at least the steerable portion 219 in the first particular plane. In some embodiments, the respective axis (e.g., axis 257 shown in FIG. 4B) of the first elongate thermoplastic member (e.g., 250A) and the respective axis of the second elongate thermoplastic member (e.g., 250B) lie in a second particular plane (e.g., represented by broken line 237 in FIG. 4A, according to some embodiments), the second particular plane intersecting the first particular plane (e.g., represented by broken line 235 in FIG. 4A, according to some embodiments). In some embodiments, the second particular plane is orthogonal to the first particular plane (e.g., as shown in the example of FIG. 4A). In some embodiments, the catheter includes a first steering member (e.g., 226) and a second steering member (e.g., 228), and the actuator is configured to manipulate the first steering member, the second steering member, or both the first steering member and the second steering member, to cause deflection of the at least the steerable portion in the first particular plane.

According to some embodiments, the catheter may include a reinforcement structure (e.g., 280) surrounding the embedded at least the part of an elongate thermoplastic member (e.g., elongate thermoplastic member 250A or 250B). At least part (e.g., at least part 280-1 shown in FIG. 4C) of the reinforcement structure 280 may be embedded into the wall 204 of the elongate shaft member 210. In some embodiments, at least a portion (e.g., at least portion 280-2 shown in FIG. 4D) of the embedded at least the part of the reinforcement structure 280 includes a plurality of filaments (e.g., 282). In some embodiments, at least the part of the reinforcement structure 280 is embedded in at least the particular polymer layer (e.g., particular polymer layer 205) of the one or more polymer layers of the wall (e.g., wall 204) of the elongate shaft member (e.g., elongate shaft member 210). In some embodiments, the reinforcement structure 280 may include a helical structure. For example, each of at least some of the filaments 282 may have a wound or helical form. In some embodiments, a first set (e.g., first set 282-1 shown at least in FIG. 4D) of the plurality of filaments 282 are wound in a first direction, and a second set (e.g., second set 282-2 shown at least in FIG. 4D) of the plurality of filaments 282 are wound in a second direction opposite or opposing the first direction (e.g., an opposite or opposing winding or helical direction, in some embodiments). In some embodiments, the reinforcement structure 280 includes a braided structure.

According to some embodiments, the embedded at least the part (e.g., at least part 250A-1 shown at least in FIG. 4C) of the elongate thermoplastic member (e.g., 250A) is woven among braids of the braided structure, in some embodiments in which the reinforcement structure 280 includes a braided structure, for example, as shown in at least FIG. 4C and FIG. 4D. In some embodiments, various filaments 282 of the plurality of filaments are interwoven together, for example, as shown in at least FIG. 4C, FIG. 4D, and FIG. 4E. In some embodiments, the embedded at least the part of the elongate thermoplastic member (e.g., 250A) is woven among at least some filaments of the plurality of filaments 282. In some embodiments, at least a first portion (e.g., at least first portion 280-3 shown in at least FIG. 4C) of the reinforcement structure 280 surrounds at least a respective portion of the first steering member 226, the second steering member 228, or each of the first steering member 226 and the second steering member 228. In some embodiments, the reinforcement structure 280 may include a braided structure, and at least part of the first steering member 226, the second steering member 228, or both the first steering member 226 and the second steering member 228 may be woven among braids of the braided structure. In this regard, the embodiment of FIG. 4C shows respective portions (one portion 280-4 called out in FIG. 4C) of the reinforcement structure 280 deflecting, or protruding into, each of the first steering member 226 and the second steering member 228. This deflecting, or protruding into may occur in some embodiments in which the tubular members of the steering members are made of a relatively compressible material and the winding of the reinforcement structure 280 is performed under relatively high tensions. However, in other embodiments, the reinforcement structure 280 may include little or no deflecting, or protruding into the steering members (e.g., 226, 228).

According to various embodiments, at least a first portion (e.g., at least first portion 250A-2 shown at least in FIG. 4C and FIG. 4D) of the embedded at least the part of the elongate thermoplastic member (e.g., 250A) includes indentations (e.g., at least indentations 330 referenced at least in FIG. 4C, but also discussed in more detail below with respect to indentations 330' shown in FIG. 4F) in a surface (e.g., at least surface 250A-3 shown at least in FIG. 4C and FIG. 4D) of the first portion of the embedded at least the part of the elongate thermoplastic member (e.g., 250A) into which the portion (e.g., at least a portion 280-2) of the embedded at least the part of the reinforcement structure 280 is embedded. In some embodiments, the first portion (e.g., at least first portion 250A-2) of the embedded at least the part of the elongate thermoplastic member (e.g., 250A) includes a polyaryletherketone (PAEK) polymer. In some embodiments, the polyaryletherketone (PAEK) polymer is polyether ether ketone (PEEK). According to some embodiments, the first portion (e.g., at least first portion 250A-2) has been melted or softened about the portion (e.g., at least portion 280-2) of the embedded at least the part of the reinforcement structure to embed the portion of the embedded at least the part of the reinforcement structure into the surface of the first portion (e.g., at least first portion 250A-2), thereby forming the indentations. In some embodiments, the first portion (e.g., at least first portion 250A-2) of the embedded at least the part of the elongate thermoplastic member (e.g., 250A) exhibits a characteristic of having undergone cold crystallization, which as discussed in more detail below, may facilitate effective formation of the indentations, in some embodiments.

According to some embodiments, a portion of each filament 282 of at least some of the plurality of filaments of the reinforcement structure 280 is embedded in a respective indentation 330 of the indentations in the surface (e.g., at least surface 250A-3) of the first portion (e.g., at least first portion 250A-2) of the embedded at least the part of the elongate thermoplastic member (e.g., 250A). FIG. 4C and FIG. 4D each show an instance of such a portion 282*e* of a filament 282, for example. Embedding the at least the part (e.g., at least the part 280-1) of the reinforcement structure (e.g., 280) into indentations (e.g., 330) provided in a surface (e.g., at least surface 250A-3) of the first portion (e.g., at least first portion 250A-2) of the embedded at least the part of the elongate thermoplastic member (e.g., 250A) may be motivated for various reasons (for example, as described below in this disclosure).

The indentations provided in a surface of the first portion of the embedded at least the part of the elongate thermoplastic member (e.g., 250A) may have various physical characteristics according to various embodiments. For example, in some embodiments, each of at least one filament 282 of the plurality of filaments 282 of the braided structure 280 has a particular dimension (one of which is signified with reference 282*d* in FIG. 4C) in a radial direction (e.g., 210*c*) with respect to the longitudinal axis 230 of the elongate shaft member 210, and a depth (one of which is signified with reference 330*d* in FIG. 4C) of each of at least some of the indentations from the surface of the first portion of the embedded at least the part of the elongate thermoplastic member (e.g., 250A) may be at least a particular percentage of the particular dimension (e.g., 282*d*), according to various embodiments. In some embodiments, a depth 330*d* of each of at least some of the indentations 330 is at least 40% of the particular dimension 282*d* of the corresponding filament 282. A depth 330*d* of each of at least some of the indentations 330 may be at least 40%, in some embodiments, within a range of 40%-90% in some embodiments, or within a range of 50-75% of the particular dimension 282*d* of the corresponding filament 282. In some embodiments, it may be preferable to have the depth 330*d* be sufficiently deep, such that the filament 282 is thoroughly embedded into the elongate thermoplastic member (e.g., 250A or 250B) to properly secure the filament 282 to the elongate thermoplastic member and prevent relative movement between the filament 282 and the elongate thermoplastic member, while not being too deep to a point where the structural integrity of the elongate thermoplastic member is in question and the elongate thermoplastic member may be unacceptably at risk of breaking during delivery of the catheter into a patient.

It should be noted that FIG. 4C shows gaps 332 between a respective portion of the reinforcement structure 280 and the respective elongate thermoplastic member 250A, 250B. Such gaps 332 may be present in some embodiments depending at least on the winding characteristics of the reinforcement structure 280, the stiffness of the filaments 282, the hardness of the respective elongate thermoplastic member 250A, 250B, or the desired depth of protrusion of the respective filament 282 into the respective elongate thermoplastic member. However, other embodiments may not have such gaps 332 present.

Figure 5:
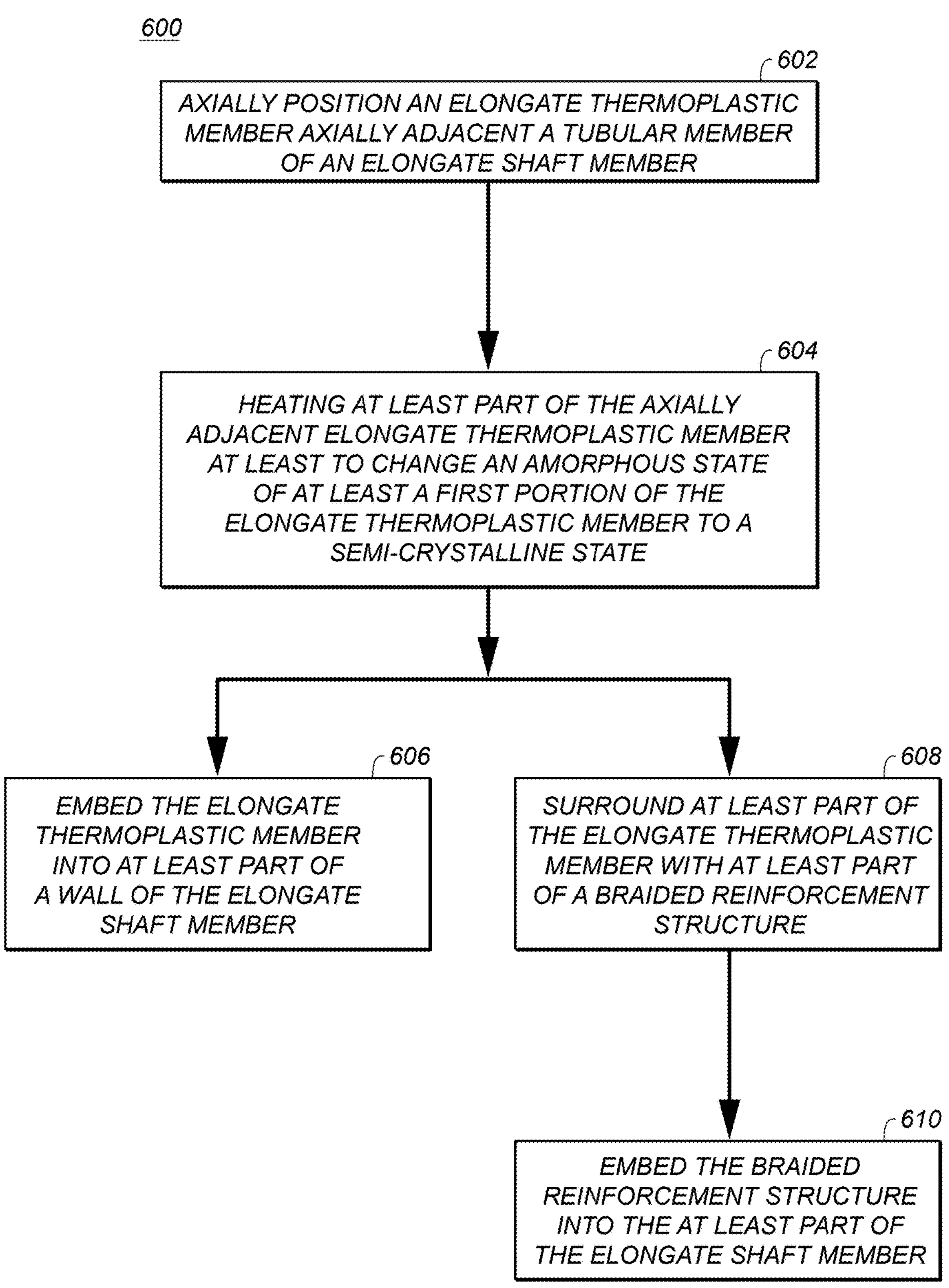
FIG. 5 illustrates methods of manufacturing at least part of a steerable catheter, according to some embodiments.

The indentations 330 provided in a surface of the first portion of the embedded at least the part of the elongate thermoplastic member (e.g., 250A) may be formed by various methods. In some embodiments, the indentations 330 are formed during the manufacturing of at least part of the catheter 200. In some embodiments, the indentations may be formed during a process in which the at least part of the elongate thermoplastic member is embedded into at least a particular polymer layer of the one or more polymer layers (e.g., 205) of the wall 204 of the elongate shaft member 210, for example, as described in more detail below. FIG. 5 is a block diagram describing a method 600 of manufacturing at least part of a catheter (e.g., a steerable catheter), according to some embodiments. In some embodiments, method 600 may be employed to form indentations in at least the part of an elongate thermoplastic member (e.g., 250A), although it is understood that other methods of forming the indentations may be employed according to other embodiments. For example, some embodiments of the methods of FIG. 5 described below include a heating and embedding process, but some methods that may form the indentations may include, but are not limited to, machining, etching, or by producing the elongate thermoplastic member with the indentations integrally formed therein (e.g., by molding or 3D printing).

In some embodiments, method 600 of FIG. 5 may include a subset of the associated blocks or may include additional blocks than those shown in FIG. 5. In some embodiments, method 600 may include a different sequence indicated between various ones of the associated blocks shown in FIG. 5. For example, in some embodiments, the actions associated with blocks 602 and 608 may occur concurrently, followed by the actions 606, followed by the concurrent actions associated with blocks 604 and 610.

Block 602 may include, according to some embodiments, axially positioning at least a portion of an elongate thermoplastic member axially adjacent at least a portion of a tubular member of an elongate shaft member. In some embodiments, the axial member 250A or the axial member 250B may be such an elongate thermoplastic member. For example, in some embodiments, elongate axial member 250A (e.g., axial member 250A will be referred to in this example, but another or one or more other axial members such as axial member 250B or other axial member may be used in addition or instead in other embodiments) is at least in part axially positioned axially adjacent at least part of the tubular member (e.g., as shown in FIGS. 4D and 4E) (which may include or be low friction material layer 236). In some embodiments, the elongate thermoplastic member 250A includes at least a first portion including or having an amorphous state. In some embodiments, the phrase “amorphous state” refers to a molecular state of the thermoplastic member, such as an amorphous, irregular, or random arrangement of molecules or molecular chains in the respective portion of the member. According to some embodiments, the first portion may include an entirety of the elongate thermoplastic member 250A at least in the state associated with block 602. According to some embodiments, although block 602 refers to “an” elongate thermoplastic member, the descriptions and processes described with respect to block 602 may be associated with multiple elongate thermoplastic members, such as both of axial members 250A, 250B. For instance, each of the axial members 250A and 250B may include a respective first portion including an amorphous state. A corresponding analysis regarding the applicability to multiple elongate thermoplastic members applies to blocks 604, 606, 608, and 610, discussed in more detail below.

Block 604 includes, according to some embodiments, heating at least part of the axially adjacent elongate thermoplastic member 250A at least to change the amorphous state of the at least the first portion of the elongate thermoplastic member 250A to a semi-crystalline state. Changing the amorphous state to the semi-crystalline state causes polymer molecule chains in the thermoplastic to become more aligned in an orderly manner and thus impart greater strength and rigidity than in the amorphous state.

In the amorphous state, the molecule chains of the thermoplastic are randomly arranged in a disorganized, intertwined manner which imparts lower strength in the thermoplastic, but allows it to more readily melt (unlike its semi-crystalline state). Various thermoplastics can change from an amorphous state to a semi-crystalline state in a process known as "cold crystallization". Cold crystallization is an exothermic process for increasing the degree of crystallinity in an amorphous thermoplastic portion to convert it into a semi-crystalline thermoplastic portion. Typically, the amorphous state is created by quickly cooling or quenching heated thermoplastic (e.g., upon extrusion during an extrusion process) so that it has little time to crystallize into a semi-crystalline state. Cold crystallization involves heating the previously cooled thermoplastic to cause the formation of small crystals, thereby changing the amorphous state into a semi-crystalline state. It is noted that for a semi-crystalline thermoplastic portion to melt, it must be heated at least to its melting temperature. Cold crystallization of an amorphous thermoplastic portion occurs at temperatures above the glass transition temperature of the amorphous thermoplastic portion which is well below the melting temperature. It is noted that semi-crystalline thermoplastic portions typically have sharp melting points while amorphous thermoplastic portions soften gradually unlike the semi-crystalline thermoplastic portions. It is noted that, when the thermoplastic material is in an amorphous state, it will contain some crystalline materials, and when the thermoplastic is in its semi-crystalline state, it will contain some amorphous material. It is understood that, whether the thermoplastic material is in an amorphous state or a semi-crystalline state, is not based on its exact material composition, but rather on its thermal behavior as described herein, and as known to those skilled in the art.

A particular thermoplastic that can undergo cold crystallization is polyethylene terephthalate (PET). In some embodiments, at least the first portion of the elongate thermoplastic member 250A including the amorphous state at block 602 includes a polyaryletherketone (PAEK) polymer. Polyaryletherketone (PAEK) includes a family of high-performance polymers that can undergo cold crystallization. In some embodiments, the polyaryletherketone (PAEK) polymer is polyether ether ketone (PEEK).

Block 606 includes embedding at least part of the elongate thermoplastic member 250A into at least part of the wall 204 of the elongate shaft member 210. According to various embodiments, the embedded at least the part of the elongate thermoplastic member 250A extends along an axis of the elongate shaft member 210 between a proximal portion 212 of the elongate shaft member 210 and a steerable portion 219 of the elongate shaft member 210, the elongate shaft member 210 configured to be deliverable at least partially through a bodily opening leading to a bodily cavity with the steerable portion ahead 219 of the proximal portion 212. According to various embodiments, the embedded at least the part of the elongate thermoplastic member 250A extends along an axis of the elongate shaft member 210 between a proximal portion 212 of the elongate shaft member 210 and a steerable portion 219 of the elongate shaft member 210.

Embedding at least part of the elongate thermoplastic member 250A into at least part of the wall 204 of the elongate shaft member 210 may be accomplished in various ways. According to some embodiments, the embedding at least part of the elongate thermoplastic member 250A into the at least the part of the wall 204 of the elongate shaft member 210 includes positioning one or more polymer materials (e.g., in a solid state) in proximity to the elongate thermoplastic member 250A. According to some embodiments, block 606 includes heating the one or more polymer materials to reflow and encapsulate at least part of the elongate thermoplastic member 250A. According to various embodiments, the embedding at least part of the elongate thermoplastic member 250A into the at least the part of the wall 204 of the elongate shaft member 210 includes reflowing one or more polymer materials over at least the tubular member (which may include low friction material layer 236). The reflow process typically involves, according to some embodiments, positioning the tubular member (which may include low friction material layer 236) on a mandrel and surrounding the tubular member (which may include low friction material layer 236) and the axially adjacent part of the elongate thermoplastic member 250A with one or more solid polymer layers. Heat shrink tubing may be, according to some embodiments, positioned over the surrounding polymer layers and the assemblage is heated to temperatures sufficient to cause the one or more polymer layers to melt and reflow. The temperatures also cause the heat shrink tubing to shrink and compress the one or more polymer layers to fill any voids that are present. The axially adjacent part of the elongate thermoplastic member 250A thus becomes embedded or encapsulated in the wall 204 of the elongate shaft member 210, according to some embodiments.

Reflow temperatures may vary with the particular polymers that are to be reflowed. For example, the aforementioned first polymer portion 232*a* made from Nylon 12 (VESTAMID (Registered Trademark as noted above)) including a 75 Shore D hardness has a melt or reflow temperature of 178° C., the second polymer portion 232*b* made from PEBAX (Registered Trademark as noted above) 7233 including a 69 Shore D hardness has a melt or reflow temperature of 174° C., and the third polymer portion 232*c* made from PEBAX (Registered Trademark as noted above) 3533 including a 33 Shore D hardness has a melt or reflow temperature of 144° C. A typical reflow temperature of 180° C. has been employed by the inventors to reflow an assemblage of these three polymers. In some embodiments, the reflow temperature to reflow an assemblage of three polymers for the polymer portions 232*a*, 232*b*, 232*c* may beneficially be in a range of 174-220° C.

According to various embodiments, the at least the first portion (e.g., at least first portion 250A-2) of the elongate thermoplastic member 250A that is embedded into the elongate shaft member 210 may have, or may be in a semi-crystalline state. Semi-crystalline states may be created in various thermoplastic members by different processes. For example, a semi-crystalline state may be "created from melt" when a particular melted thermoplastic member is cooled relatively slowly from its melt temperature $T_m$. A semi-crystalline state may also be created when a particular thermoplastic member in an amorphous state undergoes cold crystallization as temperatures are increased from its glass transition temperature Tg. It is noted that differences may be noted between these two semi-crystalline states that are produced by different processes. For example, the degree or amount of crystallinity (e.g., the percentage of crystalized portions to amorphous portions) is typically greater when the semi-crystalline state is "created from melt" rather than by being produced via cold crystallization. By way of another example, the size of the formed crystals tends to be relatively larger when the semi-crystalline state is "created from melt" rather than by being produced via cold crystallization, which tends to provide relatively smaller sized crystals. These differences may be especially prevalent when the cold-crystallization temperatures that do not significantly exceed the glass transition temperature of the particular thermoplastic are employed. For example, establishing a semi-crystalline state via cold-crystallization at the relatively low reflow temperatures described above (e.g., 174-220° C.) with an amorphous polyether ether ketone (PEEK) thermoplastic member having a glass transition temperature of approximately 145° C. may typically have smaller crystals and/or a smaller percentage of crystalline to amorphous composition than if the polyether ether ketone (PEEK) thermoplastic member obtained a semi-crystalline state by slowing cooling from its melt temperature of 343° C. Nonetheless, mechanical properties of the semi-crystalline thermoplastic member when produced by cold crystallization typically will be better than the mechanical properties attributed to it in its amorphous state. Crystal structure is an example of a characteristic of at least a first portion (e.g., at least first portion 250A-2) of the embedded at least the part of the elongate thermoplastic member (e.g., 250A) having undergone cold crystallization. The degree of crystallinity may be determined by various methods including density measurement, differential scanning calorimetry (DSC), X-ray diffraction (XRD), infrared spectroscopy and nuclear magnetic resonance (NMR). In some embodiments, the heating per block 604 of at least part of the axially adjacent elongate thermoplastic member 250A at least to change the amorphous state of the at least the first portion of the elongate thermoplastic member 250A to the semi-crystalline state occurs prior to the embedding (e.g., according to block 606 or block 610 discussed in more detail below) of at least part of the elongate thermoplastic member 250A into the at least part of the wall 204 of the elongate shaft member 210. In some embodiments, the heating per block 604 of the at least part of the axially adjacent elongate thermoplastic member 250A at least to change the amorphous state of at least the first portion of the elongate thermoplastic member 250A to the semi-crystalline state occurs during the embedding (e.g., at least according to block 606) of at least part of the elongate thermoplastic member 250A into at least the part of the wall 204 of the elongate shaft member 210. In some embodiments, heating one or more polymer materials to reflow and encapsulate the at least part of the elongate thermoplastic member 250A per at least block 606 causes the heating applied per block 604 to at least part of the elongate thermoplastic member 250A to change the amorphous state of at least the first portion of the elongate thermoplastic member 250A to the semi-crystalline state. In some embodiments, the heating per block 604 of the at least part of the axially adjacent elongate thermoplastic member 250A at least to change the amorphous state of at least the first portion of the elongate thermoplastic member 250A to the semi-crystalline state occurs during the reflowing per some embodiments of at least block 606 of one or more polymer materials over at least the tubular member (which may include low friction material layer 236).

As stated above, cold crystallization of at least the first portion of the axially adjacent elongate thermoplastic member 250A including the amorphous state occurs when the at least a first portion of the axially adjacent elongate thermoplastic member 250A may be heated above its glass transition temperature Tg, according to some embodiments. For example, in embodiments in which the axially adjacent elongate thermoplastic member 250A is made from polyether ether ketone (PEEK) with a glass transition temperature Tg of approximately 145° C., reflow temperatures greater than 169° C. (for example, the range of 174-220° C. reflow temperatures described above) can cause the transition of at least the first portion of the axially adjacent elongate thermoplastic member 250A from the amorphous state to the semi-crystalline state. According to some embodiments, the particular polymer layer (e.g., layer 205) of the one or more polymer layers of the wall 205 of the elongate shaft member 210 has a particular melt temperature, and the embedded at least the part (e.g., at least part 250A-1) of the elongate thermoplastic member (e.g., 250A) has a particular glass transition temperature. According to various embodiments, the particular glass transition temperature of the embedded at least the part of the elongate thermoplastic member (e.g., 250A) may be within 20% of the particular melt temperature at least in Celsius of the particular polymer layer of the one or more polymer layers of the wall of the elongate shaft member. According to various embodiments, the particular glass transition temperature of the embedded at least the part of the elongate thermoplastic member (e.g., 250A) may be within 20% in some embodiments, within 15% in some embodiments, and within 5% in some embodiments, of the particular melt temperature at least in Celsius of the particular polymer layer of the one or more polymer layers of the wall of the elongate shaft member. For example, polyether ether ketone (PEEK) has a glass transition temperature of approximately 145° C., which is approximately within 19% of the melt temperature (e.g., 178° C.) of Nylon 12 (VESTAMID (Registered Trademark as noted above)) including a 75 Shore D hardness described above, approximately within 17% of the melt temperature (e.g., 174° C.) of PEBAX (Registered Trademark as noted above) 7233 including a 69 Shore D hardness described above, and approximately within 1% of the melt temperature (e.g., 144° C.) of PEBAX (Registered Trademark as noted above) 3533 including a 33 Shore D hardness described above. In some embodiments, the embedded at least the part of the elongate thermoplastic member (e.g., 250A) has a particular melt temperature that is greater than the particular melt temperature of the particular polymer layer (e.g., 205) of the one or more polymer layers of the wall 204 of the elongate shaft member 210. For example, in embodiments in which the embedded at least the part of the elongate thermoplastic member (e.g., 250A) is made from polyether ether ketone (PEEK), its melt temperature of approximately 343° C. would be greater than the particular melt temperatures of Nylon 12 (VESTAMID (Registered Trademark as noted above)) including a 75 Shore D hardness, PEBAX (Registered Trademark as noted above) 7233 including a 69 Shore D hardness, and PEBAX (Registered Trademark as noted above) 3533 including a 33 Shore D hardness described above.

In the semi-crystalline state, at least the first portion of the axially adjacent elongate thermoplastic member (e.g., 250A) has improved rigidity and strength making it better suited to act as a strengthening member or stiffening member. Additionally, in some embodiments, the transitioning of at least the first portion of the axially adjacent elongate thermoplastic member (e.g., 250A) from the amorphous state to the semi-crystalline state is accompanied by a softening or slow melting of at least the outer, exterior, or external surface of at least the first portion of the axially adjacent elongate thermoplastic member (e.g., 250A) which may allow for an enhanced bond with the polymers that are reflowed to embed the at least the first portion of the axially adjacent elongate thermoplastic member (e.g., 250A) into at least part of the wall 204 of the elongate shaft member 210. This enhanced bonding advantageously reduces possible delamination of the elongate thermoplastic member (e.g., 250A) from the wall 204 of the elongate shaft member 210 during use, according to some embodiments. If at least the first portion of the axially adjacent elongate thermoplastic member (e.g., 250A) initially had a semi-crystalline state, the strength and rigidity of at least the first portion of the axially adjacent elongate thermoplastic member 250A would already exist, but the softening of the outer, exterior, or external surfaces of the at least the first portion of the axially adjacent elongate thermoplastic member (e.g., 250A) would not occur during the reflow process, and such aforementioned enhanced bonding would not occur at the relatively lower reflow temperatures of the encapsulating polymers according to some embodiments.

Block 608 of method 600 includes surrounding at least part of the elongate thermoplastic member (e.g., 250A) with at least part of a reinforcement structure 280, according to some embodiments. Various methods of surrounding at least part of the elongate thermoplastic member (e.g., 250A) with at least part of a reinforcement structure 280 have been described above. In this regard, for example, the surrounding per block 608 of at least part of the elongate thermoplastic member (e.g., 250A) with at least part of a braided reinforcement structure 280 may include weaving the elongate thermoplastic member (e.g., 250A) among or through braids of the braided reinforcement structure 280. For ease of discussion, the following portions of this disclosure will refer to braided reinforcement structure 280, according to some embodiments. It is noted that other reinforcement structures 280 may be employed in other embodiments.

Block 610 of method 600 includes embedding at least part of the braided reinforcement structure 280 into at least part of the wall 204 of the elongate shaft member 210. In some embodiments, the processes of block 606 are performed as part of block 610, but with the braided reinforcement structure 280 in place, such that, e.g., the polymer reflow encapsulates not only the elongate thermoplastic member (e.g., 250A), but also the braided reinforcement structure 280 to form wall 204 of elongate shaft member 210 as shown, e.g., in at least FIGS. 4C, 4D, and 4E.

According to various embodiments, the embedding per block 610 of at least part of the braided reinforcement structure 280 into the at least the part of the wall 204 of the elongate shaft member 210 includes embedding the first braided portion 280*a* of the braided reinforcement structure 280 in at least the first polymer portion 232*a* of the wall 204 of the elongate shaft member 210, the first polymer portion 232*a* including a first hardness; embedding the second braided portion 280*b* of the braided reinforcement structure 280 in at least the second polymer portion 232*b* of the wall 204 of the elongate shaft member 210, the second polymer portion 232*b* including a second hardness; and embedding the third braided portion 280*c* of the braided reinforcement structure 280 in at least the third polymer portion 232*c* of the wall 204 of the elongate shaft member 210, the third polymer portion 232*c* including a third hardness.

In some embodiments, the embedding per block 610 of at least part of the braided reinforcement structure 280 into the at least the part of the wall 204 of the elongate shaft member 210 includes embedding the first braided portion 280*a* and the transition portion 280*ac* of the braided reinforcement structure 280 in at least the first polymer portion 232*a*. In some embodiments, the embedding per block 610 of at least part of the braided reinforcement structure 280 into the at least the part of the wall 204 of the elongate shaft member 210 includes embedding the third braided portion 280*c* of the braided reinforcement structure 280 in at least the first polymer transition region 232*ac* and the third polymer portion 232*c*. In some embodiments, the embedding per block 610 of at least part of the braided reinforcement structure 280 into the at least the part of the wall 204 of the elongate shaft member 210 includes embedding the transition portion 280*cb* of the braided reinforcement structure 280 in at least the third polymer portion 232*c*. In some embodiments, the embedding per block 610 of at least part of the braided reinforcement structure 280 into the at least the part of the wall 204 of the elongate shaft member 210 includes embedding the second braided portion 280*b* of the braided reinforcement structure 280 in at least the second polymer transition region 232*cb* and the second polymer portion 232*b*.

In various embodiments, as discussed above, each of the first hardness and the second hardness is harder than the third hardness. And, as discussed above, in some embodiments, the first hardness is harder than the second hardness. In some embodiments, the method 600 may include, e.g., as part of block 610 or a preliminary part of block 610, directly fixedly connecting at least some filaments of the plurality of filaments 282 of the braided reinforcement structure 280 to the first ring 301, and directly fixedly connecting at least some filaments of the plurality of filaments 282 of the braided reinforcement structure 280 to the second ring 302.

According to some embodiments, the heating per block 604 of at least part of the axially adjacent elongate thermoplastic member (e.g., 250A) to change the at least the amorphous state of the first portion of the elongate thermoplastic member (e.g., 250A) to the semi-crystalline state occurs with the braided reinforcement structure 280 in place and causes at least a portion of the braided reinforcement structure 280 to embed into at least a first portion of the elongate thermoplastic member 250A to restrict at least axial movement of the elongate thermoplastic member 250A. In other words, for example, although FIG. 5 shows blocks 604, 608, and 610 as separate blocks, the actions therein may occur together, such that the changing of the amorphous state of the first portion of the elongate thermoplastic member (e.g., 250A) and the embedding of the braided reinforcement structure 280 into the wall 204 of the elongate shaft member 210 may occur via a same heating operation, according to some embodiments. In at least some of these instances, such a heating operation may cause sufficient softening of the elongate thermoplastic member (e.g., 250A) such that the braided reinforcement structure 280 partially embeds or 'bites' into the elongate thermoplastic member (e.g., 250A). Such 'biting' can beneficially help prevent or restrict axial movement of the elongate thermoplastic member (e.g., 250A) within the wall 204 of the elongate shaft member 210 during steering of the elongate shaft member 210. In this regard, such axial movement would be in a direction parallel to central longitudinal axis 230 of the elongate shaft member 210.

To elaborate, for example, in some embodiments, the embedding of at least part of the braided reinforcement structure 280 into at least the part of the wall 204 of the elongate shaft member 210 may include reflowing one or more polymer materials over at least the braided reinforcement structure 280. The reflow process typically involves, according to some embodiments, positioning the tubular member (which may include low friction material layer 236) on a mandrel and surrounding the tubular member (which may include low friction material layer 236) (and the axially adjacent part of the elongate thermoplastic member (e.g., 250A)) as well as the braided reinforcement structure 280 with one or more solid polymer layers. Heat shrink tubing may be positioned over the surrounding polymer layers and the assemblage is heated to temperatures sufficient to cause the one or more polymer layers to melt and reflow. The temperatures also cause the heat shrink tubing to shrink and compress the melted polymer layers to fill any voids that are present, such as those create by the openings in the braids of the braided reinforcement structure 280. The axially adjacent part of the elongate thermoplastic member (e.g., 250A) and the braided reinforcement structure 280 thus becomes embedded or encapsulated in the wall 204 of the elongate shaft member 210.

As described above, melting or softening (e.g., melting may be considered to include softening in some embodiments) of at least the outer, exterior, or external surfaces of the axially adjacent part of the elongate thermoplastic member (e.g., 250A) may occur as the at least the first portion of the axially adjacent elongate thermoplastic member (e.g., 250A) transitions between the amorphous state and the semi-crystalline state during the reflow process. According to various embodiments, the heat shrink tubing shrinks during the reflow process, thus embedding the braided reinforcement structure 280 into the melted or softened outer, exterior, or external surfaces of the axially adjacent part of the elongate thermoplastic member (e.g., 250A). It is noted that, in some embodiments, the outer, exterior, or external surfaces of the axially adjacent part of the elongate thermoplastic member (e.g., 250A) includes outwardly-facing (i.e., with respect to the inner-, interior-, or internal-most location 231) surfaces of the axially adjacent part of the elongate thermoplastic member (e.g., 250A). It is noted that, in some embodiments, the outer, exterior, or external surfaces of the axially adjacent part of the elongate thermoplastic member (e.g., 250A) includes inwardly-facing (i.e., with respect to the inner-, interior-, or internal-most location 231) surfaces of the axially adjacent part of the elongate thermoplastic member (e.g., 250A). Advantageously, this embedding secures the axially adjacent part of the elongate thermoplastic member (e.g., 250A) within the elongate shaft member 210, and eliminates, according to some embodiments, the need for additional securement connections, such as direct fixed connections of the elongate thermoplastic member 250A to first ring 301 and second ring 302. This embedding of the reinforcement structure 280 into the elongate thermoplastic member (e.g., 250A) also secures the axially adjacent part of the elongate thermoplastic member (e.g., 250A) within the elongate shaft member 210 in a compact and spatially efficient manner that can meet the required size constraints of the catheter. Other methods such as enlarging first ring 301 and second ring 302 to include pockets configured to secure the ends of axially adjacent elongate thermoplastic member (e.g., 250A) may adversely require a larger diameter catheter to accommodate these enlarged rings.

According to various embodiments, at least a first portion (e.g., at least first portion 250A-2) of the embedded at least the part of the elongate thermoplastic member (e.g., 250A) includes indentations (e.g., 330) in a surface (e.g., at least surface 250A-3) of the first portion of the embedded at least the part of the elongate thermoplastic member (e.g., 250A) into which the portion (e.g., at least the portion 280-2) of the embedded at least the part of the reinforcement structure (e.g., 280) is embedded, to, for example, prevent or restrict axial movement of the elongate thermoplastic member (e.g., 250A) within the wall 204 of the elongate shaft member 210 during steering of the elongate shaft member 210. According to some embodiments, a portion (e.g., 282*e*) of each filament (e.g., 282) of at least some of the plurality of filaments 282 is embedded in a respective indentation (e.g., 330) of the indentations in the surface of the first portion of the embedded at least the part of the elongate thermoplastic member (e.g., 250A) to, for example, prevent or restrict axial movement of the elongate thermoplastic member (e.g., 250A) within the wall 204 of the elongate shaft member 210 during steering of the elongate shaft member 210. It should be noted that, although portion 282*e*, as well as other references 330*d*, 330*di*, are shown in FIG. 4C with respect to elongate thermoplastic member 250B at least for purposes of clarity, corresponding references and descriptions also apply to elongate thermoplastic member 250A, in some embodiments. However, the preceding statement should not be interpreted to require that characteristics of the elongate thermoplastic members 250A, 250B and the reinforcement structure 280 in their vicinities must be identical.

A desired depth (e.g., 330*d*) of each of at least some of the indentations (e.g., 330) from the surface (e.g., at least surface 250A-3) of the first portion (e.g., at least first portion 250A-2) of the embedded at least the part (e.g., at least part 250A-1) of the elongate thermoplastic member (e.g., 250A) may be required for various reasons. For example, a particular desired depth of each of the at least some of the indentations may be required to ensure a required degree of axial securement capability of the elongate thermoplastic member (e.g., 250A) as a function of at least the reinforcement structure 280 being embedded into the indentations. As described above in this disclosure, the indentations may be produced in various manners. In some embodiments, the indentations (e.g., 330) may be formed when the at least the first portion of the elongate thermoplastic member (e.g., 250A) transitions between the amorphous state and the semi-crystalline state during the reflow process of the encapsulating polymer which causes the reinforcement structure 280 to embed into the surface of the elongate thermoplastic member (e.g., 250A) as described above.

Figure 4F:
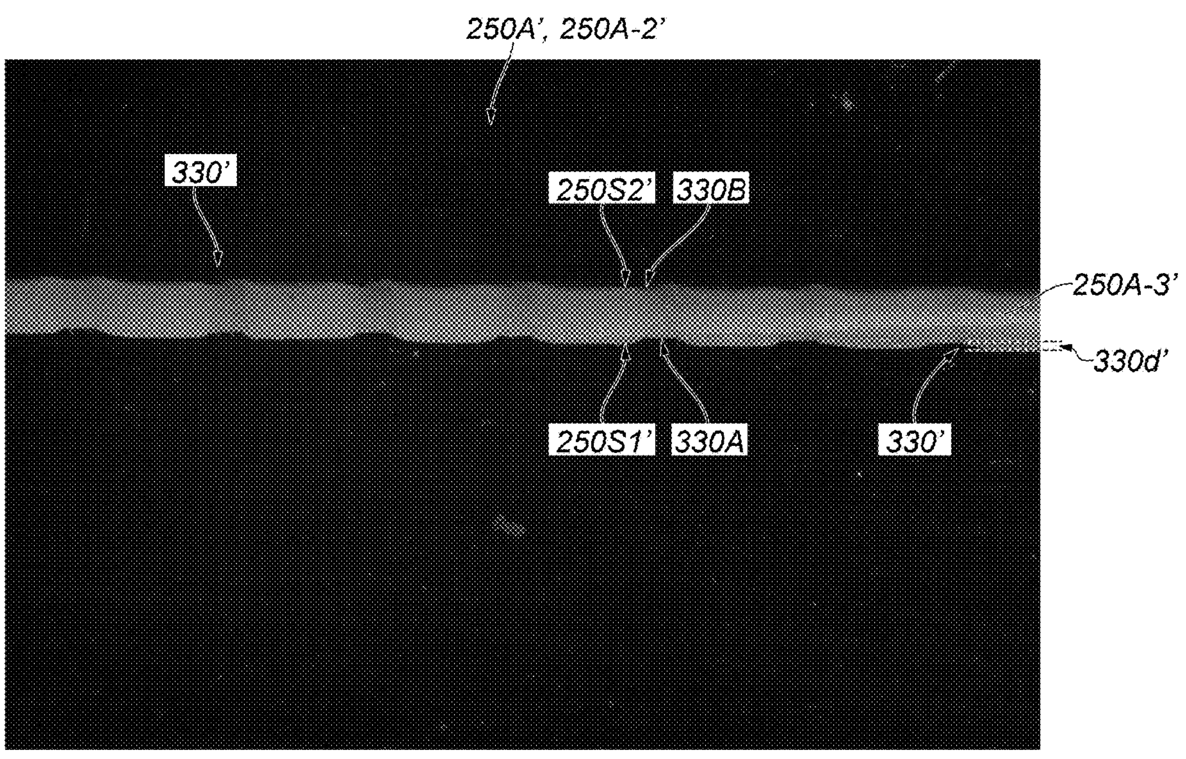
FIG. 4F is an image produced from a photograph of a portion of an elongate polyether ether ketone (PEEK) thermoplastic member 250A' having undergone cold crystallization from an amorphous state to a semi-crystalline state during a reflow procedure, according to some embodiments.

FIG. 4F is an image produced from a photograph of a first portion of an elongate polyether ether ketone (PEEK) thermoplastic member 250A' having undergone cold crystallization from an amorphous state to a semi-crystalline state during a reflow procedure (e.g., similar to that describe above) of the elongate thermoplastic member 250A' into an implementation of elongate shaft member 210 of a catheter. The elongate thermoplastic member 250A' was woven among the filaments of a braided reinforcement structure, an embodiment of the reinforcement structure 280. After the embedding, the catheter was disassembled and the elongate thermoplastic member 250A' was removed and sectioned along its longitudinal axis. FIG. 4F shows the sectioned elongate thermoplastic member 250A' (in isolation) including various indentations 330' (akin to indentations 330) formed by the braided reinforcement structure during the cold crystallization.

The surface 250A-3' (akin to surface 250A-3 in some embodiments) of a first portion 250A-2' (akin to first portion 250A-2 in some embodiments) of the elongate thermoplastic member 250A' includes a plurality of indentations 330' (two called out in FIG. 4F; akin to indentations 330 in some embodiments), a first surface portion 250S1' (akin to first surface portion 250S1, shown in FIG. 4C, in some embodiments) and a second surface portion 250S2' (akin to second surface portion 250S2, shown in FIG. 4C, in some embodiments), the first surface portion 250S1' located further radially closer to the longitudinal axis of the elongate shaft member of the catheter than the second surface portion 250S2'. In some embodiments, the first surface portion 250S1' and the second surface portion 250S2' are diametrically opposed to one another. According at least to the embodiment associated with FIG. 4F, a first set of indentations (one indentation in this first set called out as indentation 330A in FIG. 4F) are provided in the first surface portion 250S1', and a second set of indentations (one indentation in this second set called out as indentation 330B in FIG. 4F) are provided in the second surface portion 250S2'. A depth of at least one indentation (e.g., indentation 330A) of the first set of the indentations from the first surface portion 250S1' is different than a depth of at least one indentation (e.g., indentation 330B) of the second set of the indentations from the second surface portion 250S2', according to at least the embodiments associated with FIG. 4F. For illustration purposes, depth 330*d*' in FIG. 4F illustrates a depth of one of the indentations 330'. According to at least the embodiment associated with FIG. 4F, a depth of at least one indentation (e.g., indentation 330A) of the first set of the indentations from the first surface portion 250S1' is greater than a depth of at least one indentation (e.g., indentation 330B) of the second set of the indentations from the second surface portion 250S2'. This deeper indentation configuration on the radially interior side of the elongate thermoplastic member as compared to the radially exterior side of the elongate thermoplastic member also is illustrated in FIG. 4C, where indentation depth 330*di* on the radially interior side of the elongate thermoplastic member 250B is greater than indentation depth 330*d* on the radially exterior side of the elongate thermoplastic member 250B.

Each of at least one filament of the plurality of filaments of the reinforcement structure employed in the embodiment of FIG. 4F has a particular dimension (e.g., corresponding to particular dimension 282*d*) of 76 microns in a radial direction (e.g., akin to radial direction 210*c*) with respect to the longitudinal axis of the elongate shaft member. The indentation depths of the first set of indentations in the embodiment of FIG. 4F were measured to be approximately 50-70 microns (or approximately 65% to 92% of the filament particular dimension), and the indentation depths of the second set of indentations were measured to be approximately 30 microns (or approximately 39% of the filament particular dimension).

Figure 4G:
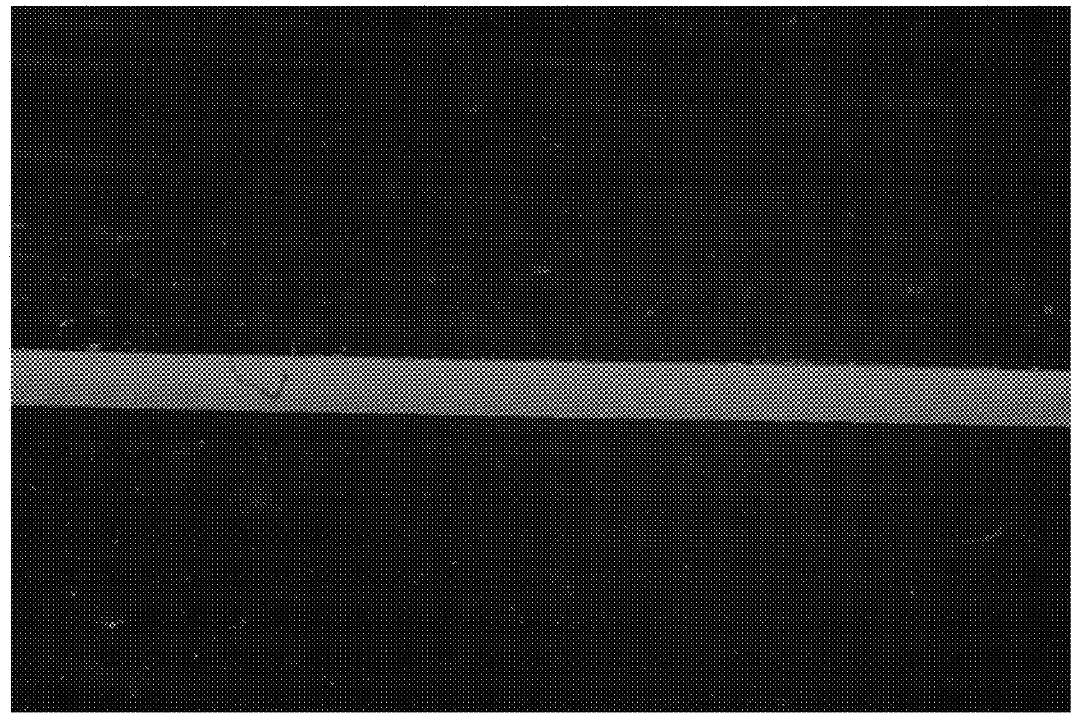
FIG. 4G is an image produced from a photograph of a portion of an elongate PEEK thermoplastic member having an initial semi-crystalline state during a reflow procedure, which did not undergo cold crystallization, according to some embodiments.

FIG. 4G is an image produced from a photograph of a first portion of an elongate polyether ether ketone (PEEK) thermoplastic member having an initial semi-crystalline state during a reflow procedure (e.g., similar to that describe above) of the elongate thermoplastic member into an elongate shaft member of a catheter. In this regard, the first portion of the elongate thermoplastic member did not undergo cold crystallization during the reflow procedure as it was already in an initial semi-crystalline state. The semi-crystalline elongate thermoplastic member was woven among the filaments of a braided reinforcement structure. After the embedding, the catheter was disassembled and the elongate thermoplastic member was removed and sectioned along its longitudinal axis. FIG. 4G shows the sectioned elongate thermoplastic member including little indentation. The present inventors were not able to measure any indentations that were present. According to some embodiments, the presence of indentations (e.g., indentations 330, 330A, 330B) are a characteristic exhibited by at least a respective portion of the elongate thermoplastic member that has undergone cold crystallization, although, as discussed above, such indentations may be formed by other processes.

The present inventors have found that when the filaments (e.g., 282) of the reinforcement structure (e.g., 280) are embedded into the pronounced indentations (e.g., indentations 330, 330A, 330B of the elongate thermoplastic member (e.g., 250A, 250B, or both), the elongate thermoplastic member is provided with an enhanced ability to restrict at least axial movement of the elongate thermoplastic member within the elongate shaft member (e.g., 210, for example, during flexing or steering). In comparison, the lack of pronounced indentation in the elongate thermoplastic member of FIG. 4G provides a reduced ability to restrict at least axial movement of the elongate thermoplastic member within the elongate shaft member. The present inventors have found that providing an elongate thermoplastic member (e.g., 250A, 250B, or both) with indentations (e.g., 330) in which a depth of each of at least some of the indentations from the surface of the respective portion or portions of the embedded at least part of the elongate thermoplastic member is at least 40% of the particular dimension (e.g., 282*d*) of the respective filament 282 of the reinforcement structure 280 provides enhanced ability to restrict at least axial movement of the elongate thermoplastic member (e.g., 250A) within the elongate shaft member 210. The present inventors also recognize that the other depth proportion ranges discussed above also provide benefits in various embodiments. In some embodiments, as discussed above, the heating per block 604 of at least part of the axially adjacent elongate thermoplastic member (e.g., 250A) to change at least the amorphous state of the first portion of the elongate thermoplastic member (e.g., 250A) to the semi-crystalline state may cause the embedding of block 610. In some embodiments, such heating may cause at least each of the first braided portion 280*a* of the braided reinforcement structure 280 and the second braided portion 280*b* of the braided reinforcement structure 280 to embed deeper into at least the (e.g., the first portion 232*a*, in some embodiments of the) elongate thermoplastic member (e.g., 250A) than the third braided portion 280*c* of the braided reinforcement structure 280 (e.g., the third braided portion 280*c* embedding into at least the third portion 232*c* of the elongate thermoplastic member (e.g., 250A), in some embodiments).

As described above, in some embodiments, the third pick count of the third braided portion 280*c* is greater than each of the first pick count of the first braided portion 280*a* and the second pick count of second braided portion 280*b*. This higher pick count is associated with a higher filament density in the third braided portion 280*c*. This higher filament density has a higher surface area which reduces the amount that the third braided portion 280*c* of the braided reinforcement structure 280 can be embedded into at least the first portion of the axially adjacent elongate thermoplastic member (e.g., 250A). In contrast, the relatively lower pick counts of the first braided portion 280*a* and second braided portion 280*b* of the braided reinforcement structure 280 are each associated with lower filament density having a lower surface area that relatively increases the amount that the first braided portion 280*a* and second braided portion 280*b* of the braided reinforcement structure 280 can be embedded into the at least the first portion of the axially adjacent elongate thermoplastic member (e.g., 250A). According to various embodiments, the use of the second braided portion 280*b* extending over at least part of the distal portion 213 of the elongate shaft member 210 advantageously allows the particular part of the axially adjacent elongate thermoplastic member (e.g., 250A) extending in the distal portion 213 to be better secured, as compared to a situation in which the second braided portion 280*b* were omitted and the third braided portion 280*c* were extended to secure the particular part of the axially adjacent elongate thermoplastic member (e.g., 250A) extending in the distal portion 213.

According to some embodiments, the part of the braided reinforcement structure 280 surrounding at least part of the elongate thermoplastic member (e.g., 250A) is a first part of the braided reinforcement structure 280, and in some embodiments in which the method 600 includes providing a steerable catheter with an actuator (such as actuator device system 240) that is operatively coupled to a steering member 226, block 608 of the method 600 may include surrounding at least part of the steering member 226 with at least a second part of the braided reinforcement structure 280 (for example, as shown in FIGS. 4C, 4D, and 4E). The same may apply for steering member 228, which may be surrounded by another part of the braided reinforcement structure 280. It is noted in various embodiments, that steering member mandrels (with overlying steering member liners in some embodiments) are axially fed or pulled by the braider during the braiding of the braided reinforcement structure 280 (for example, in a manner similar to that described above for the axial members 250A, 250B). In some embodiments, after the braided reinforcement structure 280 has been formed, and in some embodiments, at least part of the wall 204 of the elongate shaft member 210 has been formed, the steering member mandrels are removed and at least part of the steering members 226, 228 is incorporated into the wall 204 by, e.g., inserting them through the voids left by the removed steering member mandrels, according to some embodiments. In this regard, it may be considered that the method 600 includes, according to some embodiments, incorporating at least a portion of a steering member (e.g., steering member 226 or steering member 228) into at least a portion of the wall 204 of the elongate shaft member 210.

In some embodiments, at least as part of block 608, the method 600 may include incorporating at least part of a steering ring (e.g., at least second ring 302) into at least part (referred to as a "second portion" in some contexts) of the wall 204 of the elongate shaft member 210. In some embodiments, the method 600 may include providing at least part (e.g., called a "second" part in some contexts, which may be an end portion of second braided portion 280*b*) of the braided reinforcement structure 280 radially exterior, with respect to a central longitudinal axis 230 of the elongate shaft member 210, of at least a region of the steering ring. In some embodiments, the method 600 may include surrounding the steering ring with at least part (e.g., the "second part" in some contexts) of the braided reinforcement structure 280. According to some embodiments, the method 600 may include directly fixedly connecting the steering member 226 to the steering ring. As discussed above, for example, with respect to FIGS. 4D and 4E, a distal portion of the second braided portion 280*b* may be radially exterior of or surround the second ring 302, and that portion of the second braided portion 280*b* may be directly fixedly connected to the second steering ring 302 as part of block 608 of method 600, according to some embodiments. The same applies for steering member 228, according to some embodiments. In some embodiments, the steering members 226, 228 are a metallic steering member, and the steering ring (e.g., second ring 302) is a metallic steering ring, and directly fixedly connecting the steering member 226 (or 228) to the steering ring (e.g., such as ring 302 in some embodiments) includes welding the metallic steering member to the metallic steering ring. In some embodiments, directly fixedly connecting the steering member 226 (or 228) to the steering ring is performed through an opening defined by braids of the braided reinforcement structure 280, as discussed above. In some embodiments in which the steering member 226 (or 228) and the steering ring (e.g., such as ring 302 in some embodiments) are metallic, the directly fixedly connecting the steering member 226 (or 228) to the steering ring includes welding the metallic steering member to the metallic steering ring through the opening defined by braids of the braided reinforcement structure 280.

According to some embodiments, the semi-crystalline state, to which the amorphous state of the at least the first portion of the elongate thermoplastic member (e.g., 250A) is changed by the heating associated with block 604, is a first semi-crystalline state. In some embodiments, the axially adjacent elongate thermoplastic member (e.g., 250A) (e.g., block 602) concurrently includes, with the first portion of the elongate thermoplastic member (e.g., 250A) including the amorphous state, a second portion including a second semi-crystalline state in which the second portion of the elongate thermoplastic member (e.g., 250A) includes a greater degree of crystallinity than the first portion of the elongate thermoplastic member (e.g., 250A) including the amorphous state. In some embodiments, the second portion of the elongate thermoplastic member (e.g., 250A) occupies at least in part, a different axial region of the elongate thermoplastic member (e.g., 250A) than the first portion of the elongate thermoplastic member (e.g., 250A) along a length of the elongate thermoplastic member (e.g., 250A). For example, according to some embodiments, the portion of the elongate thermoplastic member shown in FIG. 4G could be such a second portion including or having the second semi-crystalline state, and the portion of the elongate thermoplastic member shown in FIG. 4F could be such a first portion, where the portions of FIG. 4F and FIG. 4G may be different portions of the same elongate thermoplastic member in some embodiments. According to various embodiments, the elongate thermoplastic member (e.g., 250A) (e.g., in the state of block 602) concurrently includes the first portion of the elongate thermoplastic member 250A including the amorphous state and the second portion of the elongate thermoplastic member (e.g., 250A) including the second semi-crystalline state prior to the heating of block 604. According to various embodiments, the axially adjacent elongate thermoplastic member (e.g., 250A) (e.g., in the state of block 602) concurrently includes the first portion of the elongate thermoplastic member (e.g., 250A) including the amorphous state and the second portion of the elongate thermoplastic member (e.g., 250A) including the second semi-crystalline state prior to the heating of block 604. According to various embodiments, the elongate thermoplastic member (e.g., 250A) concurrently includes the first portion of the elongate thermoplastic member (e.g., 250A) including the amorphous state and the second portion of the elongate thermoplastic member (e.g., 250A) including the second semi-crystalline state prior to the axially positioning of block 602.

In some embodiments, the first portion of the elongate thermoplastic member (e.g., 250A) including the amorphous state includes a first part and a second part, and the second portion of the elongate thermoplastic member (e.g., 250A) including the second crystalline state is axially located between the first part and the second part of the first portion of the elongate thermoplastic member (e.g., 250A). In other words, in some embodiments, the semi-crystalline second portion of the elongate thermoplastic member (e.g., 250A) may be considered a sub-region in a middle of the amorphous first portion of the elongate thermoplastic member. For example, the semi-crystalline second portion of the elongate thermoplastic member (e.g., 250A) may correspond to a region of the elongate thermoplastic member (e.g., 250A) under the third braided portion 280*c* shown in FIGS. 4D and 4E in some embodiments, and the amorphous first portion of the elongate thermoplastic member (e.g., 250A) may correspond to a region of the elongate thermoplastic member (e.g., 250A) under first braided portion 280*a* and second braided portion 280*b* in some embodiments.

In some embodiments, the semi-crystalline second portion of the elongate thermoplastic member (e.g., 250A) may be provided by a preliminary heating process. For example, the entirety of the elongate thermoplastic member (e.g., 250A) may be in an amorphous state prior to the state of block 602, and a part, but not all, of the elongate thermoplastic member (e.g., 250A) may be heated in a preliminary (e.g., before block 602) heating process to form the semi-crystalline second portion of the elongate thermoplastic member (e.g., 250A). In some of these embodiments, after the preliminary heating process, the elongate thermoplastic member (e.g., 250A) may concurrently include one or more amorphous portions and the newly-produced semi-crystalline portion.

In some embodiments, the first portion (whether amorphous pre-block 604 or semi-crystalline post-block 604) of the elongate thermoplastic member (e.g., 250A) is positioned to extend through at least part of the proximal portion 212 of the elongate shaft member 210 when the elongate thermoplastic member (e.g., 250A) is embedded in the wall 204 of the elongate shaft member 210, and the semi-crystalline second portion of the elongate thermoplastic member (e.g., 250A) is positioned to extend through at least part of the steerable portion 219 of the elongate shaft member 210 when the elongate thermoplastic member (e.g., 250A) is embedded in the wall 204 of the elongate shaft member 210. In some embodiments, method 600 includes surrounding both the first portion of the elongate thermoplastic member (e.g., 250A) and the second portion of the elongate thermoplastic member (e.g., 250A) with a braided reinforcement structure 280 per the above discussions. According to some embodiments, the heating per block 604 of at least part of the elongate thermoplastic member (e.g., 250A) to change at least the amorphous state of the first portion of the elongate thermoplastic member (e.g., 250A) to the first semi-crystalline state causes the braided reinforcement structure 280 to embed deeper into the first portion of the elongate thermoplastic member (e.g., 250A) than into the second portion of the elongate thermoplastic member (e.g., 250A). It is noted that, in various embodiments, the second portion of the elongate thermoplastic member (e.g., 250A) including the second semi-crystalline state remains semi-crystalline during the heating of block 604. In this regard, according to various embodiments, during the heating, the second portion of the elongate thermoplastic member (e.g., 250A) including the second semi-crystalline state does not soften like the first portion of the elongate thermoplastic member (e.g., 250A) including the original amorphous state, and the braided reinforcement structure 280 is restricted from embedding to any significant extent into the second portion of the elongate thermoplastic reinforcement member (e.g., 250A) extending through the steerable portion 219 of the elongate shaft member 210. Since little to no amount of embedding exists, there are little to no indentations or corrugations formed in the second portion of the elongate thermoplastic member (e.g., 250A) which is advantageous, in some embodiments, since indentations or corrugations in the second portion of the elongate thermoplastic member (e.g., 250A) may render the second portion of the elongate thermoplastic member (e.g., 250A) more susceptible to compressive buckling.

While some of the embodiments disclosed above are described with examples of cardiac procedures, the same or similar embodiments may be used for procedures for other bodily organs or any lumen or cavity into which the devices of the present invention may be introduced.

Subsets or combinations of various embodiments described above provide further embodiments.

These and other changes can be made to the invention in light of the above-detailed description. In general, in the following claims, the terms used should not be construed to limit the invention to the specific embodiments disclosed in the specification and the claims, but should be construed to include other catheter-based device systems including all medical treatment device systems and medical diagnostic device systems in accordance with the claims. Accordingly, the invention is not limited by the disclosure, but instead its scope is to be determined entirely by the following claims.

What is claimed is:

1. A catheter comprising:

an elongate shaft member comprising a proximal portion, a distal portion, and a wall, the elongate shaft member configured to be deliverable at least partially through a bodily opening leading to a bodily cavity with the distal portion ahead of the proximal portion, and the wall of the elongate shaft member comprising one or more polymer layers;

an elongate thermoplastic member, at least part of the elongate thermoplastic member embedded into at least a particular polymer layer of the one or more polymer layers of the wall of the elongate shaft member, the embedded at least the part of the elongate thermoplastic member extending along or with a longitudinal axis of the elongate shaft member between the proximal portion of the elongate shaft member and the distal portion of the elongate shaft member; and a reinforcement structure surrounding the embedded at least the part of the elongate thermoplastic member, at least part of the reinforcement structure embedded into the wall of the elongate shaft member, at least a portion of the embedded at least the part of the reinforcement structure comprising a plurality of filaments, each of at least one filament of the plurality of filaments having a particular dimension in a radial direction with respect to the longitudinal axis of the elongate shaft member, wherein at least a first portion of the embedded at least the part of the elongate thermoplastic member includes indentations in a surface of the first portion of the embedded at least the part of the elongate thermoplastic member into which the portion of the embedded at least the part of the reinforcement structure is embedded, and wherein a depth of each of at least some of the indentations from the surface of the first portion of the embedded at least the part of the elongate thermoplastic member is at least 40% of the particular dimension of the respective filament.

2. The catheter of claim 1, wherein the first portion of the embedded at least the part of the elongate thermoplastic member has a semi-crystalline state.

3. The catheter of claim 1, wherein at least the first portion of the embedded at least the part of the elongate thermoplastic member exhibits a characteristic of having undergone cold crystallization.

4. The catheter of claim 2, wherein the particular polymer layer of the one or more polymer layers of the wall of the elongate shaft member has a particular melt temperature, and wherein the embedded at least the part of the elongate thermoplastic member has a particular glass transition temperature, the particular glass transition temperature of the embedded at least the part of the elongate thermoplastic member within 20% of the particular melt temperature at least in Celsius of the particular polymer layer of the one or more polymer layers of the wall of the elongate shaft member.

5. The catheter of claim 4, wherein the embedded at least the part of the elongate thermoplastic member has a particular melt temperature that is greater than the particular melt temperature of the particular polymer layer of the one or more polymer layers of the wall of the elongate shaft member.

6. The catheter of claim 1, wherein at least the part of the reinforcement structure is embedded in at least the particular polymer layer of the one or more polymer layers of the wall of the elongate shaft member.

7. The catheter of claim 1, wherein the particular polymer layer of the one or more polymer layers of the wall of the elongate shaft member is a tubular layer.

8. The catheter of claim 7, wherein the tubular layer includes an outer surface and an inner surface radially inward from the outer surface with respect to the longitudinal axis of the elongate shaft member, the embedded at least the part of the elongate thermoplastic member located between the outer surface and the inner surface.

9. The catheter of claim 1, wherein the reinforcement structure comprises a helical structure.

10. The catheter of claim 1, wherein a first set of the plurality of filaments are wound in a first direction and a second set of the plurality of filaments are wound in a second direction opposite the first direction.

11. The catheter of claim 1, wherein the reinforcement structure comprises a braided structure.

12. The catheter of claim 11, wherein the embedded at least the part of the elongate thermoplastic member is woven among braids of the braided structure.

13. The catheter of claim 1, wherein the embedded at least the part of the elongate thermoplastic member is woven among at least some of the plurality of filaments.

14. The catheter of claim 1, wherein a portion of each filament of at least some of the plurality of filaments is embedded in a respective indentation of the indentations in the surface of the first portion of the embedded at least the part of the elongate thermoplastic member.

15. The catheter of claim 1, wherein the surface of the first portion of the embedded at least the part of the elongate thermoplastic member comprises a first surface portion and a second surface portion, the first surface portion located radially closer to the longitudinal axis of the elongate shaft member than the second surface portion, and wherein a first set of the indentations are provided in the first surface portion and a second set of the indentations are provided in the second surface portion.

16. The catheter of claim 15, wherein a depth of at least one indentation of the first set of the indentations from the first surface portion is different than a depth of at least one indentation of the second set of the indentations from the second surface portion.

17. The catheter of claim 15, wherein a depth of at least one indentation of the first set of the indentations from the first surface portion is greater than a depth of at least one indentation of the second set of the indentations from the second surface portion.

18. The catheter of claim 1, wherein the elongate thermoplastic member is a first elongate thermoplastic member, the catheter comprising a second elongate thermoplastic member, at least part of the second elongate thermoplastic member embedded into the wall of the elongate shaft member, at least a portion of the second elongate thermoplastic member positioned diametrically opposite across at least one cross-section of the elongate shaft member from at least a portion of the first elongate thermoplastic member.

19. The catheter of claim 1, wherein the elongate shaft member comprises a steerable portion, and the catheter comprises an actuator located at least proximate the proximal portion of the elongate shaft member, the actuator operatively coupled to the steerable portion to transmit force thereto to steer at least the steerable portion.

20. The catheter of claim 19, wherein the steerable portion of the elongate shaft member is located between the proximal portion of the elongate shaft member and the distal portion of the elongate shaft member.

21. The catheter of claim 19, wherein the actuator is operatively coupled to the steerable portion to cause deflection of the at least the steerable portion in a first particular plane, and wherein the elongate thermoplastic member is configured at least to resist, at least in part, lateral deflection of the at least the steerable portion away from the first particular plane during the deflection of the at least the steerable portion in the first particular plane.

22. The catheter of claim 21, wherein the elongate thermoplastic member is a first elongate thermoplastic member, and wherein the catheter comprises a second elongate thermoplastic member, at least part thereof embedded in the wall of the elongate shaft member and extending between the proximal portion of the elongate shaft member and the distal portion of the elongate shaft member, each of the first elongate thermoplastic member and the second elongate thermoplastic member including a respective axis extending between the proximal portion of the elongate shaft member and the distal portion of the elongate shaft member, wherein the second elongate thermoplastic member is configured at least to resist, at least in part, the lateral deflection of the at least the steerable portion away from the first particular plane during the deflection of the at least the steerable portion in the first particular plane, and wherein the respective axis of the first elongate thermoplastic member and the respective axis of the second elongate thermoplastic member lie in a second particular plane, the second particular plane intersecting the first particular plane.

23. The catheter of claim 22, wherein the second particular plane is orthogonal to the first particular plane.

24. The catheter of claim 21, comprising a first steering member and a second steering member, wherein the actuator is configured to manipulate the first steering member, the second steering member, or both the first steering member and the second steering member, to cause deflection of the at least the steerable portion in the first particular plane.

25. The catheter of claim 24, wherein at least a first portion of the reinforcement structure surrounds at least a respective portion of each of the first steering member and the second steering member.

26. The catheter of claim 24, wherein the reinforcement structure comprises a braided structure, wherein at least the first steering member is woven among braids of the braided structure.

27. The catheter of claim 1, wherein the first portion of the embedded at least the part of the elongate thermoplastic member has been melted about the portion of the embedded at least the part of the reinforcement structure to embed the portion of the embedded at least the part of the reinforcement structure into the surface of the first portion of the embedded at least the part of the elongate thermoplastic member, thereby forming the indentations.

28. The catheter of claim 27, wherein the first portion of the embedded at least the part of the elongate thermoplastic member has a semi-crystalline state.

29. The catheter of claim 1, wherein at least the first portion of the embedded at least the part of the elongate thermoplastic member comprises a polyaryletherketone (PAEK) polymer.

30. The catheter of claim 29, wherein the polyaryletherketone (PAEK) polymer is polyether ether ketone (PEEK).

* * * * *